(12) United States Patent
Nazari et al.

(10) Patent No.: US 12,064,209 B2
(45) Date of Patent: Aug. 20, 2024

(54) WIRELESS SENSING PLATFORM FOR MULTI-ANALYTE SENSING

(71) Applicant: Integrated Medical Sensors, Inc., Irvine, CA (US)

(72) Inventors: Meisam Honarvar Nazari, Irvine, CA (US); Muhammad Mujeeb-U-Rahman, Irvine, CA (US); Mehmet Sencan, Culver City, CA (US)

(*) Notice: Subject to any disclaimer, the term of this patent is extended or adjusted under 35 U.S.C. 154(b) by 525 days.

(21) Appl. No.: 16/612,391

(22) PCT Filed: May 8, 2018

(86) PCT No.: PCT/US2018/031629
§ 371 (c)(1),
(2) Date: Nov. 10, 2019

(87) PCT Pub. No.: WO2019/005301
PCT Pub. Date: Jan. 3, 2019

(65) Prior Publication Data
US 2020/0178801 A1 Jun. 11, 2020

Related U.S. Application Data

(60) Provisional application No. 62/527,525, filed on Jun. 30, 2017.

(51) Int. Cl.
*A61B 5/00* (2006.01)
*A61B 5/145* (2006.01)
*A61B 5/1473* (2006.01)

(52) U.S. Cl.
CPC ............ *A61B 5/0031* (2013.01); *A61B 5/002* (2013.01); *A61B 5/14532* (2013.01);
(Continued)

(58) Field of Classification Search
CPC ...... A61B 5/002; A61B 5/0031; A61B 5/1473
See application file for complete search history.

(56) References Cited

U.S. PATENT DOCUMENTS 7,800,078 B2 9/2010 Colvin et al.
8,922,366 B1 12/2014 Honoré et al.
(Continued)

FOREIGN PATENT DOCUMENTS

KR 20140082642 A 7/2014

OTHER PUBLICATIONS

International Search Report of PCT/US2018/031629 mailed on Jul. 20, 2018.
(Continued)

*Primary Examiner* — Rex R Holmes
*Assistant Examiner* — Jennifer L Ghand

(57) ABSTRACT

Monitoring of one or more key indicators can provide powerful insights into the operation and state of different physical systems. For example, continuous monitoring of multiple analytes in a subject allows for detailed insights into personal health as well as allowing for the implementation of preventative health measures. Herein are described design and processing methods for a small wireless multi-analyte sensing platform that can be used to monitor multiple analytes such as glucose, lactate, Urea and other physicochemical quantities. The design techniques and processing methods presented herein can be used for a multitude of other applications and are not limited to those described here.

23 Claims, 44 Drawing Sheets

(52) U.S. Cl.
CPC .......... *A61B 5/1473* (2013.01); *A61B 5/7275* (2013.01); *A61B 2560/0219* (2013.01)

(56) References Cited

U.S. PATENT DOCUMENTS

| | | | |
|---|---|---|---|
| 9,006,014 | B2 | 4/2015 | Mujeeb-U-Rahman et al. |
| 9,173,605 | B2 | 11/2015 | Mujeeb-U-Rahman et al. |
| 9,177,933 | B2 | 11/2015 | Mujeeb-U-Rahman et al. |
| 9,672,393 | B1 | 6/2017 | Zhu et al. |
| 10,172,520 | B2 | 1/2019 | Scherer et al. |
| 10,368,788 | B2 | 8/2019 | Scherer et al. |
| 10,376,146 | B2 | 8/2019 | Mujeeb-U-Rahman et al. |
| 10,612,078 | B2 | 4/2020 | Honarvar Nazari et al. |
| 10,820,844 | B2 | 11/2020 | Scherer |
| 10,959,617 | B2 | 3/2021 | Scherer et al. |
| 11,026,610 | B2 | 6/2021 | Chen et al. |
| 2005/0215977 | A1 | 10/2005 | Uschold |
| 2009/0101498 | A1 | 4/2009 | Papadimitrakopoulos et al. |
| 2012/0078072 | A1 | 3/2012 | Roesicke et al. |
| 2014/0336474 | A1* | 11/2014 | Arbabian ................ H02J 50/90 600/300 |
| 2014/0367246 | A1 | 12/2014 | Shah et al. |
| 2015/0265182 | A1* | 9/2015 | Jain ...................... A61B 5/1495 606/129 |
| 2016/0249837 | A1 | 9/2016 | Lin |
| 2017/0001003 | A1* | 1/2017 | Pivonka ............... A61B 5/4836 |
| 2017/0020415 | A1* | 1/2017 | Scherer .................. A61B 5/076 |
| 2018/0125364 | A1* | 5/2018 | DeHennis ............... G16Z 99/00 |
| 2018/0338681 | A1 | 11/2018 | Scherer et al. |
| 2020/0178801 | A1* | 6/2020 | Nazari ................. A61B 5/1473 |
| 2022/0031244 | A1* | 2/2022 | Windmiller ........ A61B 5/14865 |

OTHER PUBLICATIONS

Written Opinion of the International Search Authority of PCT/US2018/031629 mailed on Jul. 20, 2018.

Robbins, Rebecca (Nov. 16, 2018). Watch: After five years, Verily shelves project to create glucose-sensing contact lens. Stat: Reporting from the frontiers of health and medicine.

Morris, N.M. (1976). Monolithic Integrated Circuits. In: Semiconductor Devices. Macmillan Basis Books in Electronics. pp. 119-120. Palgrave, London. Print ISBN: 978-0-333-18536-0.

Extended European Search Report for EP 18825462.7-1115/3644843 PCT/US2018031629. Jul. 28, 2020.

Partial Supplementary European Search Report for EP 18825462.7-1115/3644843 PCT/US2018031629. Apr. 24, 2020.

Request for Entry into the European Phase for EP 18825462.7-1115/3644843 PCT/US2018031629. Jan. 14, 2020.

Response to the Search Opinion for EP 18825462.7. May 28, 2021.

Meisam Honavar Nazari, Muhammad Mujeeb-U-Rahman, and Axel Scherer, 2014 Symposium on VLSI Circuits Digest of Technical Papers.

Muhammad Mujeeb-U-Rahman, Dvin Adalian, Chieh-Feng Chang, and Axel Scherer, J. Biomedical Optics, 20(9), 095012 (2015).

Muhammad Mujeeb-U-Rahman, Chieh-Feng Chang, and Axel Scherer, Proceedings vol. 8812, Biosensing and Nanomedicine VI; 88120M (2013).

Muhammad Mujeeb-U-Rahman, Integrated Microsystems for Wireless Sensing Applications, 2014.

Communication pursuant to Article 94(3) EPC for EP 18825462.7, Aug. 10, 2022.

* cited by examiner

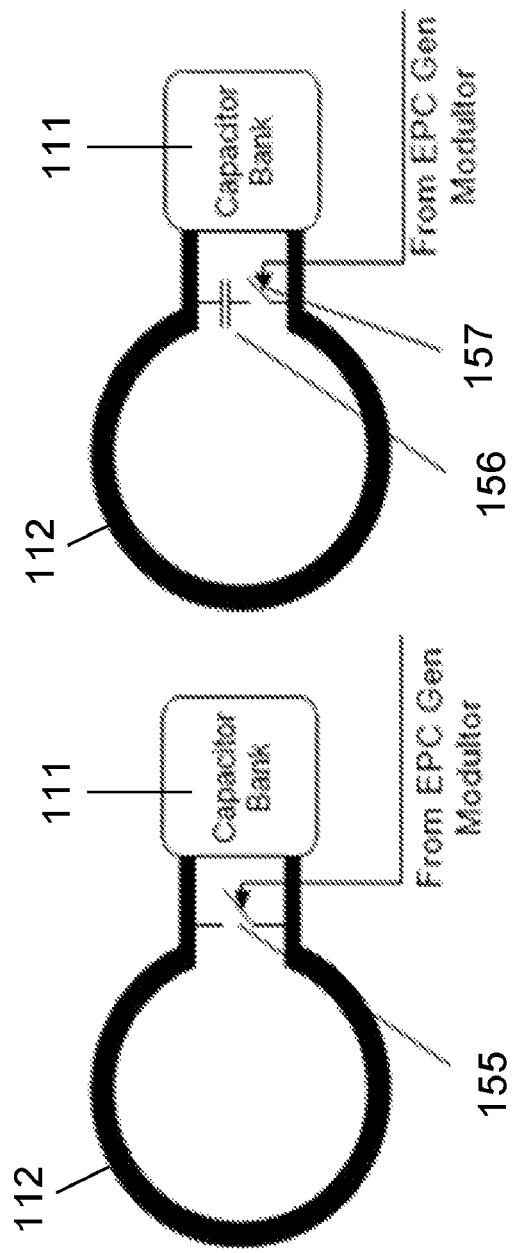

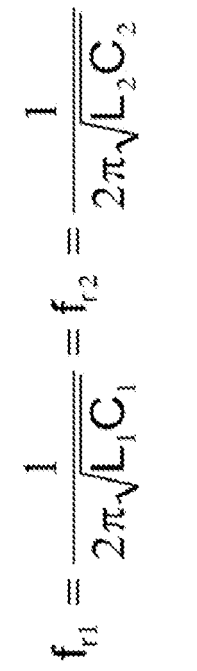
Fig. 5C
Fig. 5D
Fig. 5E
$$f_{r1} = \frac{1}{2\pi\sqrt{L_1 C_1}} = f_{r2} = \frac{1}{2\pi\sqrt{L_2 C_2}}$$
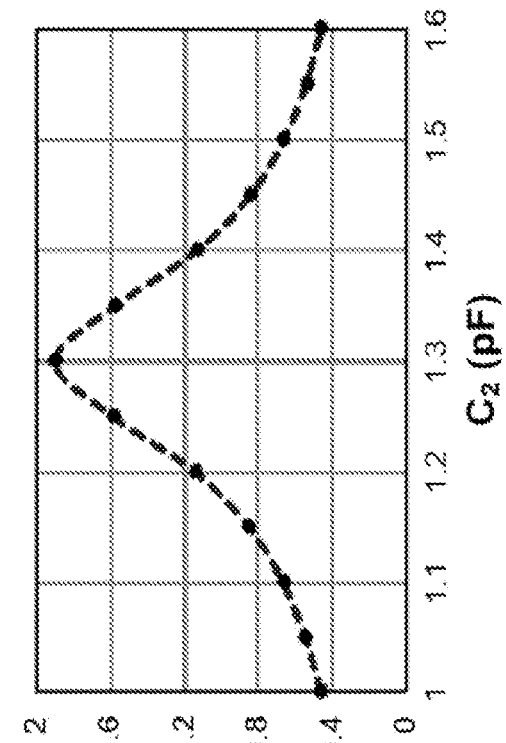
Fig. 5B
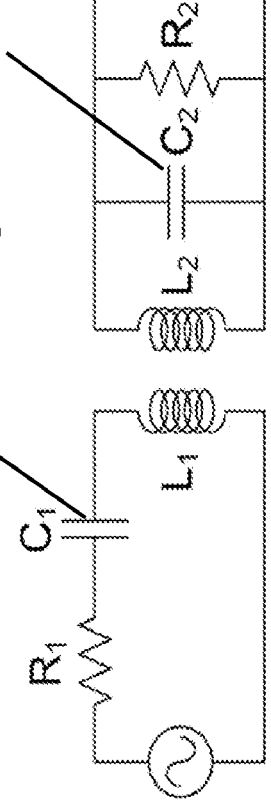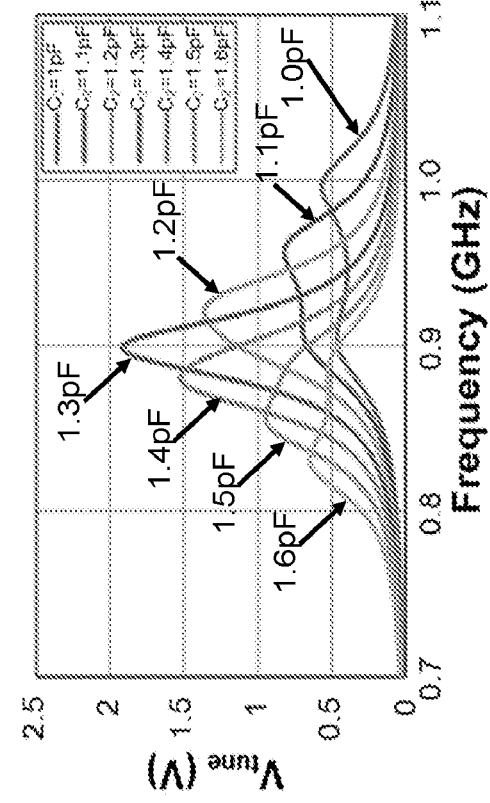
Fig. 5A

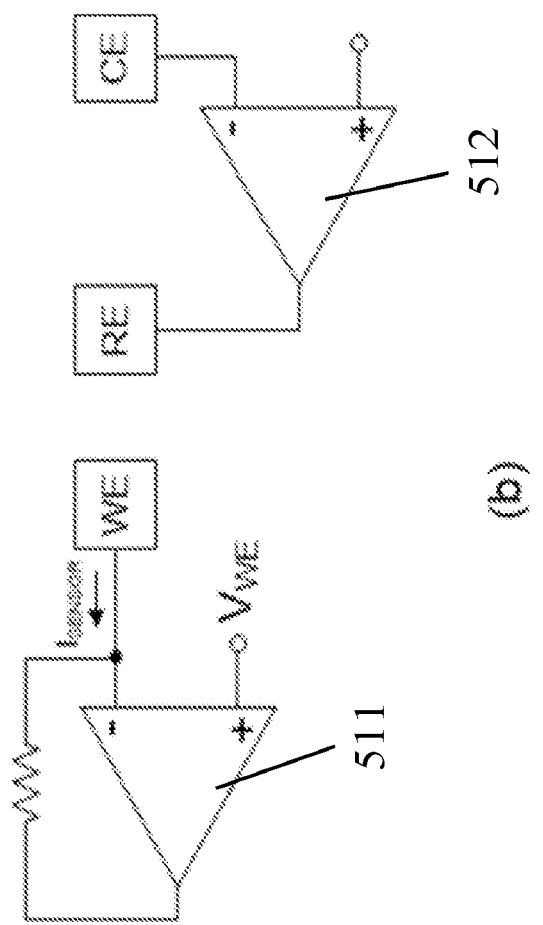
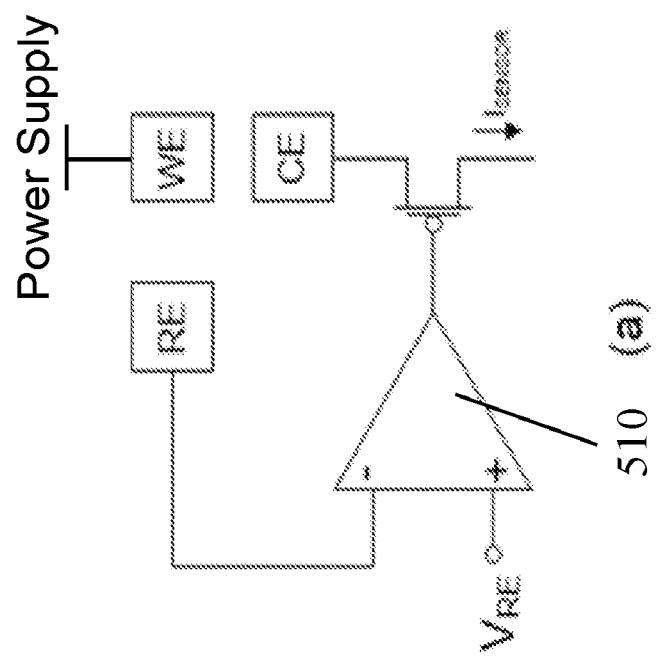
Fig. 11A
Fig. 11B

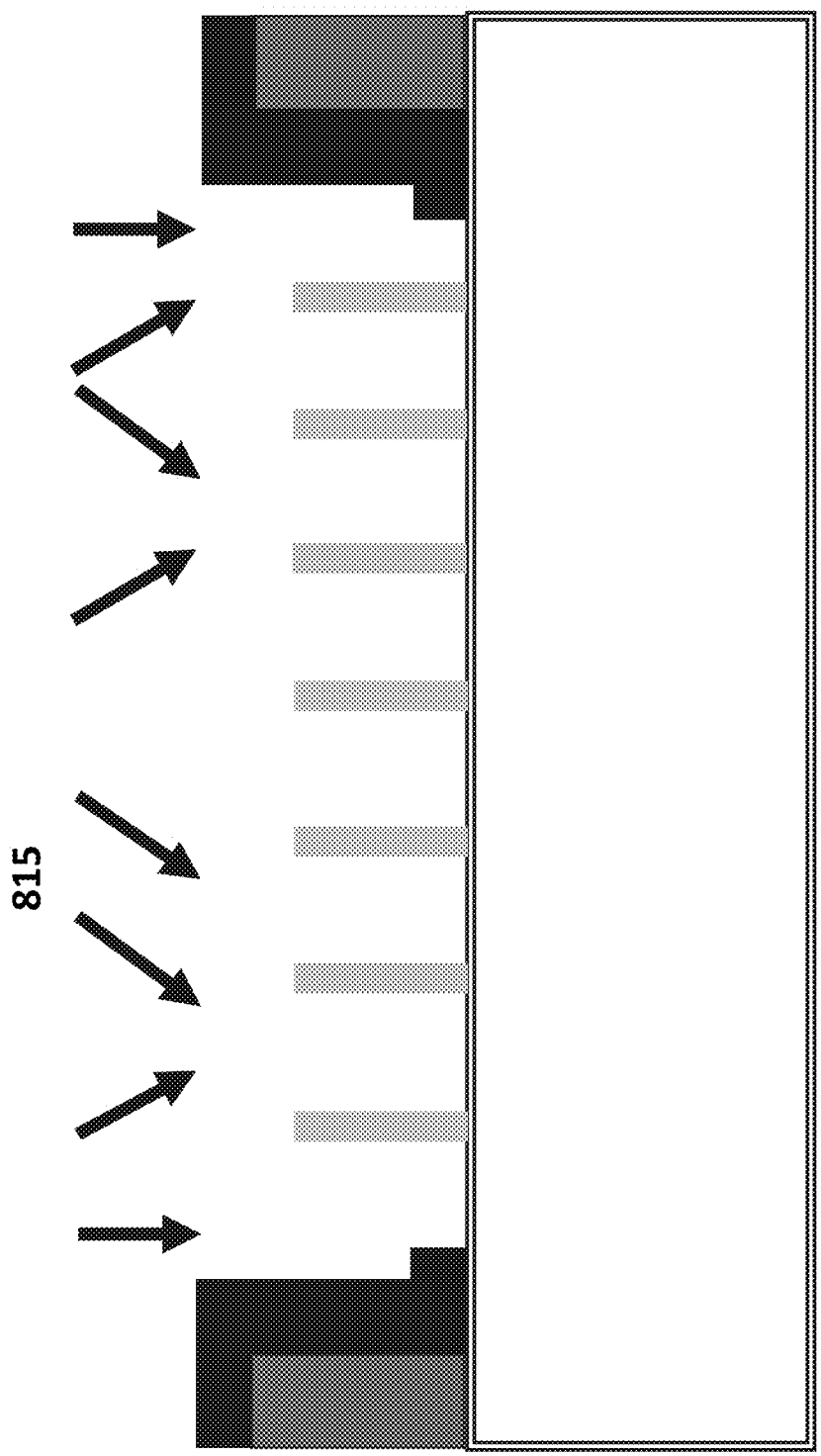

WIRELESS SENSING PLATFORM FOR MULTI-ANALYTE SENSING

CROSS-REFERENCE TO RELATED APPLICATIONS

This application claims any and all benefits as provided by law including benefit under 35 U.S.C. § 119(e) of the U.S. Provisional Application No. 62/527,525, filed Jun. 30, 2017, the contents of which are incorporated herein by reference in its entirety.

STATEMENT REGARDING FEDERALLY SPONSORED RESEARCH

This invention was made with government support under contract no. R43DK109811-01, and no. R43DK111001-01 awarded by the National Institutes of Health, and contract no. 1621991 awarded by the National Science Foundation. The government has certain rights in the invention.

BACKGROUND

Technical Field of the Invention

The present invention is directed to implantable analyte sensing systems and more specifically to a low-cost, wireless, multi-analyte sensing platform including an implantable biocompatible sensor, a wireless transceiver, and a smart data analysis platform.

Description of the Prior Art

Continuous monitoring of personal health can revolutionize healthcare by enabling preventative health management compared to the traditional treatment based healthcare model. The preventative healthcare model can utilize continuous monitoring of health indicators to improve the quality of care as compared to the traditional model that relies on a few measurements at discrete points in time.

Continuous monitoring of health requires new tools and technologies. There are some health monitoring devices currently being used; Cardiovascular monitoring (e.g. pacemakers) and metabolic monitoring (e.g. glucose monitoring) are two main applications of such monitoring devices. For example, Continuous Glucose Monitoring (CGM) systems from Medtronic and Dexcom are available for continuous glucose monitoring for diabetes patients.

However, large scale use of continuous monitoring platforms requires fundamentally new technologies. For example, less than 10% of patients currently use the CGM systems although it has been shown to be the best method for diabetes management. The disadvantages of the current technologies include their high complexity, large size and high cost. These macro (from few cm to few mm) scale devices need special implantation procedures, are prone to rejection by the body due to the immune system response, need bulky power supply systems which have a limited battery life, and have high manufacturing costs associated with utilizing and integrating discrete components.

SUMMARY

In accordance with the present invention, a platform based system for in-vivo multi-analyte monitoring is disclosed. The platform includes an extremely small size wireless implantable sensor enabling continuous monitoring and resulting in increased value for chronic applications due to minimal foreign body response. The components of the system can be fabricated at minimized cost by utilizing standard and scalable materials and manufacturing methods (e.g., conventional integrated circuit fabrication methods).

Lithographically integrated systems allow extreme miniaturization and can be used to produce extremely small sensors in accordance with the invention. CMOS based sensors have been proposed in other works [1]. In accordance with some embodiments of the invention, herein is presented a complete wireless health monitoring platform using a dynamic design to provide the reliability, yield and performance specifications required for clinical applications while managing environment variations and regulatory requirements. Furthermore, the presented design can be completely integrated on a unitary semiconductor platform and can provide advantages over other sensing platforms that consist of several different components to be bonded together [2], [3] in a complicated and failure-prone manner.

Some advantages of the invention presented here as compared to prior art include: (i) disclosure of a complete wireless sensing platform with design of all system components, (ii) disclosure of an integrated sensing element in close proximity to potentiostat and signal processing circuit (iii) disclosure of a dynamic, adaptively matched wireless powering and communication scheme that allows for reliable operation, (iv) disclosure of a dynamic control circuit design that keeps sensor measurement range at an optimal level throughout operation, (v) the use of standard wireless communication protocols that minimizes error rates, (vi) the use of patterned electrodes (e.g., patterned during semiconductor fabrication) that provide for higher sensor sensitivity, yield, reliability, and (vii) the use of custom functionalization methods, and processing to achieve high yield for volume production of sensors.

For applications where the component materials of the design are not available in standard semiconductor processes (for example, gold electrodes aren't available in standard semiconductor processes but are useful for some medical applications), lithographic post-processing can be used at the wafer level (at the end or after the standard fabrication process) to complete the fabrication of the device. This can reduce the cost of such process and also makes the handling much easier.

In accordance with some embodiments of the system, the wireless sensing system can include a sensor (e.g., placed subcutaneously or under the skin and in contact with tissue containing one or more analyte), an external transceiver (e.g., to power and/or communicate with the implanted sensor and communicate with the reader), a reader (e.g., to receive analyte sensing data from the transceiver and send the data to the cloud) and the cloud storage & processing to provide feedback to the user and to their caregiver/doctor. The system can thereby provide information such as an analyte concentration, in a tissue (e.g., in an organ, vessel or fluids surrounding tissues and organs).

The present invention is directed to a wireless system for continuous monitoring of one or more health indicators. The system can include a wireless sensor (e.g., an implantable wireless sensor component) configured for analyzing one or more analytes in vivo, a wireless transceiver for receiving wireless data signals from the wireless sensor and transmitting the data signals to a remote server over a network. The analyte can include one or more biomarkers, such as blood glucose, enabling continuous monitoring of blood glucose levels.

Wireless monitoring of one or more health or biological markers in a continuous manner can be used to enable customized monitoring and therapies (e.g., personalized medicine). This will reduce healthcare cost and complexity and improve outcomes. The present invention is directed to a wireless multi-analyte sensing system. In accordance with some embodiments of the invention, the system can include an implantable sensor, an external wireless transceiver, a wireless reader, a smart data processing and communication system, an injecting device and an extracting device and methods for making and using the same.

In accordance with some embodiments of the invention, the system can include an implantable wireless sensor. The sensor can be made using different technologies. In one embodiment, the sensor can include a microchip (e.g., an integrated circuit) having of an electronic circuit connected to one or more type of sensing elements (e.g., electrodes or electrochemical sensor elements) and with one or more wireless power transfer and wireless telemetry components. For example, the sensor can wirelessly receive power and use the power to energize the sensing circuitry and one or more sensing elements and send wireless data to a remote device, such as using radio frequency identification (RFID) or near-field communication (NFC) technology. In accordance with some embodiments of the invention, wireless power harvesting and wireless telemetry can be provided using high frequency electromagnetic waves with frequency range of about 10 MHz to 1 THz (e.g., 800 MHz to 6 GHz).

The sensor can be configured to work with an external transceiver in order to receive energy for its operation and also to wirelessly communicate sensor data to the transceiver and the other remote systems. The transceiver can include power transfer and data telemetry components. The actual nature of these components depends upon the type of application and the nature of wireless sensor. An example of the wireless transceiver with different components is shown in FIG. 3.

In accordance with some embodiments of the invention, the transceiver can relay the data to a smart personal device, such as a hub or smartphone, which provides a better display as well as for setting up personalized alarms and other long term data analysis and feedback tools, via a cloud based intelligent platform consisting of smart algorithms and feedback from caregivers. In accordance with some embodiments of the invention, the transceiver can relay the data to a hub such as a computerized transceiver, which can provide for personalized alarms and for transferring the data to a local server or a cloud based server. Either server can provide long term data analysis and feedback tools, via a server or cloud based intelligent platform consisting of smart algorithms and feedback from caregivers. In accordance with some embodiments of the invention, the transceiver can relay the data directly to a local server or a cloud based server. Either server can provide long term data analysis and feedback tools, via a server or cloud based intelligent platform consisting of smart algorithms and feedback from caregivers.

The system can also include a device configured to implant or embed the sensor in its environment. For example, for applications inside the body, the device can include an injector to lodge the device at its appropriate sensing position in the body. In one particular embodiment, this can be an injector to embed the sensor under the skin for measurements and analysis of fluids in the tissue.

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

FIG. 4B and FIG. 4C show schematic detailed views of two embodiments of the on-chip resonant unit 110 according to some embodiments of the invention. In FIG. 4B the switching mechanism includes a switch 155. In FIG. 4C the switching mechanism includes a capacitor 156 and a switch 157.

FIG. 5A shows a plot exemplifying a tuned voltage response ($V_{tune}$) to frequency as the tunable capacitor 314 changes its capacitance value based on a tuning algorithm. FIG. 5B shows the voltage response ($V_{tune}$) to the tunable capacitor 314 value at a fixed frequency (the 0.9 GHz frequency showing the maximum voltage in FIG. 5A). FIG. 5C shows a circuit with an AC voltage (e.g. on transceiver side) that is inductively coupled to a circuit for a tuned voltage output ($V_{tune}$) (e.g. on receiver i.e. implant side). FIGS. 5C and 5D show that the coupled circuits include digitally tunable capacitors 313 and 314 whose values are adjusted based upon the output from tuning algorithm. FIG. 5E shows the relationships between frequency of the circuit of FIG. 5C ($f_{r1}$) and its components (inductor $L_1$, capacitor $C_1$=313), and the frequency of the circuit of FIG. 5D ($f_{r2}$) and its components (inductor $L_2$, capacitor $C_2$=314).

FIG. 17A-E shows process steps to coat the integrated sensing element electrodes with thin metal films, using one particular method of lithographic processing. A starting device containing multiple pillar-like structures is fabricated using a semiconductor fabrication process (FIG. 17A). In one example, these pillars can be fabricated in the thick Aluminum metal (810) of the top metal layer of the Metal-Insulator-Metal (MIM) structure (812) found in CMOS devices. This structure normally resides above a Silicon substrate (813). Several electrodes can be isolated from each other by top insulation (811) (Top insulation in CMOS process is typically a stack of Silicon Nitride layer on top of Silicon oxide layer. Top insulation can be further augmented by an additional layer (e.g. Polyimide layer) (611). The device is first patterned using lithography to create patterned photoresist (814) as seen FIG. 17B. Device is then coated with a thin layer of desired material (e.g. Platinum) (815) using a thin-film coating method, for example electron beam deposition or sputtering as depicted by FIG. 17C and FIG. 17D. The device is then cleaned to remove excess deposited material and leave it in desired places (e.g. on integrated sensing element electrodes) only as shown in FIG. 17E.

FIG. 26A is an embodiment of a process flow with dicing before functionalization. FIG. 26B is an embodiment of a process flow with functionalization before dicing. Either one of these processes, or a hybrid process where the devices are partially separated in an intermediate step (e.g. scribing the surface (e.g., mechanically or with a laser), stealth dicing) and separated afterwards, can generate functional devices.

FIGS. 29, 30 and 31 shows the operation of the injector assembly to embed the sensor (1) in desired location under the skin. The first step is insertion of the needle under the skin (FIG. 29), second steps is to retract the needle exposing the parts 1002 and/or 1004 under the skin (FIG. 30), third step is to retract entire assembly resulting in sensor dislodging under the skin (FIG. 31).

DETAILED DESCRIPTION

The present invention is directed to a sensing platform that can be used in a variety of in-vitro, ex-vivo and in-vivo applications providing continuous measurement of one or more types of health or biological markers (e.g., metabolites and/or analytes). For purposes of illustration and without loss of generality, in-vivo electrochemical measurement of one or more analytes are referred to in this example. As a person having ordinary skill in the art will appreciate, the described devices, systems and methods can be more generally applied to other analyte and sensing modalities; including but not limited to wired sensors; sensors with power storage capability, sensors powered with other modalities such as those described elsewhere in this document, industrial sensors; sensors comprising optical, capacitive, or mechanical sensing elements; physical measurements such as temperature, vibration, pressure, light, electromagnetic radiation, or sound of any frequency including but not limited to ultrasound and megasound.

Figure 1:
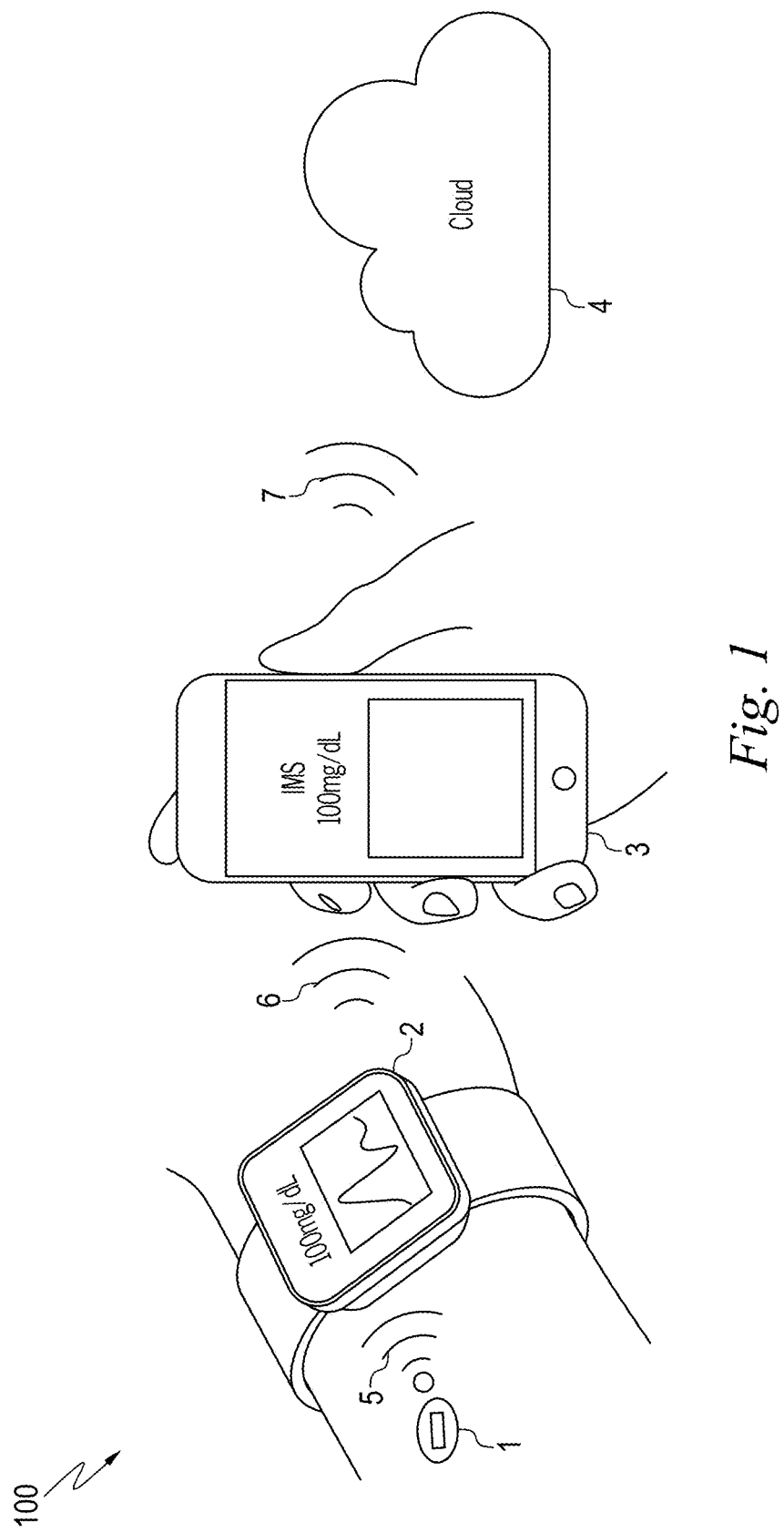
FIG. 1 shows a diagrammatic view of a system according to some embodiments of the invention, including a sensor 1 connected by wireless connection 5 to a transceiver 2, the transceiver 2 connected by wireless connection 6 to a communication device 3 which can be connected by a network 7 to a remote server (e.g. a cloud server) 4.

FIG. 1 shows a diagrammatic view of a system 100 according to some embodiments of the invention. The system 100 can include a sensor 1, an external transceiver 2 adapted to be positioned sufficiently near the sensor 1 to enable the transceiver 2 to provide power the sensor 1. The sensor 1 can be wirelessly connected to transceiver 2 using a wireless communication and/or power technology 5 such as radio frequency ID (RFIC), near field communication (NFC) or any other wireless protocol or technology. The transceiver 2 can produce an electromagnetic field that induces a current to flow in a component a coil) of the sensor 1 enabling the sensor 1 to power up. The transceiver 2 can provide power to the sensor 1 and the sensor 1 can send sensor data to the transceiver 2. Transceiver 2 can be wirelessly connected to communication device 3 (e.g., a computer hub or smart phone) using a wireless communication technology such as Blue tooth or WiFi. The transceiver 2 can send sensor data to the communication device 3.

Figure 2:
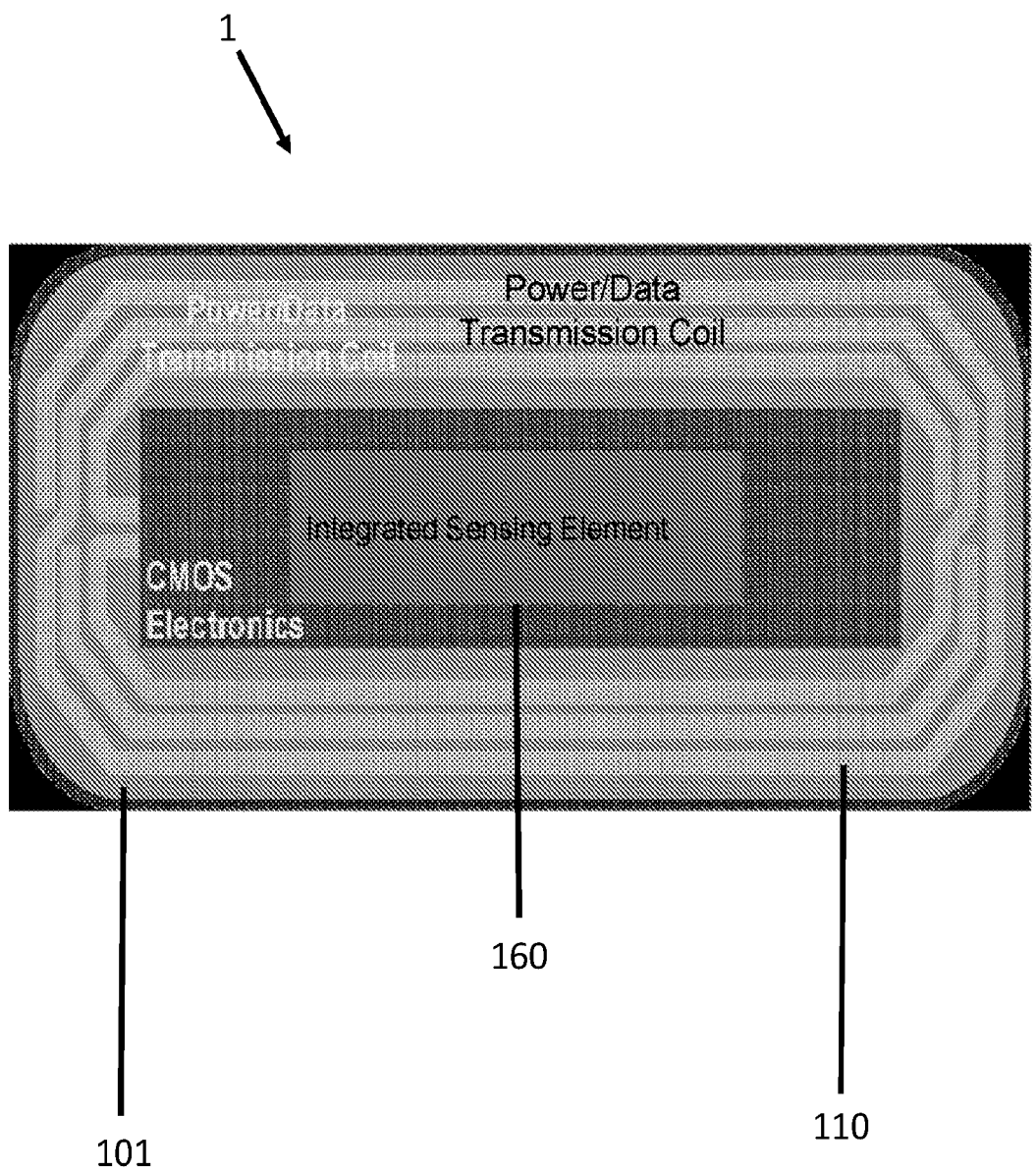
FIG. 2 shows a diagrammatic view of a sensor 1 according to some embodiments of the invention. Sensor 1 can include an integrated electronics platform 101, a wireless powering/communication system including an on-chip LC resonant unit 110, and an integrated sensing element 160.

As an example, when the transceiver 2 is turned on, it detects the region of operation (e.g. US or EU) through user input and/or geo-location, and selects the frequency range of operation based upon the region. Then it selects appropriate value of variable capacitors to select this frequency. At that point, it measures the reflected power and fine tunes the capacitor value (Digitally Tunable Capacitor) to minimize reflected power from the antenna to maximize the power transmitted out to the sensor 1. Upon receiving power, the sensor 1 powers up and starts sensing one or more analytes in the tissue. The sensor 1 also can be configured to transmit sensor data to the external transceiver 2, for example, using NIT. As an example, upon receiving power, the sensor 1 rectifies the electromagnetic power and filters it to generate a stable DC voltage. It then compares the voltage level of this source with a reference value to determine if the power is sufficient to correctly operate the implanted sensor. If it is, it moves to the next step. If not, it adjusts the on-chip capacitor value to match its resonant frequency to that of the external transmitter, until the received power level is sufficient to correctly operate all subsystems of the sensor 1. Then the chip sends the DC power to the potentiostat which powers up the integrated sensing element 160 (FIG. 2). The integrated sensing element in response detects the analyte of interest (e.g. Glucose) based upon its surface chemistry and potentiostat settings and generates a current reading proportional to the concentration of analyte. The current is converted to a voltage reading using an op-amp with capacitive feedback and the voltage reading is sent to an Analog-to-Digital converter (ADC). If a read command is received from the external transceiver, the ADC sends the digital reading to the transmit unit which sends the data via a backscattered telemetry scheme to the external transceiver. The external transceiver 2 can receive sensor data from the sensor 1 and transmit the sensor data to the optional communication device 3 (e.g., a smartphone or hub) which can be adapted and/or configured to communicate the sensor data to and receive data from a remote server 4 (e.g. a cloud server). The remote server 4 can include analytics software that analyzes the sensor data and sends instructions or information back to the communication device 3, to inform the user of the user's condition.

Figure 3:
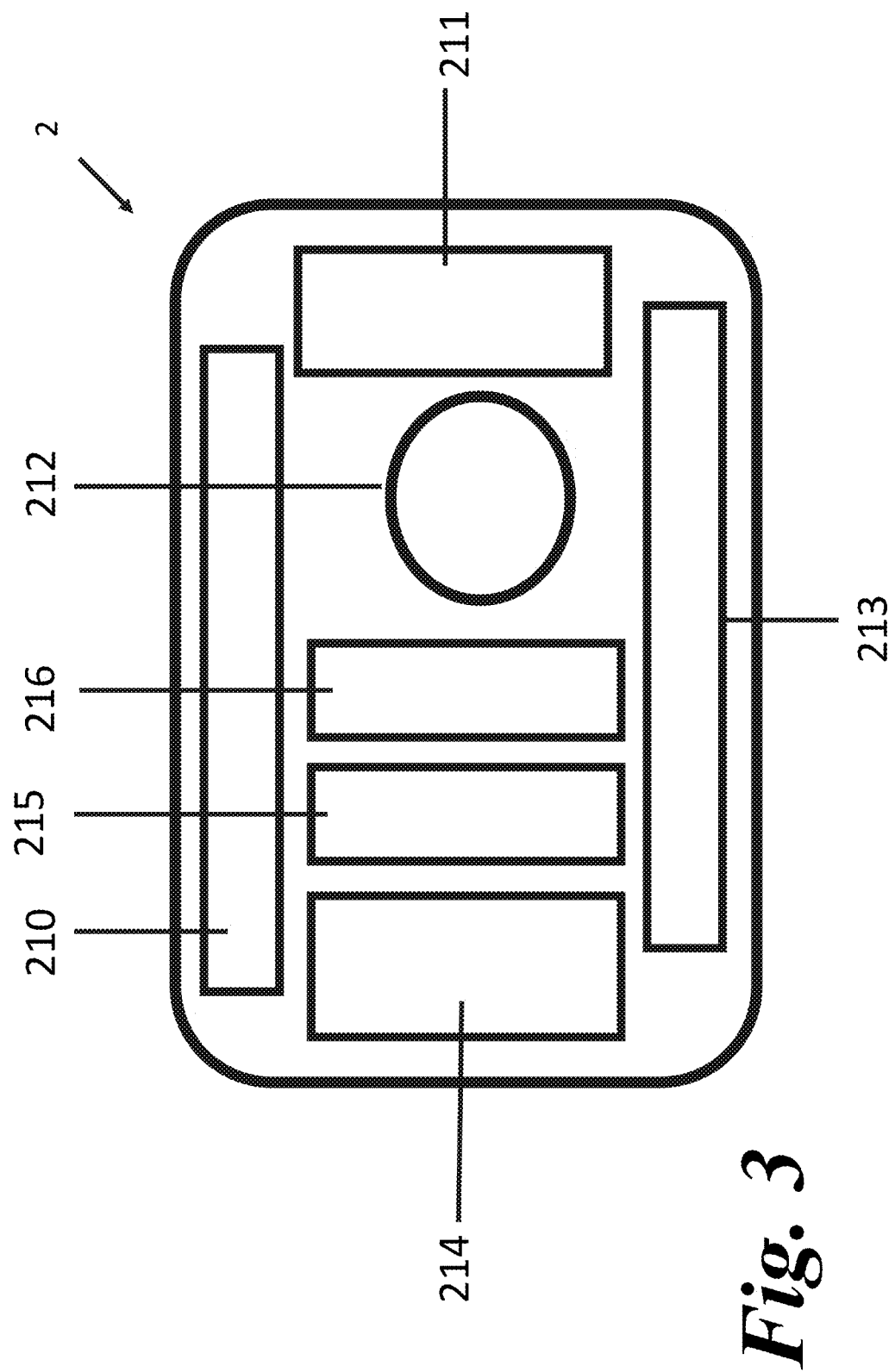
FIG. 3 shows a high-level schematic of the wireless transceiver 2 according to some embodiments of the invention. The transceiver 2 can include a signal generator 210 (e.g. Ultra-High Frequency (UHF) Chip that can generate and detect high-frequency wireless signals e.g. those in ISM band at 900 MHz), a high-performance digital microprocessor unit 211, a transducer 212) (e.g. an antenna or coil or a microlaser), a low-energy wireless communication chipset 213 (e.g. Bluetooth), a power management unit 214 consisting of a rechargeable battery and required circuitry, a low-power display 215, and other sensors and actuator units 216 (e.g. an accelerometer and a buzzer).

FIG. 2 shows a diagrammatic view of a sensor 1 that can be embodied in an implantable integrated circuit chip according to some embodiments of the invention. The sensor 1 can include an integrated electronics platform (101), a wireless powering/communication system including an on-chip LC resonant unit 110, and one or more sensing elements 160, FIG. 3 shows a diagrammatic view of the wireless transceiver 2 adapted to provide power to the sensor 1 and/or to receive data from or transmit data to the sensor 1. The transceiver 2 can include a signal generator 210 (e.g. Ultra-High Frequency (UHF) Chip) that can generate and detect high-frequency wireless signals (e.g. those in ISM band at 900 MHz), a digital microprocessor unit 211 (e.g., an ARM based processor or an Intel processor and associated memory), a transducer 212 (e.g. an antenna or coil or a microlaser), a wireless communication chipset 213 (e.g. Bluetooth, ANT, WiFi, and ZigBee), a power management unit 214 consisting of a rechargeable battery and circuitry to control charging and/or discharging the rechargeable battery, an optional low-power display 215, and other sensors and actuator units 216 (e.g. an accelerometer and/or a buzzer). The Sensor In accordance with some embodiments of the invention, the system 100 can include one or more sensors that can detect and measure the presence of one or more analyte of interest in tissue fluid. The sensor can include, for example, an integrated circuit chip fabricated using integrated circuit fabrication technologies known to the person skilled in the art of making functional sensing units. This sensor can include many interconnected functional modules or subsystems and can be in a range from 30 microns to 600 microns in thickness (e.g., 50 microns to 150 microns), 500 microns to 10,000 microns in length (e.g., 1500 microns to 3000 microns) and in a range from 200 microns to 4,000 microns in width (e.g., 400 microns to 1000 microns).

Figure 4A:
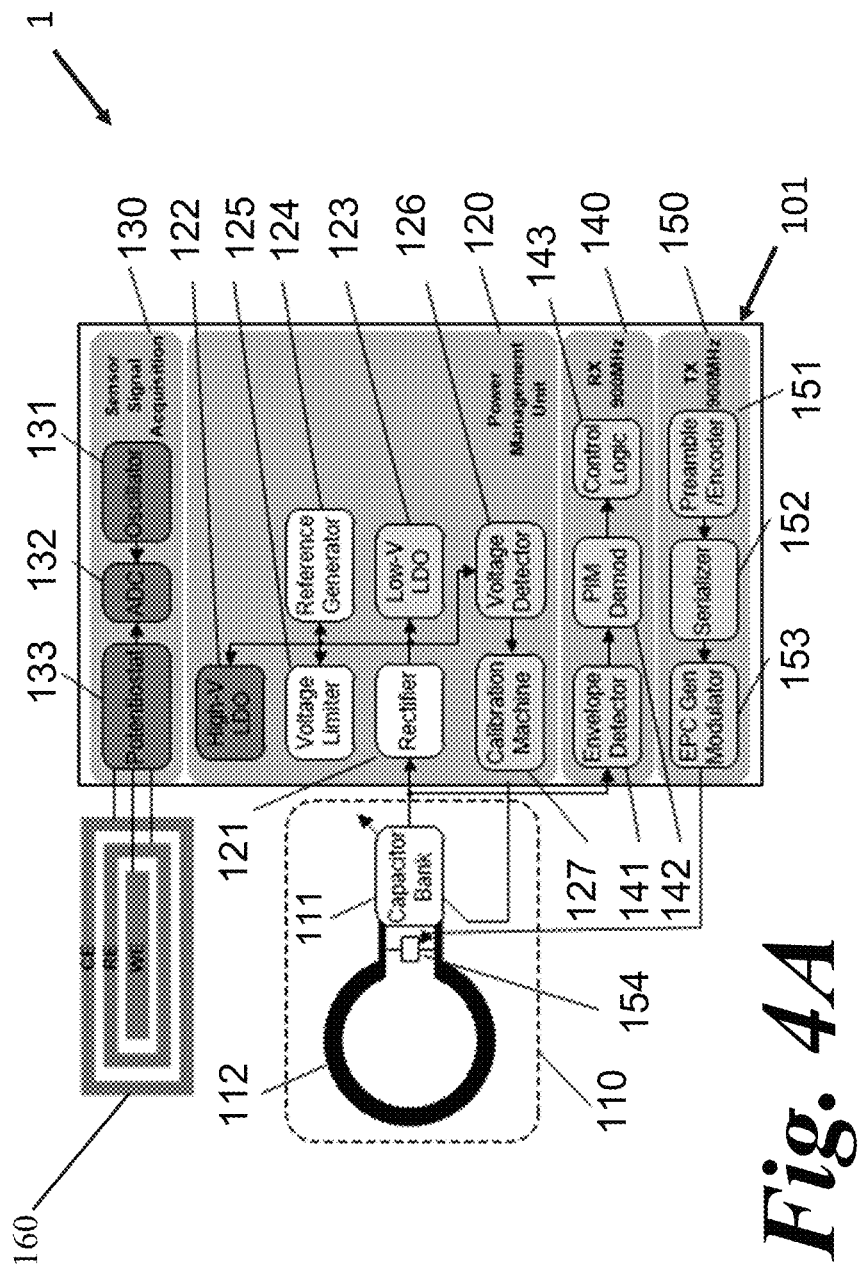
FIG. 4A shows a schematic of the components of the sensor 1 according to some embodiments of the invention. The sensor 1 can include at least one on-chip LC resonant unit 110, a power management unit (120), a signal acquisition and processing unit (130), a Signal Receiver Unit (140), a Signal Transmitter unit (150), and an integrated sensing element (160).

In some embodiments of the invention, the sensor 1 can include an integrated system consisting of an integrated electronics platform 101 and an integrated sensing element 160. The sensor 1 can further include on-chip LC resonant unit 110. The integrated electronics platform 101 can further contain a power management unit 120, a signal acquisition and processing unit 130, a receiver unit 140, and a transmitter unit 150. A diagram of an example of an implantable electrochemical sensing device according to some embodiments of the invention is shown in FIG. 4A.

The on-chip LC resonant unit 110 can include an antenna coil 112 for receiving power and data signals from a remote device and a capacitor bank 111 which forms an LC resonant system that couples to an antenna of the external transceiver 2 to enable the transfer of power and data between the external transceiver 2 and the sensor 1.

In accordance with some embodiments of the invention, the electronics platform (101) can include a receiver subsystem 140 and transmission subsystem 150. The receiver subsystem 140 can comprise an envelope detector 141, PIM Decoder 142, and Control Logic 143. The transmission subsystem 150 can include a preamble/encoder 151, a serializer 152, and an EPC Gen Modulator 153.

In the receiver subsystem 140, the envelope detector 141 can be used to extract the data transmitted from the external transceiver in the form of amplitude modulation of the UHF 900 MHz RF power signal. The PIM decoder 142 decodes the received signal which includes the activation tag for the implant as well as the sensor current measurement range. The transmitted data from the external transceiver 2 can be in the form of pulse interval coding. The control logic 143 can perform signal conditioning and interpretation of the received data from the external transceiver 2.

In the transmission subsystem 150, the preamble/encoder 151 combines the sensor data into one or more packets that can be sent to the external transceiver. The packetized data can include the sensor measured data, power calibration data, over/under power indicator data and/or the capacitor bank value. The preamble/encoder 151 can combine all of these data elements into a single data packet and add a preamble sequence at the beginning of the data packet for the ease of detection by the external transceiver 2 (e.g., in accordance with the EPC GEN II communication protocol). The Serializer 152 serializes the data packet received from the preamble/'encoder 151. The EPC GEN modulator 153 can receive and convert the serialized data packets into FM0 or Manchester encoded signals (for transmission to the external transceiver 2) and can, optionally, add error correcting sequences (e.g., cyclic redundancy check, CRC) for immunity to communication and detection noise (in accordance with the EPC GEN II communication protocol).

The power management unit 120 can include a rectifier 121, high voltage low dropout regulator (e.g., high-V LDO regulator) 122, low voltage low dropout regulator (e.g., low V-LDO regulator) 123, reference generator 124, voltage limiter 125, voltage detector 126, calibration machine 127.

The rectifier 121 converts the RF power signal (received from the external transceiver 2) into a DC voltage to supply power the sensor 1. The rectifier 121 can be connected to on-chip LC resonant unit 110 and the capacitor bank 111 of the on-chip LC resonant unit (110). The capacitor bank 111 can be used to store electrical energy to power the sensor 1.

The low-V-LDO regulator 123 can include a low-dropout regulator that regulates the rectifier low voltage output into a clean DC voltage (without ripples existing in the rectifier output). The low-voltage-LDO supplies the calibration engine and the digital circuitry that run at a low supply voltage (0.6V-0.8V). The low-V-LDO can be connected to the rectifier 121.

The high-V LDO can include a low-dropout regulator that regulates the rectifier high voltage output into a clean DC voltage (e.g., without ripples existing in the rectifier output). The high-V-LDO can supply 1.0-1.2V to the signal acquisition and processing unit 130 (e.g., an analog to digital converter (ADC)), potentiostat, and the oscillator of the signal acquisition and processing unit 130.

The reference generator 124 generates the reference voltages and currents used by the signal acquisition and processing unit 130 (e.g., an ADC), a potentiostat, and the oscillator of the signal acquisition and processing unit 130. The reference generator 124 can provide high power supply rejection to eliminate sensitivity to rectifier ripples.

The voltage limiter 125 can be used to measure the output of the rectifier and determine whether the implant is underpowered, properly powered, or overpowered, and reports the power data to the external transceiver as part of the data packet. In the case of over power, it protects the system from over-voltage stress by sinking more current and hence reducing the rectifier voltage.

The voltage detector 126 can be used to monitor the rectifier voltage and provide this data to the calibration machine 127 to maximize power transfer efficiency by maximizing the output voltage from the rectifier 121. This can be accomplished, for example, by adjusting the capacitor bank value (e.g., capacitance) of the on-chip LC resonant unit 110 and achieving close to perfect matching between the sensor 1 resonant frequency and that of the external transceiver 2.

The calibration machine 127 can include a digital finite state machine that employs the voltage detector 126 output to maximize power transfer efficiency. Optimal power transfer happens when the voltage at the output of the rectifier (121) is enough to operate the implant, any voltage more than this would be overpowering and hence reducing external devices battery life and any voltage below this level would be underpowering which results in implant malfunction. Voltage detector measures the rectifier voltage and includes that into each data packet sent out to the external device. If the voltage is less than minimum required for the operation of the implant, the external device increases the transmitted power level. If the voltage is more than required voltage for the operation of the implant, the external device reduces the transmitted power to minimize external device's power consumption.

The signal acquisition and processing unit 130 can include an oscillator 131, a potentiostat 133, and an analog to digital converter (ADC) 132.

The oscillator 131 can be used to provide an accurate and clean reference clock for the implant that is used both by the transmission systems 150 and the signal acquisition and processing unit 130.

Figure 12:
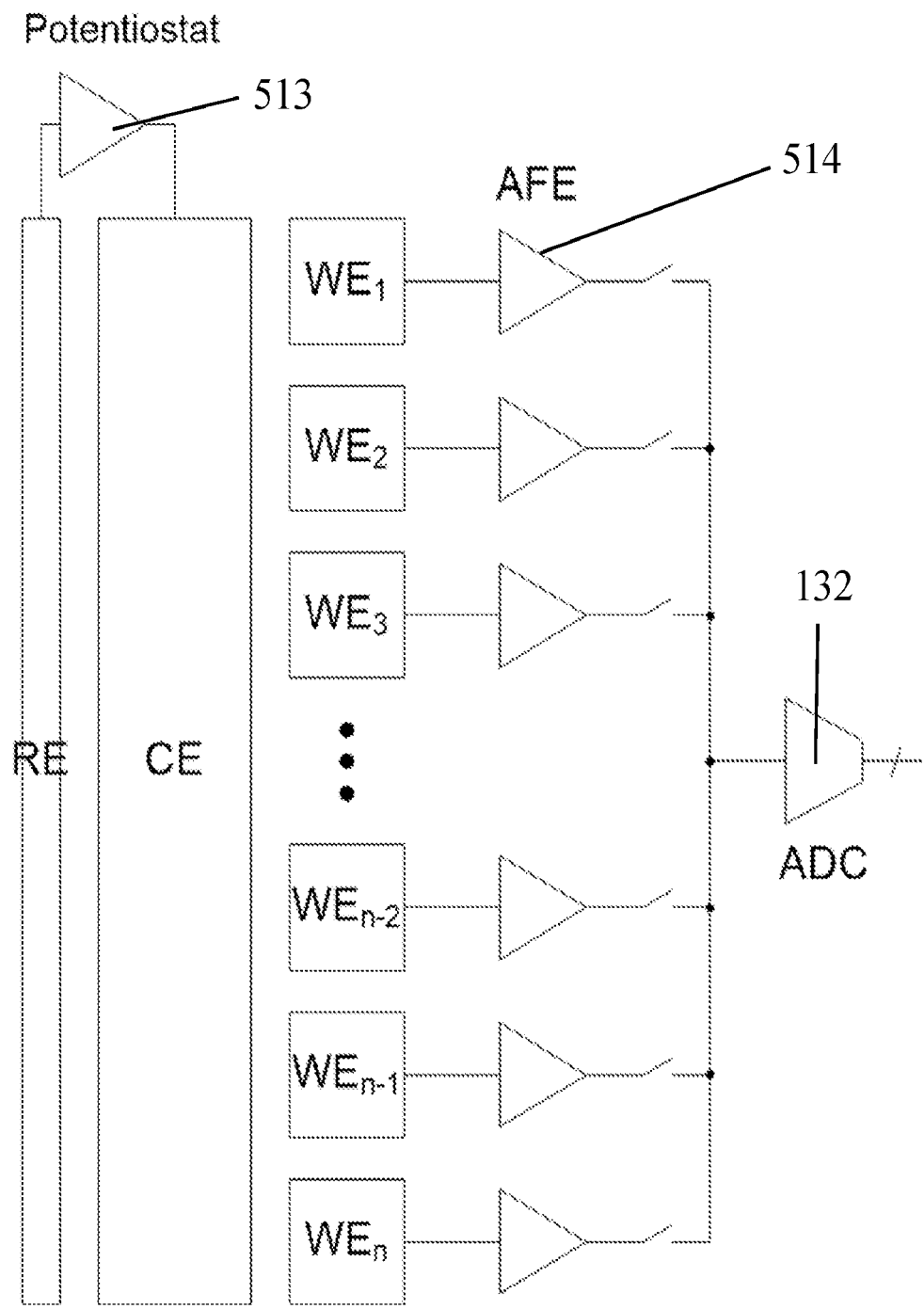
FIG. 12 describes Multi-analyte sensing circuitry using minimal chip area through time multiplexing and sharing of counter and reference electrodes and respective circuitry. Dedicated working electrodes and analog front-end (AFE) are used for each analyte.
Figure 15A:
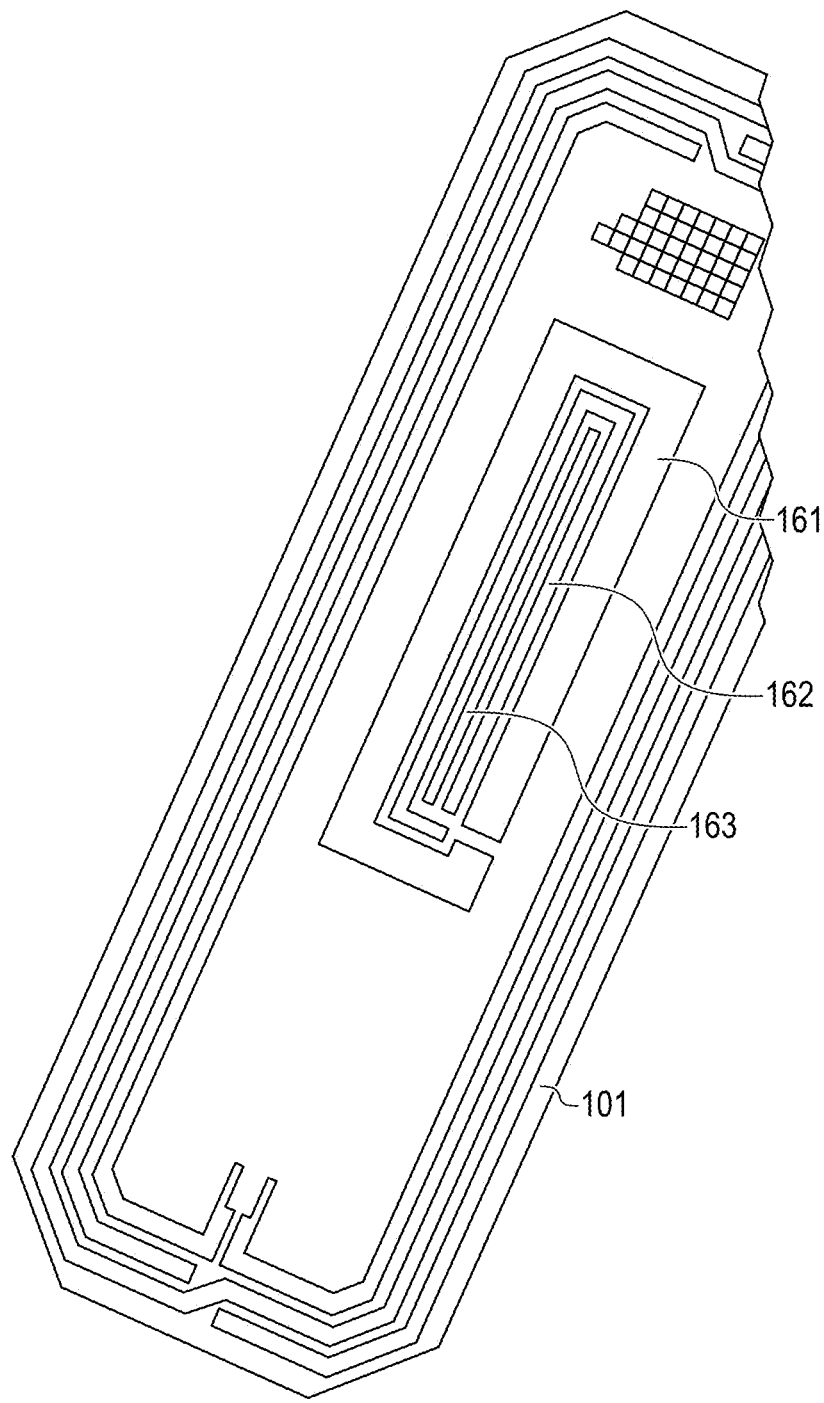
FIG. 15A is a picture of an embodiment of an integrated sensing element (160). This sensing element can consist of 3 electrodes; a Counter Electrode i.e. CE (161), a Working Electrode i.e. WE (162) and a Reference Electrode i.e. RE (163). These integrated electrodes as sensing elements result in sensor having superior performance compared to discrete sensing elements bonded to discrete electronics.

As shown in FIGS. 11A, 11B and 12, the potentiostat 132 can be connected to the sensing element 160 and control the sensing element electrode voltages while measuring the resulting current from the sensing element 160. The potentiostat 132 maintains a fixed defined voltage between the working (WE) 162 and reference electrode (RE) 163 while providing current through the counter electrode (CE) 161 as shown in FIG. 15A. This is done through a negative feedback architecture utilizing an operational amplifier 512 whose two inputs are connected to the reference electrode (RE)163 and a fixed voltage source while counter electrode (CE) 161 is connected to its output. Another operational amplifier 511 in a negative feedback configuration can be used to set the working electrode (WE) 162 voltage.

The ADC 132 can, for example, include an 8-bit ADC that converts the potentiostat current into digital data values. The control logic can optionally add error correction, preamble and data header to the ADC 132 output to create the output data packet. A serializer can be used to send the data packet sequentially to the transmitter and the transmitter can be sued to send the data (e.g., bit by bit) to the transceiver 2.

The sensor 1 can be wirelessly powered from the external transceiver 2 and, once powered, the sensor 1 can then wirelessly communicate with the external transceiver 2. The sensor 1 includes an integrated on-chip LC resonant unit 110 that further contains an antenna 112 that can be dynamically tuned to operate (to receive power and to transmit data) at a particular resonant frequency using a variable on-chip capacitor bank 111.

The antenna converts RF energy received by the antenna to electrical energy that is communicated as a power signal to a power management unit 120. The power management unit 120 can include a rectifier 121 which converts the AC power signal into DC power. In some embodiments, one or more low-pass filters (e.g. a parallel capacitor) can be used to smooth the power signal. In some embodiments, a Low-dropout (LDO) voltage regulator can be used to precisely control the voltage (e.g. 1.8V) that is output by the power management unit 120 into the various circuits of the other functional modules and/or subsystems that make up the sensor (1).

Sensor (1) can include one or more sensors that are used to generate one or more data signals. The quantities and qualities of various parameters of interest can be determined as a function of these one or more data signals. In some embodiments of the invention, the data signals can be combined with other reference and/or stored data signals to generate the quantity and/or quality of parameters of interest. In some embodiments of the invention, the sensor can include an electrochemical integrated sensing element (160) that comprises a working electrode (162) (e.g., a detection reaction can occur at this electrode), a counter electrode (161) (e.g., can be used to balance the current generated by working electrode) and a reference electrode (163) (e.g., to provide a stable voltage reference signal inside the body).

The integrated electronics platform (101) can include a signal acquisition and processing unit 130 which consists of a Potentiostat 132 and an ADC 133. The Potentiostat 132 can include a circuit that controls the operation of the integrated sensing element 160 at a given potential difference between the working and the reference electrodes.

The RX unit 140 can be used to decode the commands/data sent by the transceiver 2 to the sensor (1). The data can be encoded on the RF carrier (e.g. 900 MHz carrier) using a specific modulation scheme (e.g. Pulse Interval modulation (PIM)).

The sensor 1 can also include a TX unit which takes sensor data from the ADC 133, encodes it using a specific modulation scheme (e.g. Manchester coding), add pre-defined sequences (e.g. preambles, pilot sequences) and transmits the encoded data to the external transceiver using either a passive (e.g., backscattering) or an active communication scheme.

In accordance with some embodiments of the invention, the sensor (1) can be wirelessly powered using background or ambient power (e.g., background RF signals, light signals, motion and/or ambient heat or temperature differentials, one or more chemical or biochemical fuel cells) and the TX unit can use a low-power wireless communication scheme (e.g., Bluetooth Low Energy, ANT, Zigbee).

The sensor (1) can be powered using a wireless transceiver 2 that is resonantly coupled to the chip. The wireless transceiver (2) can be battery operated and communicate with the sensor (1) using RFID (or NFC) based passive backscattered communication.

Wireless Power

The sensing system according to the invention can employ wireless powering for long term operation without the need for bulky batteries. Wireless power can be transferred to one system component (e.g., the sensor (1)) from another (e.g., the wireless transceiver (2)) through electromagnetic coupling. For example, continuous remote wireless powering can be provided through electromagnetic field coupling between the external transceiver (2) coil and an on-chip coil on the sensor (1). The on-chip coil can be shaped in many forms but its performance can be affected by shaping requirements for a particular application. External transceiver units (2) can be designed to provide focused power inside the media where these systems are being used (e.g. in human tissue). A Phased-Array design using multiple antenna coils can be used to focus the electromagnetic power. In some embodiments, a combination of magnetic coupling through coils and optical powering through on-chip photoabsorbers can be used for wireless powering. On-chip photoabsorbers can be realized by using semiconductor diodes that are directly exposed (no metal over the diodes) to incoming optical signals from an external light source. In accordance with some embodiments of the invention, wireless power and data transfer can be provided using Radio Frequency IDentification (RFID) based technologies and/or Near Field Communication (NFC) technologies.

In accordance with some embodiments of the invention, an intermediate device can be used to transfer the power from external transceiver (2) to the sensor 1, if the sensor 1 is too deep (e.g. close to deep major arteries, in the intraperitoneal space, inside or near major organs). Given that most of the major arteries are deep, if it is desired to place a sensor in or close to an artery (e.g., for blood analyte, or fat accumulation, LDL or HDL cholesterol), an intermediate device could be used to relay power and/or information. The intermediate device will absorb energy from external source and recreate electromagnetic field that will reach the deeper implant. If an external transceiver (2) is not available, power can also be extracted from background energy (e.g., light, heat, motion and/or vibration, chemical reaction) using a transducer that converts the background energy to electric energy.

In accordance with some embodiments of the invention, special frequencies allowed for such applications (e.g. ISM band) can be used for wireless power and data transfer.

Power management can be provided using integrated circuitry in the integrated electronics platform (101) to regulate and control the power transfer within the system. The integrated circuitry can include on-chip ultra-low voltage drop rectifiers, filters, regulators, etc.

In accordance with some embodiments of the invention, the power transfer system can be configured to operate over a broad range of frequencies. For example, in order to cover the UHF ISM band in different geographic regions the power transfer system can be configured to transfer power using a signal in the frequency range of 865 MHz-928 MHz and the resonant coupling power telemetry can be adaptive. As the resonant coupling operates in a fairly narrow bandwidth (shown in FIG. 5A) there is need for adaptive adjustment of the on-chip resonant frequency that will match that of the external coil to ensure maximum power transfer efficiency.

Operation

Figure 6:
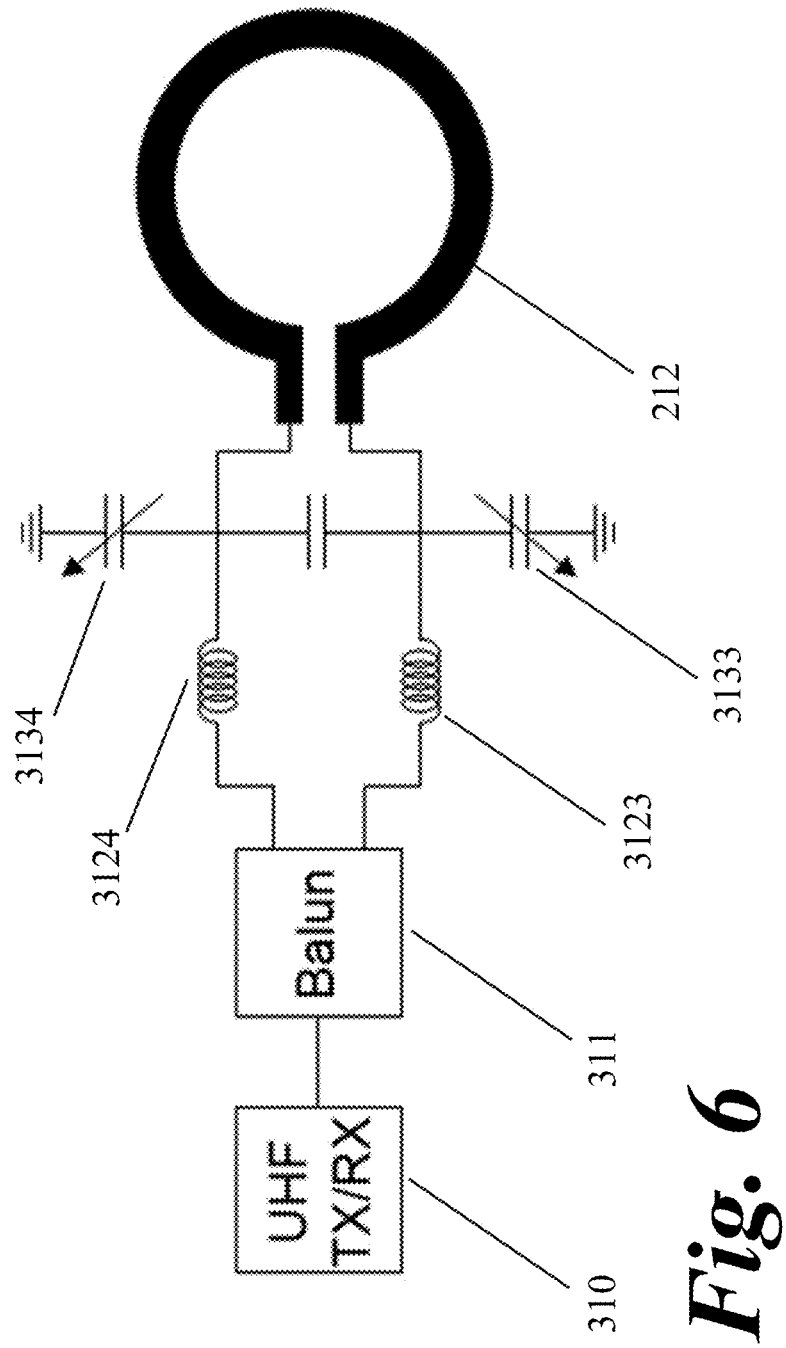
FIG. 6 provides the model for tuning between external transceiver antenna 212 and an on-chip LC resonant unit 110 in the sensor 1 using tenability on the transceiver side using DTCs 3133, 3134. The UHF TX/RX unit 310 generates RF signal (e.g, at 0.9 GHz) that are converted into a two port feed using the Balun 311 via inductors 3123 and 3124. The value of DTCs 3133 and 3134 are adjusted based upon the value of $V_{tune}$. Finally this signal reaches the antenna 212, which creates the electromagnetic field using this signal.
Figure 7:
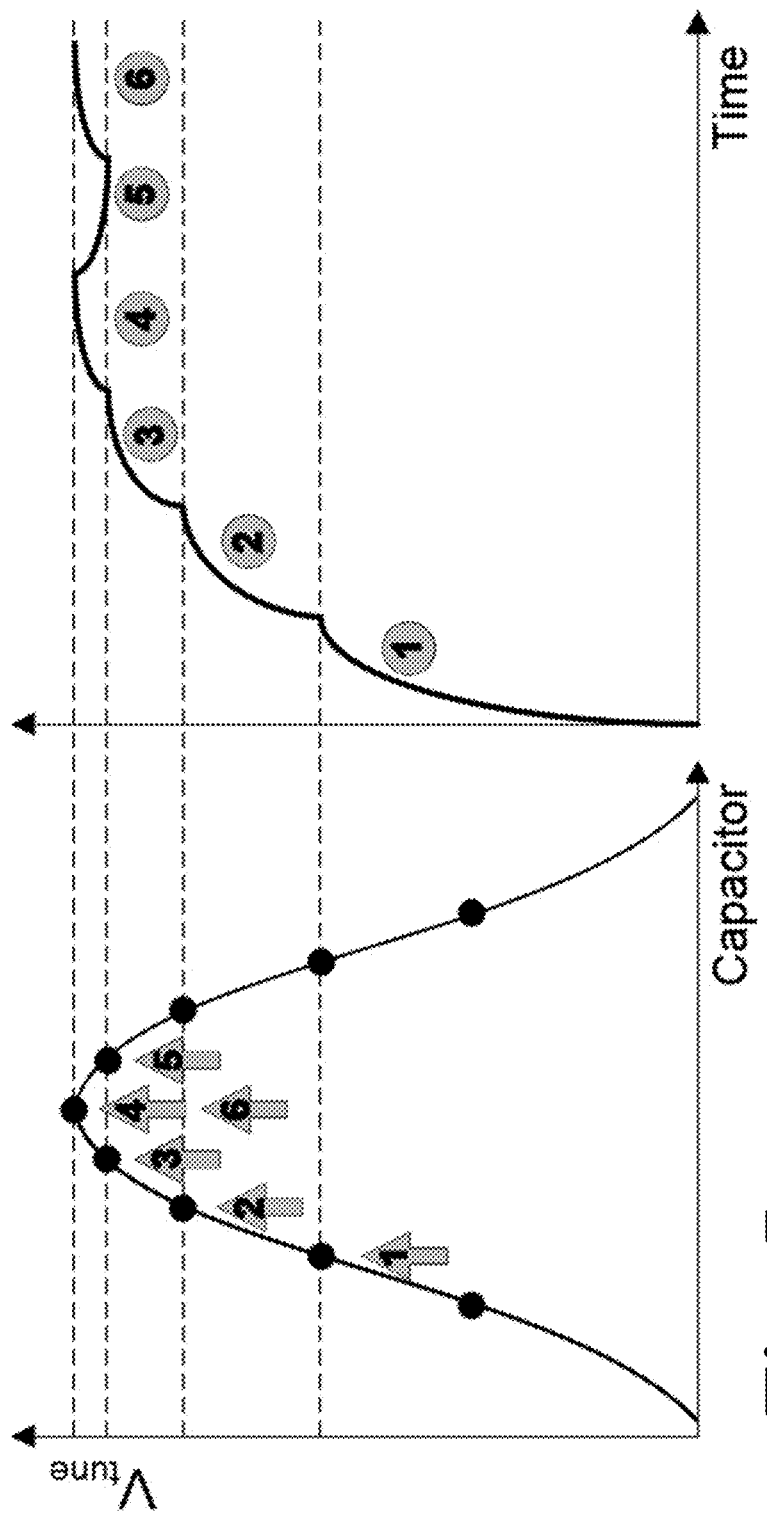
FIG. 7 shows the working of tuning algorithm to choose the capacitor value corresponding to maximum voltage on the receiver side. It also shows the progression in time as the algorithm stabilizes to its optimum value. It shows that the algorithm at startup keeps increasing value of DTC capacitance until it appears that any further increase in capacitance decreases received voltage. As an example, the algorithm may start at a particular value of $V_{tune}$ (represented by dot number '1'). After this, the algorithm increases the value of DTCs 3133 and 3134 which results in a higher value of $V_{tune}$ represented by dot number '2'). The algorithm than moves on and increases the value of DTCs further resulting in points '3', '4' and '5'. When it reaches point '6', it notices that last two increments in DTC values actually resulted in a decrease in $V_{tune}$. This means the value of DTCs that resulted in maximum value of $V_{tune}$ had been achieved and it resets the DTCs to that value (represented by dot number '6').
Figure 8A:
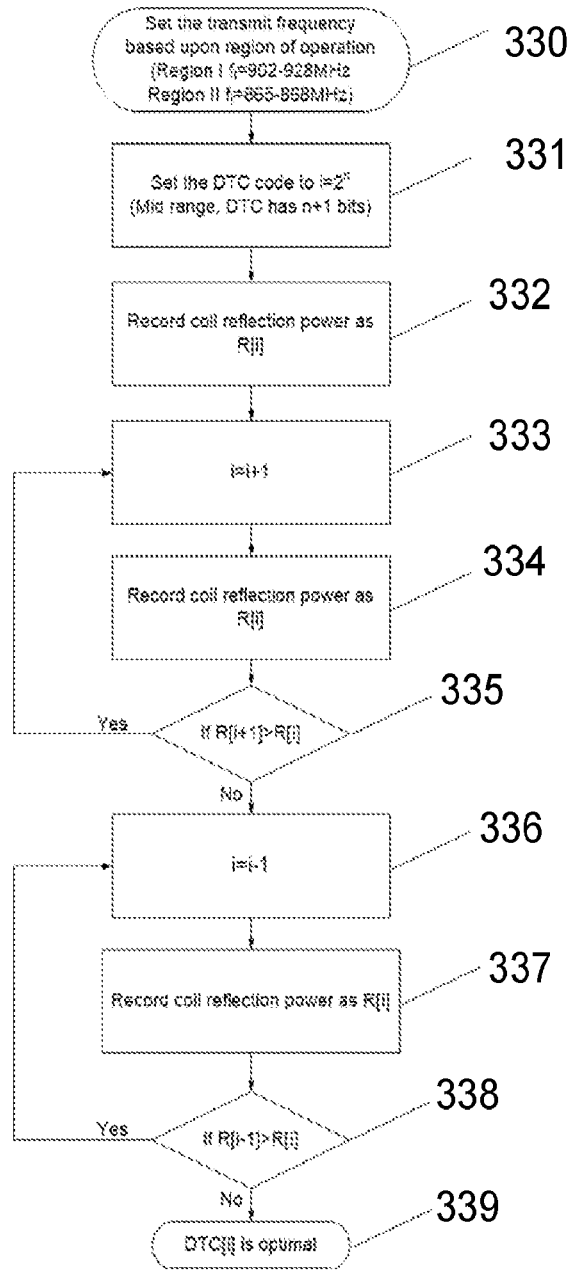
FIGS. 8A and 8B show a flow chart of an adaptive tuning algorithm on transmitter (FIG. 8A) and receiver (FIG. 8B) sides in accordance with some embodiments of the invention. On transmitter side (FIG. 8A), the first step is to set transmitter frequency based upon the region, as indicated by step 330. Next, the algorithm starts with mid-range value of DTC, as indicated by step 331. Then, it measures the reflected power from the antenna, as shown by step 332 Then, it increases the value of DTC in increments (step 333) and measure the reflected power from the antenna (step 334). The algorithm first increases the value of DTC and observes if the reflected power decreases, as indicated by step 335. If not, the algorithm decreases the value of the DTC (step 336), and measures the reflected power (step 337) until a value corresponding to minimum reflected power is achieved, as shown by step 338. The algorithm than decides that optimal reflected power has been achieved, as shown by end point indication at step 339. On the receiver side (chip side) as indicated by FIG. 5B, the algorithm starts the variable capacitor bank in the middle (step 350), and measures the reflected power (step 351). It then increases the capacitor value (step 352) and observes the rectifier voltage (step 353) to determine if the rectifier output voltage increases due to this change (step 354). Then, the algorithm decreases the value of capacitor (step 355), measures rectifier output voltage (step 356) and determines if this has increased the rectifier voltage (step 357). Once maximum rectifier voltage is achieved, optimum capacitor settings have been found and are these values are used, as indicated by end point at step 358.

In accordance with some embodiments of the invention, the sensor 1 can be used to measure glucose levels in the user. The readout procedure for collecting glucose data from the sensor 1 starts with energizing the sensor 1 through transmission of power signal at the allowed UHF frequency ($f_{UHF}$) (865 MHz-928 MHz depending upon the operation region) from the external transceiver 2. The external transceiver 2 can be configured to select the appropriate operating frequency according to the region (e.g., configured using software to control the selection of the operating frequency based on user or clinician input). The resonant frequency of the external reader coil ($f_{r1}$) 914 (FIG. 28) should align with the power signal frequency. This condition will be met by minimizing the reflected power from the coil 914 which is measured and digitized using the UHF transceiver 913. The resonant frequency can be adjusted to tune the external transceiver 913 frequency and the on-chip receiver frequency to maximize wireless power transfer. ISM UHF frequency range can vary from region to region in the world. The resonant frequency of the external transceiver 2 can be adjusted based on the region at which the device is operating. Once the resonant frequency of the external transceiver 2 (master) can be selected based upon the region and the resonance frequency of the implantable sensor 1 (slave) would follow. In some embodiments, for example, the UHF RFID technology can use a frequency in one of two main frequency ranges—902-928 MHz and 865-868 MHz The tuning circuitry in the external transceiver 2 can use a digitally tunable capacitor 3134 in FIG. 6 (e.g., a DTC with n+1 bits, $C_{DTC}=C_{0X}2^{n+1}$) to adjust the resonant frequency ($f_{r1}$). In accordance with some embodiments of the invention, the algorithm can operate as follows:

Based upon the geographical region, the appropriate frequency is chosen (region I, 902 MHz-928 MHz, region II, 865 MHz-868 MHz) as shown by process flow in FIG. 8A (step 330). Once the operating frequency is set (region specific), the DTC value is set to code $i=2^n$ (mid-range) (331). The reflected power from the external device tank is measured (R[i]) by the UHF transceiver (332). The DTC code value is incremented by one unit (i+1) (333) and the reflected power is measured (R[i+1]) (334) and compared with that of previous code (335). If R[i+1] is greater than R[i], increment DTC code by one unit, otherwise decrement DTC by one unit (336) and measure the reflected power from the tank (337) and compare it with previous recording (338). If previous recording (R[i]) is smaller than current (R[i−1]) the optimal DTC code is i (339), otherwise keep decrementing till R[i]<R[i−1]. This gradient search algorithm is shown in FIG. 8A. DTC is a digitally variable capacitor, in case of a 4-bit DTC, the value of DTC is varied by changing the digital control from 0 to $2^4-1=15$, meaning going through 16 possible values of the variable capacitor.

The second step is to adjust the resonant frequency $f_{r2}$ of the implant coil to align with that of the external reader. It is achieved by changing the value of tuning capacitor $C_2$. It should be noted that if the $f_{r1}$ and $f_{r2}$ are too far from each other (For example in FIG. 5A, when $C_2$=1, 1.1, 1.5, 1.6 pF, $f_{r2}$ is not tuned to $f_{r1}$ and hence $V_{tune}$ drops significantly) the power transfer efficiency drops significantly and it might become impossible to energize the implant and hence a temporary boost in the transmitted power might be necessary until the adaptive resonant frequency matching is performed at which time the transmitted power can be reduced to its nominal level.

Figure 8B:
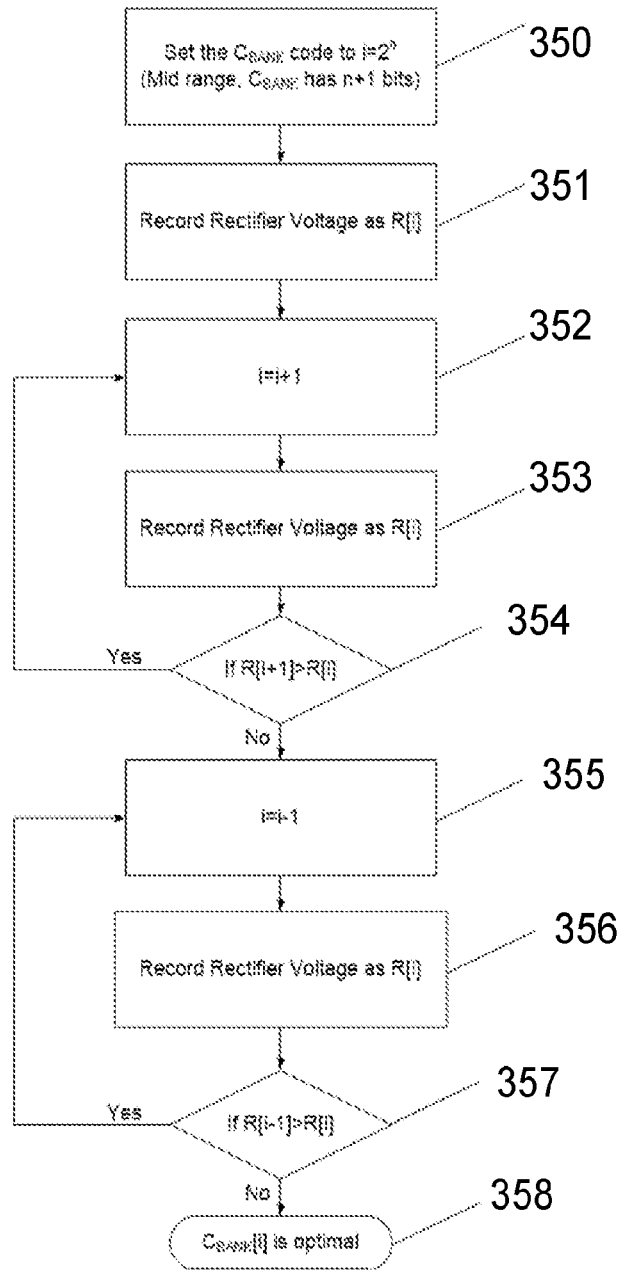
Figure 9:
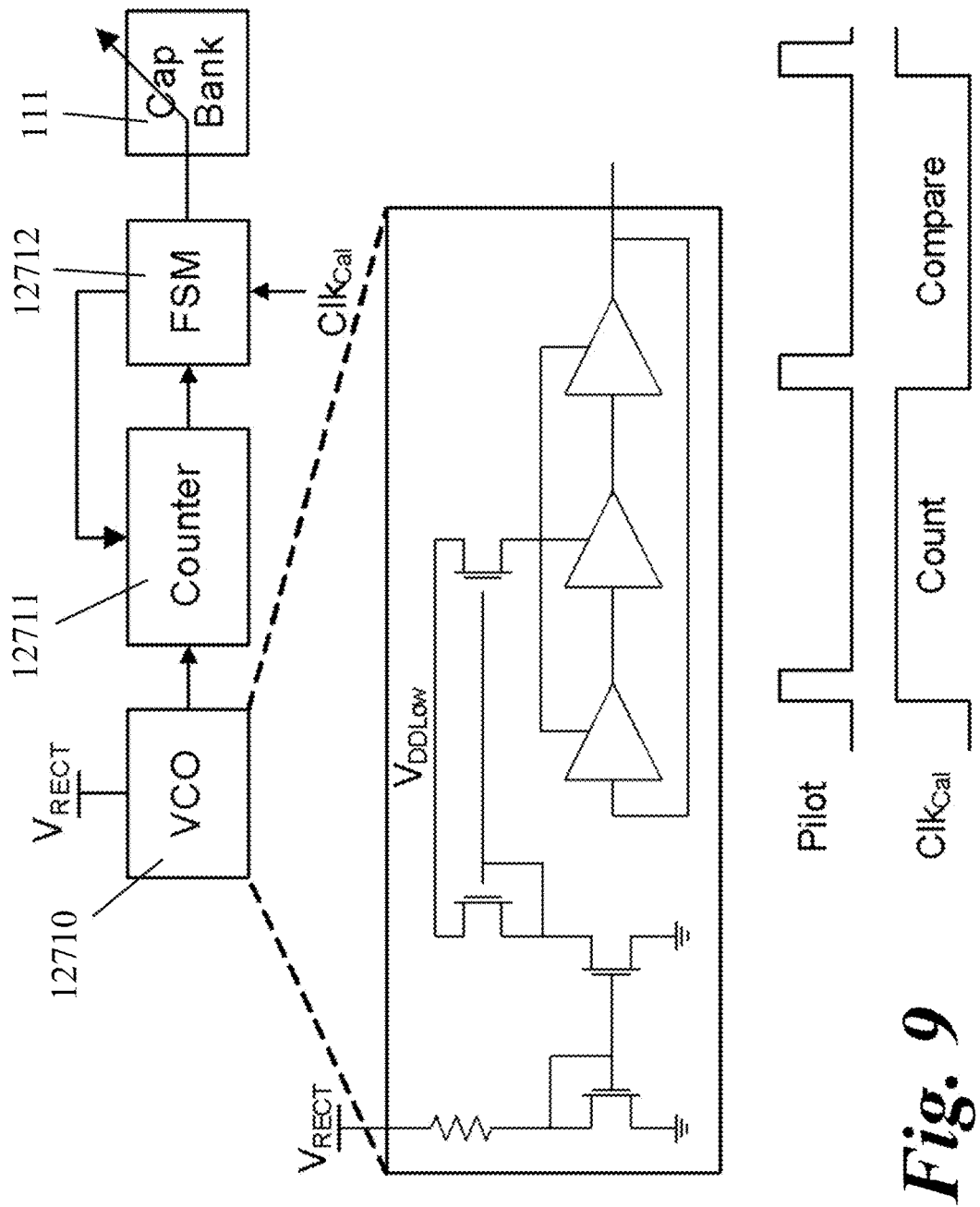
FIG. 9 provides an exemplary implementation of the on-chip adaptive tuning algorithm by an integrated calibration machine (127, FIG. 4A) in accordance with some embodiments of the invention. The implementation can include a VCO (12710), a counter (12711) and a Finite State Machine (FSM) (12712) that feeds the on-chip tunable capacitor bank (111, FIG. 4A) to implement the adaptive tuning algorithm as described in FIG. 8B).

The adaptation algorithm (as shown in FIG. 8B) is the first process the implantable sensor 1 would perform once the external transceiver transmits the power signal to provide enough power to the implantable sensor 1 to enable operation. The received RF power signal can be converted into DC using a cascade of low-dropout rectifiers 121 that provide enough voltage (~0.6-0.8V) to enable the resonant frequency calibration machine 127 to function. A low dropout regulator 123 can be utilized to provide a stable supply to the calibration machine circuitry 127 as shown in FIG. 9. The same regulator 123 can be used to provide the digital power supply to the system to minimize noise coupling between analog and digital circuits; two separate power supplies can be provided, one for the analog parts of the circuit of sensor 1 and a second for the digital parts of the circuit of sensor 1. This minimizes cross-talk. The rectifier 121 output voltage ($V_{RECT}$) can be used as an indicator of the quality of the resonant frequency matching where maximizing $V_{RECT}$ results in the near perfect alignment between the resonant frequency of the sensor 1 $f_{r2}$ and the resonant frequency of the transceiver 2 $f_{r1}$. $V_{RECT}$ can be monitored in different ways in the voltage domain or by converting it into time domain. In general, an ADC can be used to precisely measure this voltage, the ADC can be voltage mode that directly quantizes this voltage or current mode which converts it to a current and then quantize. In the voltage domain, a voltage mode ADC can be employed to digitize $V_{RECT}$ and based upon the voltage level, the sensor tuning frequency can be adjusted by adjusting the variable capacitor value ($C_{BANK}$). As during the calibration period, the supply voltage is low and not completely stable the more efficient way to do this is to convert $V_{RECT}$ into current and use a current controlled oscillator as digitizer. As an example, the ADC can be designed similar to the ADC 132 shown in FIG. 13.

In order to adjust $f_{r2}$ a variable on-chip capacitor (capacitor bank (111), $C_{BANK}$ varies between $C_0$ to $C_0+C_1\times 2^{n+1}$) can be utilized. The calibration machine (127) can include a state-machine This is a state machine that performs the gradient search which is explained as the calibration algorithm. The calibration machine starts the calibration algorithm from the middle capacitor size ($C_{BANK}=C_0+C_1\times 2^n$) as shown in FIG. 8B (350) and increases the capacitor value by one LSB (351), if as a result $V_{RECT}$ increases (352), it keeps increasing the capacitor value in LSB steps until $V_{RECT}$ starts decreasing (355). At this point, the calibration algorithm for chip tuning frequency will go back to the previous capacitor size. If as a result of the first step increase in capacitor value $V_{RECT}$ decreases, the calibration machine (127) starts decreasing the capacitor value in LSB steps (which will result in increasing $V_{RECT}$) until $V_{RECT}$ starts decreasing at which point the calibration algorithm will go back to the previous capacitor size and freezes the tuning capacitor.

As shown in FIG. 9, the calibration machine 127 can utilize a clock signal $Clk_{Cal}$ that is provided by the external reader through modulation of the power signal as a pilot signal which can provide an accurate timing reference. This clock $Clk_{Cal}$ can be used to define two phases, counting and comparison. A VCO 12710 connected to a counter 12711 can be utilized as a voltage detector (126) (FIG. 4A) to convert $V_{RECT}$ into a sequence of bits (e.g., a digital signal). During the count phase, the counter 12711 will count the number of VCO 12710 oscillations. During the compare phase, this number (the current count) can be compared with the previous count value to determine if $V_{RECT}$ has increased or decreased. A finite state machine (FSM) 12712 can be used to perform the adaptation algorithm (FIG. 8B) based upon these values of $V_{RECT}$.

During the calibration period, the entire circuit can be powered off except for the low voltage LDO, voltage detector and the calibration machine 127 to minimize the power drawn from the rectifier. Once the maximum power transfer condition is achieved, the rest of the circuitry in the implantable sensor can be powered on.

The rectifier signal is fed to two regulators (FIG. 4A) and a band-gap reference voltage generator. The two regulators provide a low-voltage (0.6-0.8V) and a high-voltage (1.2V) supply. The low-voltage supply is used for the digital blocks to reduce power consumption. During the initial calibration period this regulator powers the calibration machine. Once the tuning frequency calibration period is over, the high-voltage supply is enabled. This supply provides power to the analog circuitry that includes potentiostats that control the integrated sensing element 160 and the analog-to-digital converter system 132.

After tuning the internal resonant frequency of the sensor 1 to the internal resonant frequency of the external transceiver 2 using the tuning algorithm described and shown in FIG. 8B, another calibration period can be used to create an accurate internal clock signal. In order to comply with the Gen2 EPC UHF RFID protocol, the frequency of the internal clock should be ±5% accurate relative to the nominal value (160 KHz). This calibration of clock signal can be performed in a manner similar to the tuning frequency adjustment. The external clock signal can be used as a reference to adjust the frequency of the internal voltage controlled free running oscillator (VCO 12710). In this technique, during the count phase of the $Clk_{Cal}$, a counter can be employed to count the number of clock cycles and during the compare phase the count can be compared with the ideal number of clocks and based upon this comparison, the VCO frequency is increased or decreased (meaning if the count is lower than the ideal number the frequency is increased and if it is higher the frequency will be decreased). This continues until count becomes equal to the ideal number.

Figure 10:
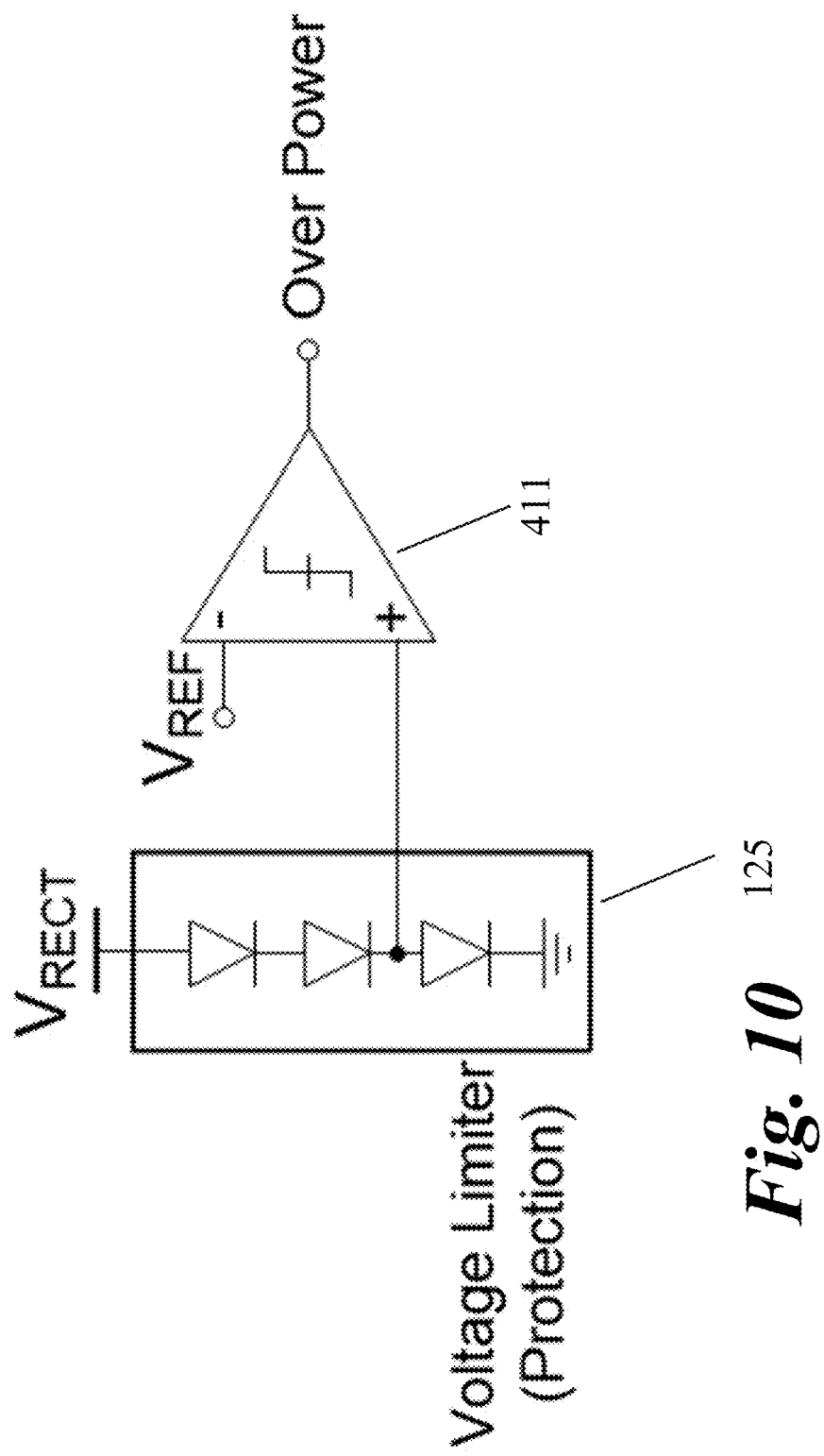
FIG. 10 provides a typical implementation of the voltage limiter (125) and over-power indicator (411) that provides the feedback to on-chip calibration machine (127), FIG. 11A and FIG. 11B provides embodiments of Potentiosat designs that can be employed for proper operation of an on-chip electrochemical integrated sensing element. Different Potentiostat designs utilize high-gain amplifiers in different topologies to control the potential of working electrode (AVE) relative to the reference electrode (RE) while providing balancing current through counter electrode (CE). For example, high-gain amplifier 510 is used in the Potentiosat represented by FIG. 11A while high-gain amplifiers 511 and 512 are used in the Potentiosat represented by FIG. 11B.

An internal received power level detection circuitry 411 in the sensor 1 (as shown in FIG. 10) can be employed to detect if power level is too high. It can then transmit this information as a specific data pattern to inform the external transceiver 2 in case of excess transmitted power so that the transceiver 2 reduces the transmitted power level and improve the battery life. The power level data is included in the data packet that is sent to the external transmitter and also includes the sensor readout. This circuit can be combined with the voltage limiter protection block 125 which can include a stack of diodes which clamp the output of the rectifier to avoid excessive voltage and transistor breakdown. This diode ladder can be used as a voltage divider which will be compared with the output of the bandgap reference generator $V_{ref}$ by power level detection circuitry 411 to detect excess transmitted power and output an over power signal to the voltage detector 126.

In summary, the systems according to some embodiments of the invention can provide autotuning capabilities on both external transceiver 2 and sensor 1 to optimize the performance of low-power wireless link. Autotuning can be used for compensating for manufacturing process variation which would result in low yield as resonant frequency would be expected to follow a Gaussian distribution and there could be some sensors with a untuned resonant frequency far from that of the transceiver. As the transceiver cannot use frequencies outside the allowed ISM band due to regulatory requirements, this will result in sensors that are impossible to power. Also the autotuning allows for in-situ adaptation to environmental changes while maintaining communication with the sensor. This can be useful as different patients have different body characteristics which results in variability in sensor resonant frequency. Furthermore, as different regions in the world have different assigned frequency ranges to ISM band, autotuning makes it possible for a single design to be usable across a wide range of frequency bands, and can be useful for patients traveling to different regions while wearing the sensor. Autotuning helps avoid under-powering of the sensor and together with power level detection, this design allows for optimizing the powering and communication and minimizing the transmit power in all conditions and maximize the external transceiver battery life.

One or more sensors 1 can be placed in desired tissue locations using injector (1000). The sensor 1 then can be powered by and communicates with the external transceiver 2 as described herein, or can be powered by and communicate with a smart device 3, such as a smartphone or smartwatch or fitness wearable in a similar manner as described herein, to achieve instantaneous and/or continuous sensing. The external transceiver 2 (or smart device 3) can receive sensor data, display sensor data, store the data, relay it to a smart device 3, or send it to a communication device 3, or a remote server 4. External transceiver 2, smart device, communication device 3, or remote server 4 can relay and process the sensor data in a manner commensurate with its processing, storage, or battery capability. The data processed in external transceiver 2, smart device 3, communication device 3, or remote server 4 can be relayed to external transceiver 2, smart device 3, communication device 3, or remote server 4 to provide, display, or store, information (e.g. blood glucose levels, pH levels, daily trends) or predictions thereof or suggestions (e.g. behavioral changes, treatment changes) based on sensor data or predictions.

At the end of sensor life, or when desired, the sensor(s) can be left in body, extracted via surgical tools, extracted using an extraction device, extracted using a thread, by pulling on a thread, or by using a thread to locate the sensor. Illumination in visible light, or other electromagnetic radiation, and human eye or appropriate detector, can be used to facilitate the implantation or extraction process.

In one embodiment, the sensor is extracted by pulling on a transcutaneous thread attached to the sensor on one end, and a disk of small (0.1 mm to 1 mm) diameter on the other end. In another embodiment, the disk is formed by making a loop as a part of a multifiber thread.

In an embodiment, visible light, in another embodiment Red light, Light Emitting Diode is powered and placed against the skin to illuminate the tissue surrounding extraction and/or implantation. This illumination allows the user or operator to see the sensor through the skin.

Wireless Communication

Wireless Communication can be done both to and from the sensor (1) using electromagnetic techniques. In one particular embodiment, the on-chip radio frequency coils or antenna structures of the sensor 1 can be used to communicate with the external transceiver 2. Such system can employ both active communication schemes where a signal is generated by on-chip telemetry units and a passive communication where the on-chip telemetry unit is used to modulate an incoming signal and the change is read by the external transceiver also known as backscattering. Such RF coils can be designed on top of the semiconductor circuits in the top metal layers which reduces the need of large die sizes. The top metals (for example, top most metal layer and 1 or 2 layers under it) are used to design a coil system to achieve good resonant coupling to an external coil at frequencies where attenuation through skin and tissue is minimized. Extra metal layers can be added during post-processing to improve the performance (quality factor) of the metal structures.

A switching mechanism (FIGS. 4A, 4B and 4C) can be used for power-optimum telemetry from the implanted chip to the external transceiver. For example, backscattering through the modulation of the power signal (which can be transmitted to supply power to the implant) is a low power and yet efficient method for this telemetry. Backscattering is done through changing the impedance of the LC tank by using a switch 154 and hence creating impedance mismatch between external transceiver's LC resonant element 112 and an on-chip LC resonant unit 110 which results in signal reflection. This reflected signal is picked up by the external device (2) to complete the communication. The change in impedance can be done by using the switching module (EPC Gen Modulator 153) that works either by changing the impedance using a switch 154 as shown in FIG. 4B, or by changing the capacitance in the implanted-chip's LC tank (by switching in or out a parallel capacitance 155 using a switch 156 to the tank as shown in FIG. 4C. When the switch 156 is open its resistance is close to infinity, while when the switch 155 is closed it has a finite resistance. By turning the switch on, the LC tank impedance is reduced due to the parallel resistance of the switch.

Data telemetry from the implanted chip 1 to external transceiver 2 can also be accomplished using optical signals (e.g. using microlasers, UV or IR LEDs). In this case an external pump laser can be used to power a microlaser that is bonded to the implanted chip. The microlaser can be modulated using the signal from the transmit unit (150) by forcing the current flow through the laser device which will minimize its efficiency and decrease the laser output which can be detected as a signal using the external transceiver.

By autotuning, the external transceiver 2 acts as the master and sets the powering and communication frequency; the sensor 1 acts as the slave and tracks the transmitter frequency and adapts its resonance so that its resonance aligns with that of the transmitter frequency. It should be also noted that the automatic matching at the external transceiver 2 also makes sure that transmitter resonance occurs at the transmit frequency. This is particularly important as different regions in the world have allocated different frequency bands to ISM UHF. Region I has 902-928 MHz and Region II 865-868 MHz as the band for ISM UHF. The autotuning allows for the transceiver 2 to set the transmit frequency based upon the region of operation and the sensor 1 would follow this frequency by tuning to the master frequency.

Sensor Signal Acquisition Circuit

For the type of sensing element used in a particular design, a control circuit (e.g. Potentiostat) can be implemented and incorporated into the underlying semiconductor electronics. For example, for electrochemical sensing elements using amperometric measurement at a given potential, a potentiostat can be designed and implemented to perform the function. FIGS. 11A and 11B show some example designs of the potentiostat circuit that can be used for amperometric applications. Dynamic designs which can automatically adjust measurement range based upon the strength of signal being measured can be used. Self-calibration algorithms which compensate for sensor to sensor variations after sensor manufacturing can also be used. The control circuits for other types of sensors can be implemented similarly. In case of multiple sensing elements on same chip, shared control circuitry can be used based upon the application. For example, the same potentiostat control circuitry can be used to measure the amperometric response of multiple working electrodes using switching circuitry to selectively connect the sensing element (e.g., a working electrode) to the potentiostat control circuitry. If required, a dedicated control circuit can also be included for each sensing element, at the expense of larger chip area.

The potentiostat can be implemented in different ways. In accordance with some embodiments of the invention, the potentiostat can be used for single analyte sensing. In accordance with some embodiments of the invention as shown in FIG. 11A, a single op-amp 510 can be used to maintain the voltage difference between the working electrode WE (connected to analog power supply Vtune) and the reference electrode RE while providing current source/sink capability at the counter electrode CE. In accordance with some embodiment of the invention as shown in FIG. 11B, an op-amp 512 can be used to control reference electrode RE voltage while providing source/sink capability to the counter electrode CE and another op-amp 511 can be used to control the working potential for the working electrode WE. In either circuit, the sensing element WE current $I_{sensor}$ can be used to measure the concentration of the analyte in the tissue or fluid that contacts the sensing element 160 of the sensor 1.

In accordance with some embodiments of the invention, the potentiostat can be used for multi-analyte sensing. In this embodiment as shown in FIG. 12, an op-amp 513 controls the reference electrode RE voltage while providing source/sink capability at the counter electrode CE and another op-amp 514 is utilized to control the potential for each working electrode WE similar to the topology in shown in FIG. 11B where the amplifier 511 sets the working electrode WE voltage through establishing negative resistive feedback and converting the sensor redox current into a voltage for subsequent processing. This method allows for independently controlling the potential difference between working WE and reference electrodes RE in a multi-analyte sensor where there are several working electrodes WE for sensing different analytes shown in FIG. 12).

Figure 13:
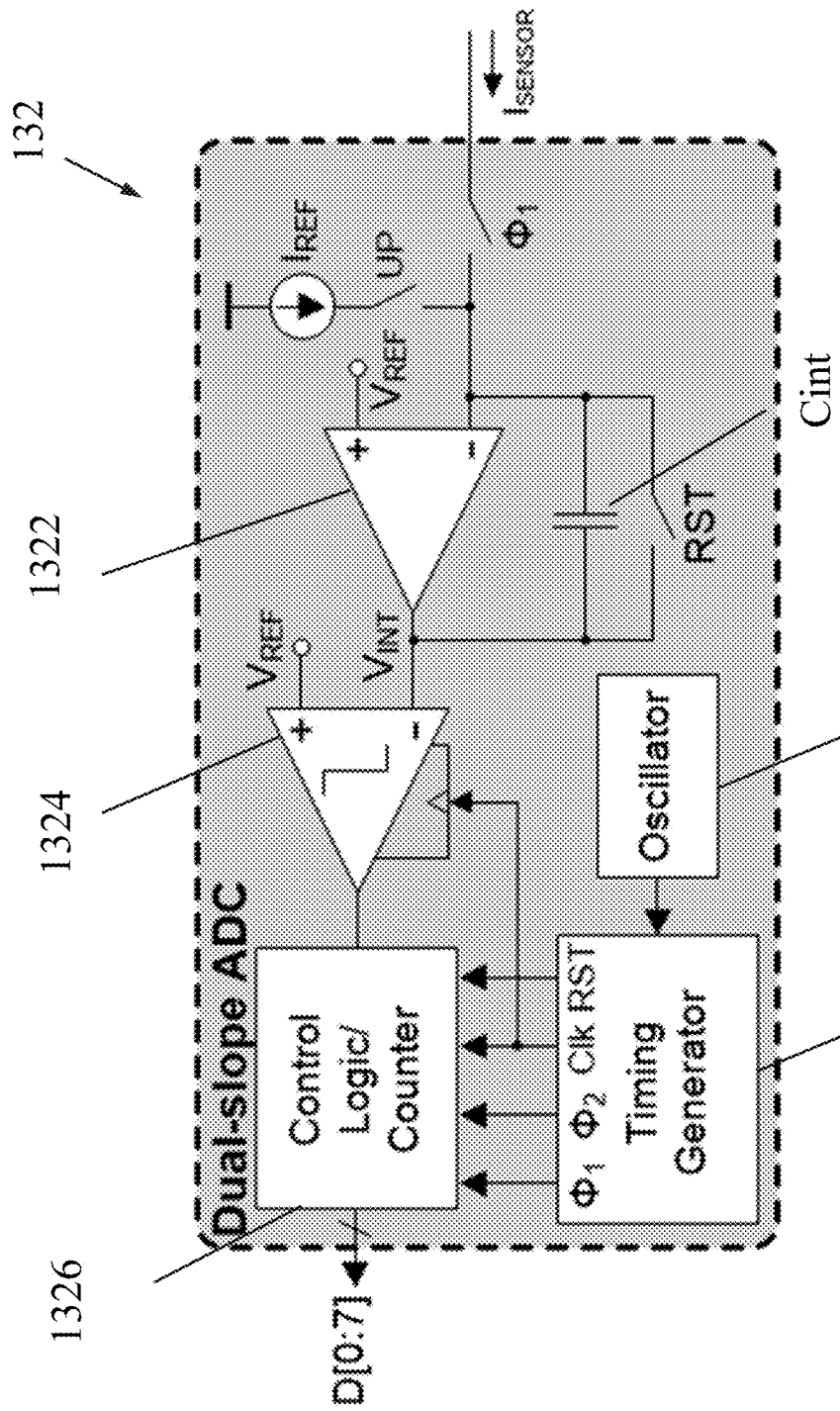
FIG. 13 provides an example of the dual slope ADC circuit 132 within the signal acquisition and processing unit (130, FIG. 4A). The ADC can include a voltage comparator (1324), an oscillator (1329), a timing generator (1328), a control amplifier (1322), and Control Logic Unit (1326).
Figure 14A:
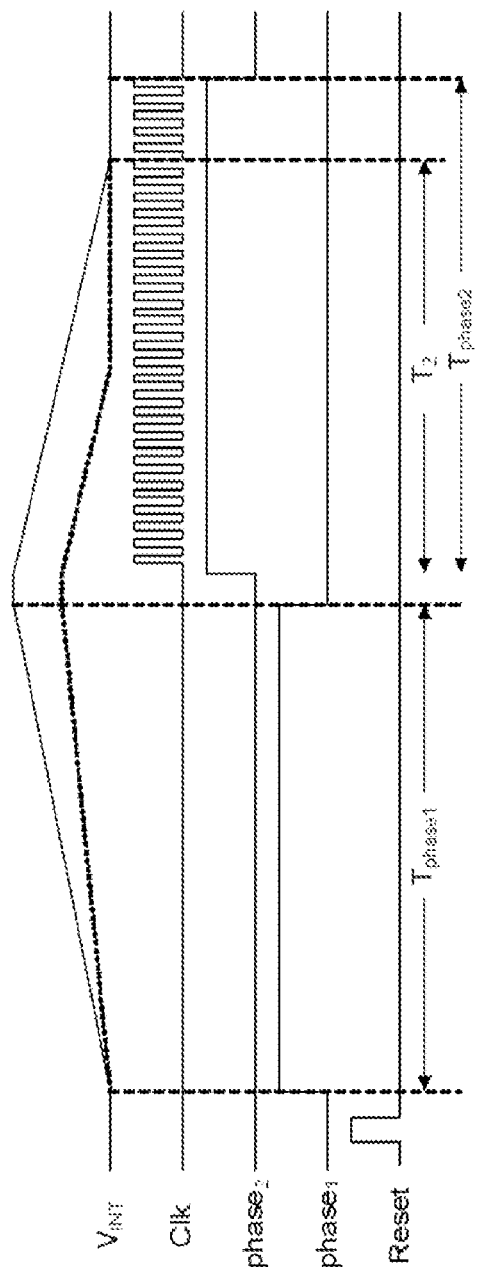
FIGS. 14A and 14B timing diagrams providing a description of the operation of the ADC circuit 132.
Figure 14B:
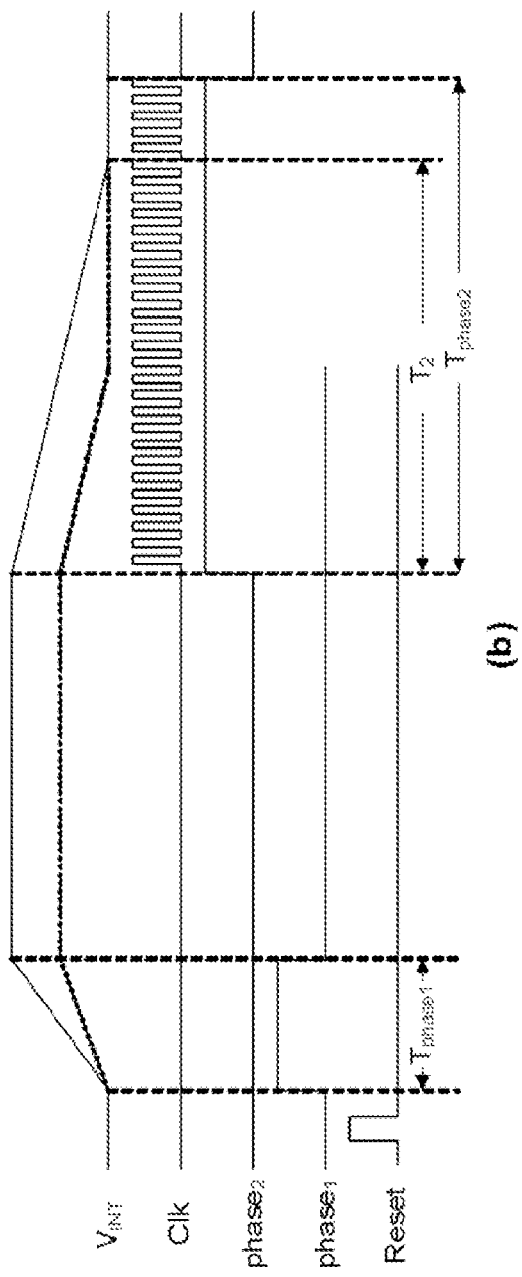

A dual slope ADC 132 can be used to directly convert the sensing element current coming from the potentiostat into the digital domain (e.g., 8-bit data stream) as shown in FIG. 13. The ADC circuit 132 can be configured to operate in two phases, as shown in FIGS. 14A and 14B. In phase 1 shown in FIG. 14A, the sensing element current ($I_{sensor}$) is integrated over capacitor $C_{INT}$ using an op-amp 1322 with $C_{INT}$ in the feedback path. In phase 2, a reference current $I_{REF}$ discharges $C_{INT}$ to its original value which would take a certain time ($T_2$). The ratio between $T_2$ and $T_{phase1}$ is taken as the sensing element current as this ratio increases with an increase in sensor current and decreases with a decrease in sensor current. To accommodate different current ranges and achieve a high dynamic range, $T_{phase1}$ can be programmable by the external transceiver. In the beginning, a default value (mid-range) for $T_{phase1}$ can be selected by the ADC 132. At any given time, the external transceiver 2 can send new value for $T_{phase1}$ as part of the telemetry command it sends to the sensor 1. The sensor can execute this command by changing the value of $T_{phase1}$ to this new value.

In accordance with some embodiments, in order to support multi-analyte sensing without excessive increase in power consumption, resource sharing can be used. In some embodiments of the invention, each individual sensing element can be controlled by a dedicated potentiostat while an analog-to-digital converter can be shared among all sensing element-potentiostat pairs through time division multiplexing in which the digitization period is divided among some or all of the sensor-potentiostat pairs. During each time slot, the output of one sensing element-potentiostat pair is digitized. In accordance with some embodiments of the invention, the sampling rate can be set to a rate that is well above the rate at which the body changes physiological to avoid sensed signal loss. Normally, the ADC can operate at much faster rate than that of the physiological signals, hence such multiplexing doesn't create any loss of data.

In accordance with some embodiments, to allow for multi-analyte sensing while minimizing the electronics, reference electrode RE and counter electrode CE are shared among sensing elements and controlled by a single potentiostat while each sensing element enjoys a dedicated working electrode WE and an analog front-end (AFE) 514 to be able to independently set the redox voltage and acquire the corresponding electrochemical signal (FIG. 12). The outputs of AFE's 514 can be time multiplexed into a single analog-to-digital converter 132. The digitized output of each sensing element can be sent to the wireless transceiver sequentially, using time division multiplexing or aggregated in memory and sent on demand or in an arbitrary sequence.

Integrated Sensing Element

The sensor (1) can be wirelessly powered using, for example, near field communication (NFC) to transmit power and data between sensor (1) and an external transceiver 2 which can be configured as an NFC reader. Sensor (1) can be configured to perform in-vivo sensing using one or more different sensing mechanisms, for example, electrochemical sensing, optical sensing, acoustic sensing, mechanical sensing, capacitive sensing, and/or RF sensing mechanisms. The mechanism selected can depend upon desired sensing application. In accordance with some embodiments of the invention, sensor (1) can include an integrated sensing element and a corresponding integrated circuit to provide the desired sensing functionality.

In accordance with some embodiments of the invention, electrochemical sensing elements can be used to sense one or more analyte of interest in the tissue where the sensor unit is implanted. The sensing elements can include one or more electrodes (FIG. 15A) that can be formed using conventional semiconductor fabrication processes and post-processes. For example, if the application can work with aluminum electrodes (or any other top most metal available in CMOS process), no post-processing is required as the CMOS foundry can provide the sensor chip with desired electrode material. However, if the application conditions could be corrosive, a more suitable material (e.g., Gold, Silver, Titanium, and Platinum) can be used. In addition, the top layer of electrodes can be selected based on its sensitivity to the analyte of interest. For example, for amperometric glucose sensors, post-processing is used to cover or replace the top metal layer 810 with platinum which is suitable for long-term electrochemical sensing of glucose.

Figure 15B:
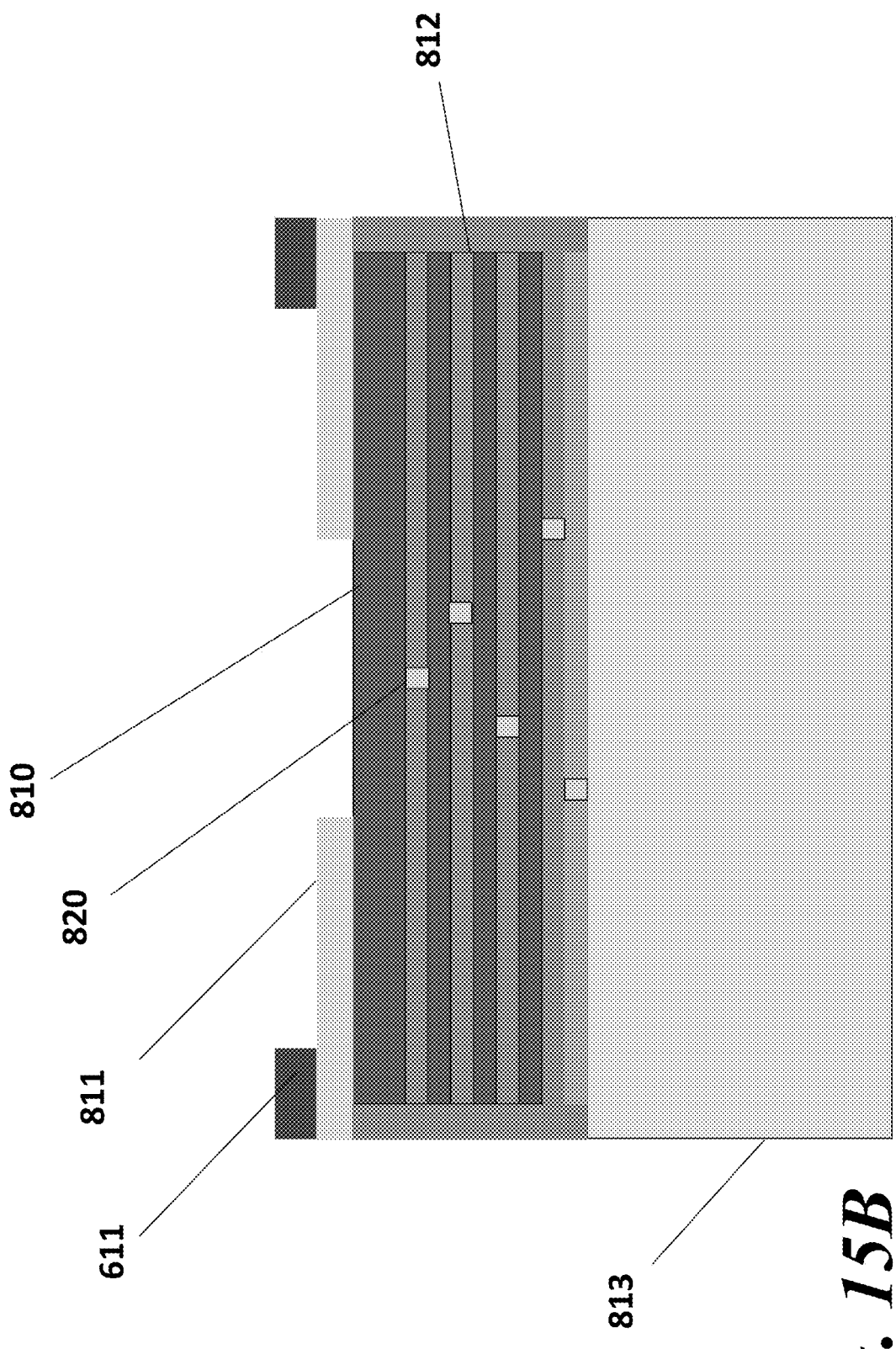
FIG. 15B is a side cross-section schematic view of sensor (1), showing a substrate (813), a metal-insulator-metal stack (812), a top metal (810), a top insulator (811), and an additional insulator/protection polymer layer (611).

The sensing element electrode structure can be formed in the top metal layer of the semiconductor sensor chip during fabrication processing or post-processing. The size and shape of the sensing element electrode structure can be selected based upon the sensing application and the desired implant geometry. In accordance with some embodiments of the invention, the sensing element (160) can include a concentric arrangement of electrodes, e.g., three circular or rectangular electrodes: a centrally located reference electrode (e.g., a rectangle of 50 µm by 1500 µm), an outer counter electrode (e.g., a rectangle of 600 um by 1500 µm), and a working electrode (e.g., a 150 µm by 1500 µm) located between the reference electrode and the counter electrode (FIG. 15A). This structure can be formed in the top metal layer 810 by removing the top passivation layer of the chip to expose the metal sensor electrodes (FIG. 15B).

Figure 16A:
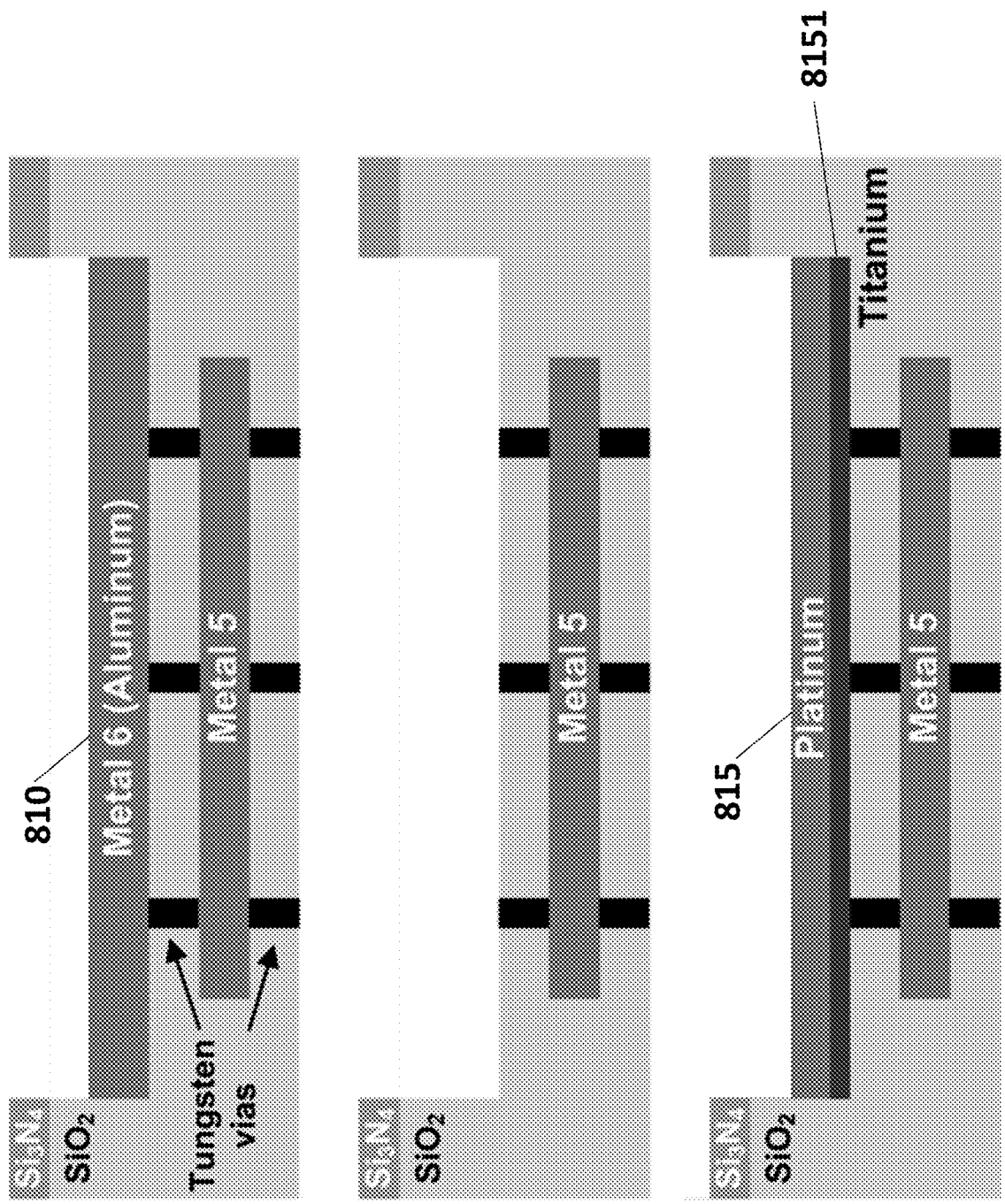
FIG. 16A shows the process steps used to create a planar electrochemical integrated sensing element (160), by changing the top metal layer on the semiconductor platform via etching the existing metal (e.g. Aluminum, 810) and replacing it with a more desirable material set (e.g. Ti 8151 and Pt 815).

The top metal can be a thicker metal in high frequency CMOS processes, to generate high quality coil antenna at such frequencies. In some cases, a more suitable material can be coated on the top metal without etching it (FIGS. 17A-17E). For some other cases, first step of post-processing involves removal of this top metal layer 810 for a better control on the morphology of the more suitable material (FIG. 16A). This etching can be achieved by using wet etching (e.g. using a mixture of Nitric acid and Phosphoric acid) or dry etching (e.g. Chlorine based RIE Plasma).

Figure 17A:
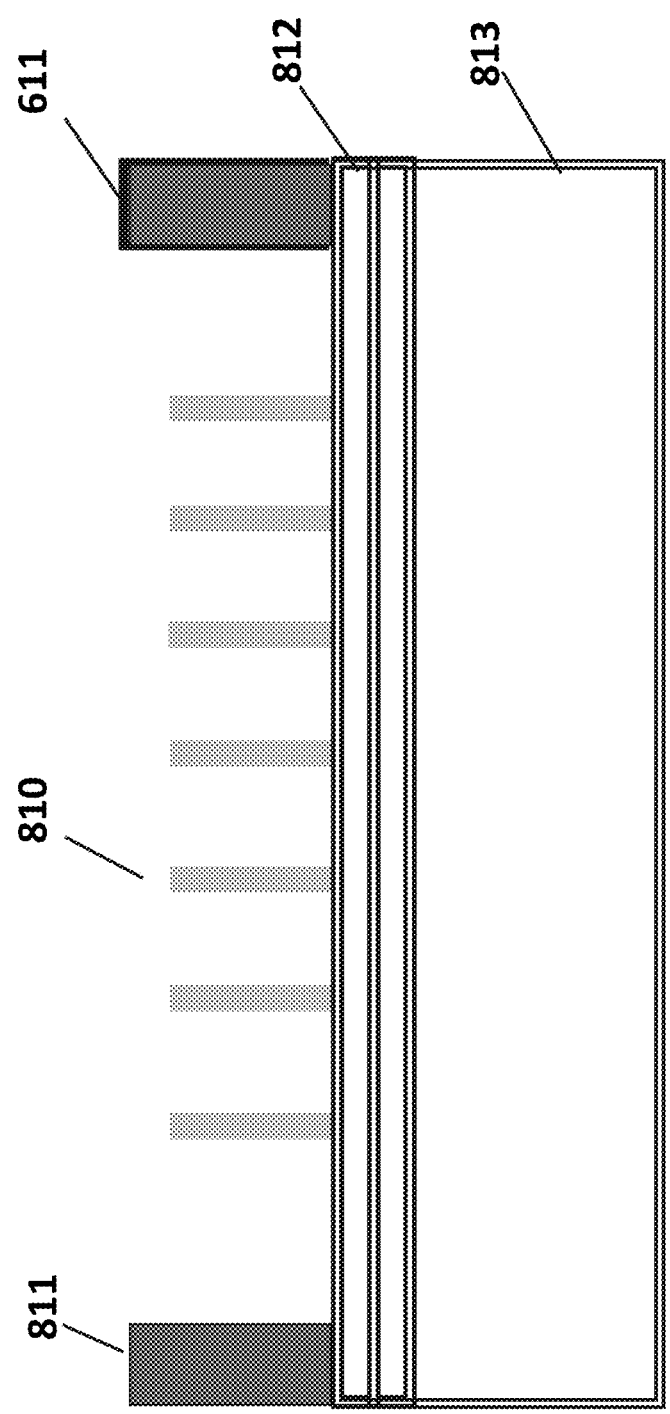
Figure 17B:
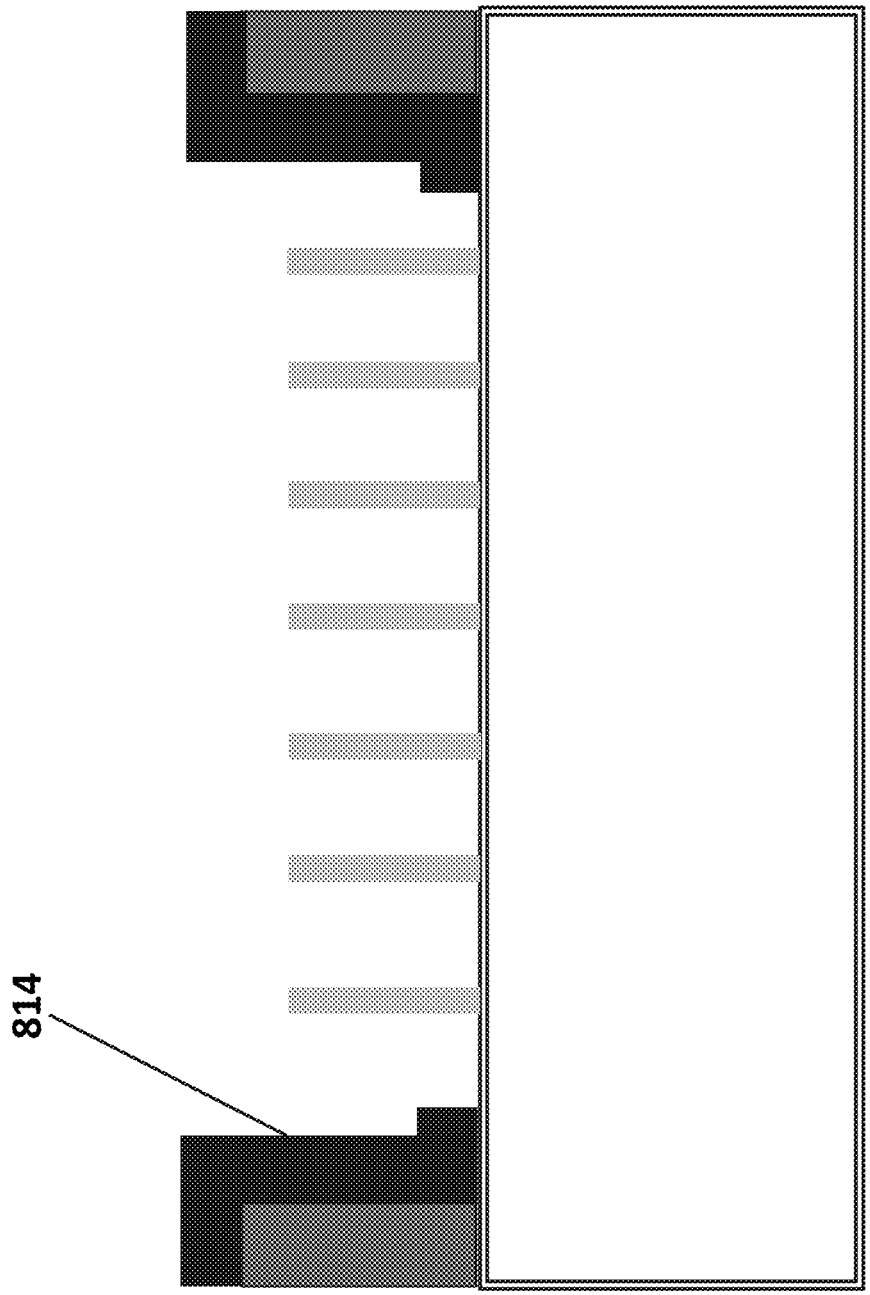

Next, lithographic (e.g. photolithography) patterning is done to expose the sensing element electrode while covering the rest of the wafer with a suitable material (e.g. photoresist) (FIG. 17B). For some applications, this patterning can be achieved using custom stencils i.e. without lithography.

Figure 17D:
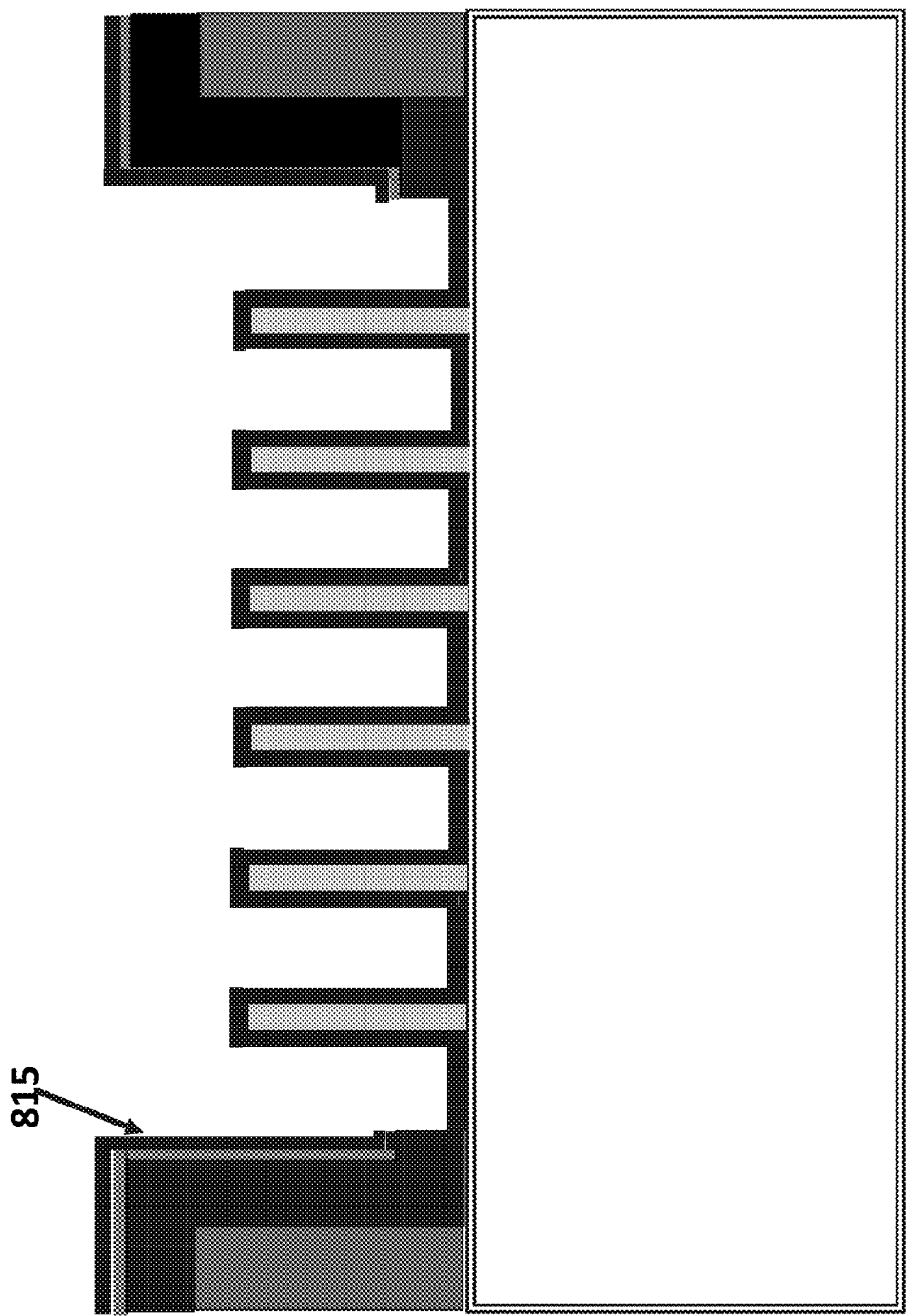
Figure 17E:
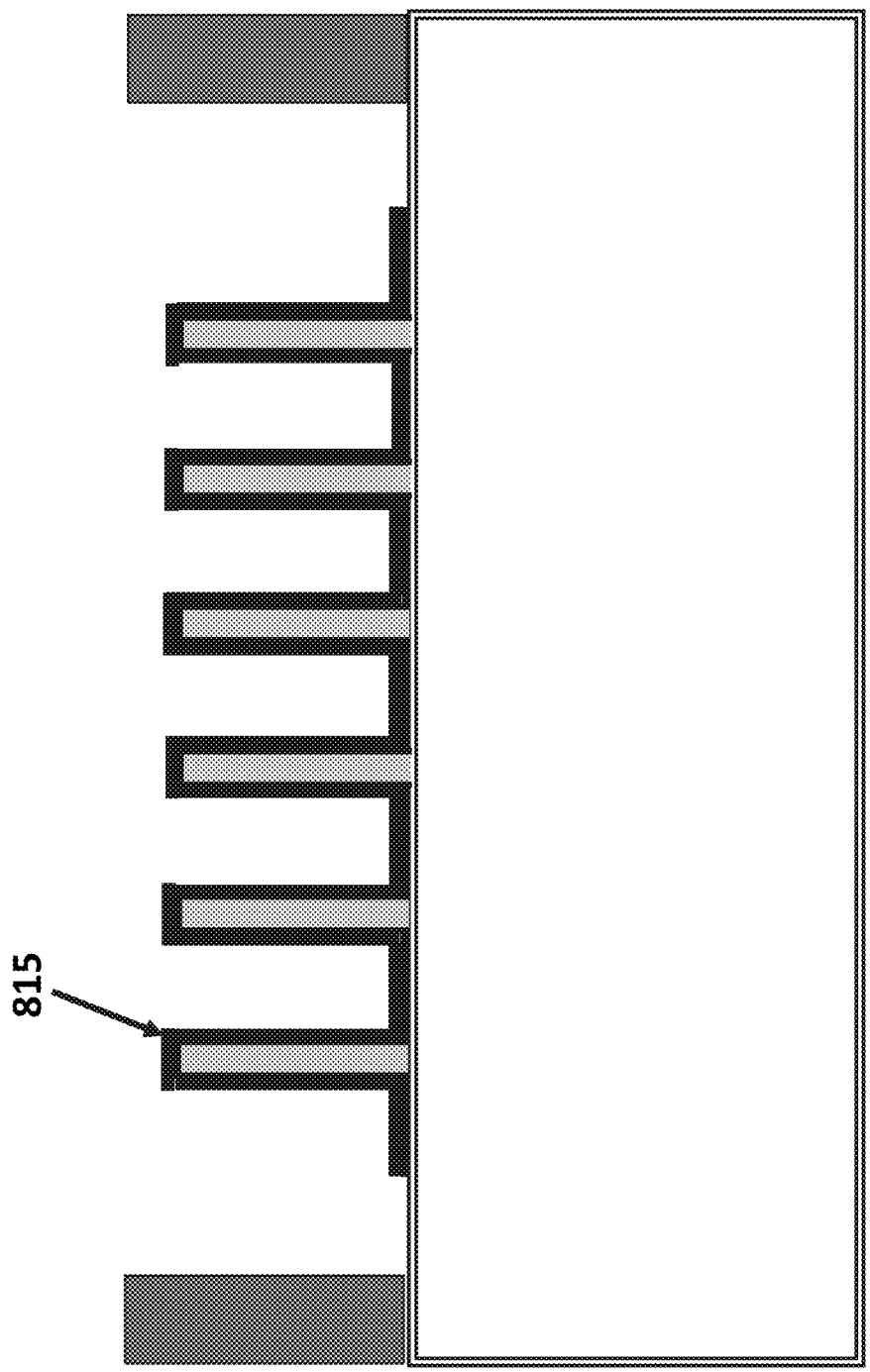

This patterning is followed by deposition of suitable metal stack; for example, a Ti intermediate layer of small (e.g. 20 nm) thickness as the adhesion layer followed by deposition of relatively thicker (e.g. 100 nm) of Platinum 815 as shown in FIG. 16A (for planar electrodes) and FIG. 17D (for pillar electrodes). Physical vapor deposition (e.g. Sputtering, ebeam deposition and thermal evaporation), Chemical vapor deposition and Electroless Plating are different methods that can be used for thin film deposition. Sputtering will form a relatively rough surface compared to e-beam or thermal deposition both of which result in smoother electrodes. To achieve higher surface area and to enhance bonding between the sensing element and the subsequent chemistry layers, the metal surface is designed to have rougher finish (as compared to smooth or mirror finish). This is achieved by controlling deposition method (e.g. electron beam deposition, thermal evaporation, chemical vapor deposition, sputtering), deposition environment (e.g. pressure), and deposition energy. In an embodiment, sputtering at 30 mTorr pressure and 100 W DC power generates metal coating with highest surface area for a planar geometry.

Next step of the post-processing will be lift-off to remove metal layers from the unwanted regions. This is achieved by soaking the coated devices in solvents. Alternatively, unwanted metals from coated devices can be etched in appropriate solutions (e.g. in aqua regia).

An optional step is to perform another lithography followed by Silver deposition, liftoff and Chlorine exposure through wet solution (e.g. Ferric Chloride) or dry plasma (e.g. Chlorine Plasma) to create silver based reference electrodes (e.g. Ag/AgCl). Ag/AgCl RE are more suitable for some applications (e.g. open circuit potential measurements).

Another optional step is to create polymer structures around the sensing element electrode area to create isolation or to improve chemical functionalization (FIG. 15B showing CMOS device with standard top metal, 16B showing CMOS device after etching top electrodes and replacing those with custom electrodes). For example, Polyimide structures can be used around the sensor to cover antenna structures to protect the antenna from harsh processes (e.g. dicing) and from subsequent chemical coatings.

Figure 16B:
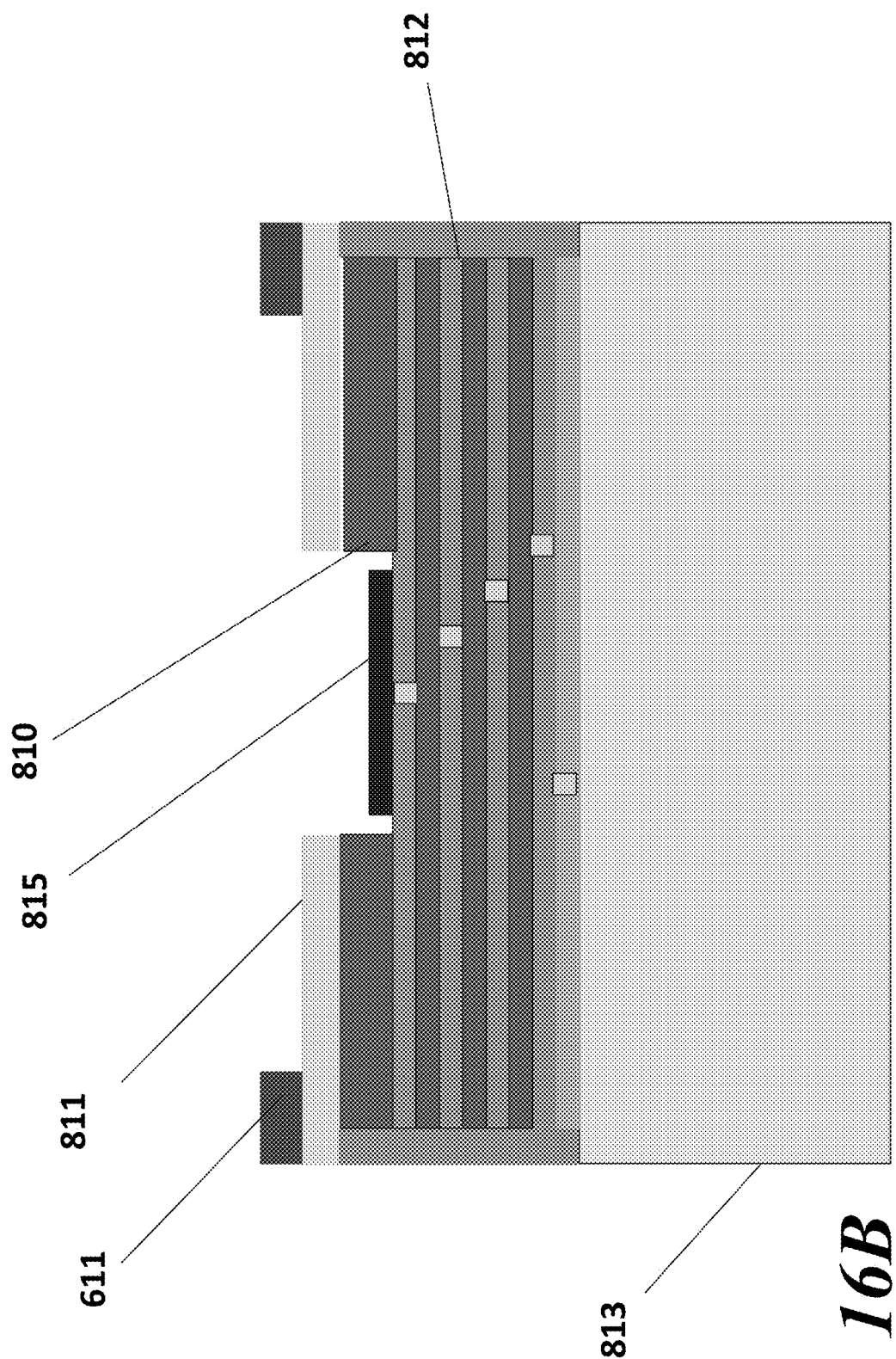
FIG. 16B shows the cross section of a typical CMOS device after etching and replacing the top metal 810 with a more desirable metal 815.

FIGS. 16A and 16B summarize the wafer-level post-processing steps involved in the fabrication of the planar electrochemical sensing element on the semiconductor substrate. FIG. 16A shows that the top metal electrodes 810 in CMOS are first etched using wet or dry etching. Next, those are replaced with more suitable metal (e.g. Pt) electrodes using lithographic patterning and metal deposition methods, resulting in noble metal electrodes 815.

In accordance with some embodiments of the invention, the strength of the sensing element signal is proportional to surface area of the electrode and the effective signal strength can be increased by utilizing patterned or non-planar electrodes instead of conventional planar electrodes. For example, an array of aluminum pillars can be used instead of planar sheet of aluminum as the sensing element and both the working and counter electrodes can be constructed in this form. Such structures can be formed using a semiconductor fabrication process, by post-processing or by a combination of both. These pillars can similarly be coated with suitable interface materials for each application. The pillars can be 0.25 microns to 25 microns (e.g., 2 microns to 5 microns) on a side (square pillars) and can be separated by same distance as their size. Pillar height can range from 0.1 um to 10 um (e.g., 2 microns to 5 microns) as determined by the semiconductor process. In accordance with embodiments of the invention, the pillar structure provides for a higher sensitivity and selectivity in a sensing element as compared to conventional planar designs. Furthermore, formation of pillars on the top metal layer allows direct integration with underlying circuitry and results in more reliable and robust sensing element as compared to other approaches including those using other nanostructures obtained from Silicon or other substrates [4]. In accordance with some embodiments of the invention, the pillars can be partially or completely etched in order to form a more planar structure. When completely etched, the pillars are totally removed and result in a planar electrode after next coating step. When partially-etched, pillars are thinned down and are shorter in height and possibly width.

Figure 18:
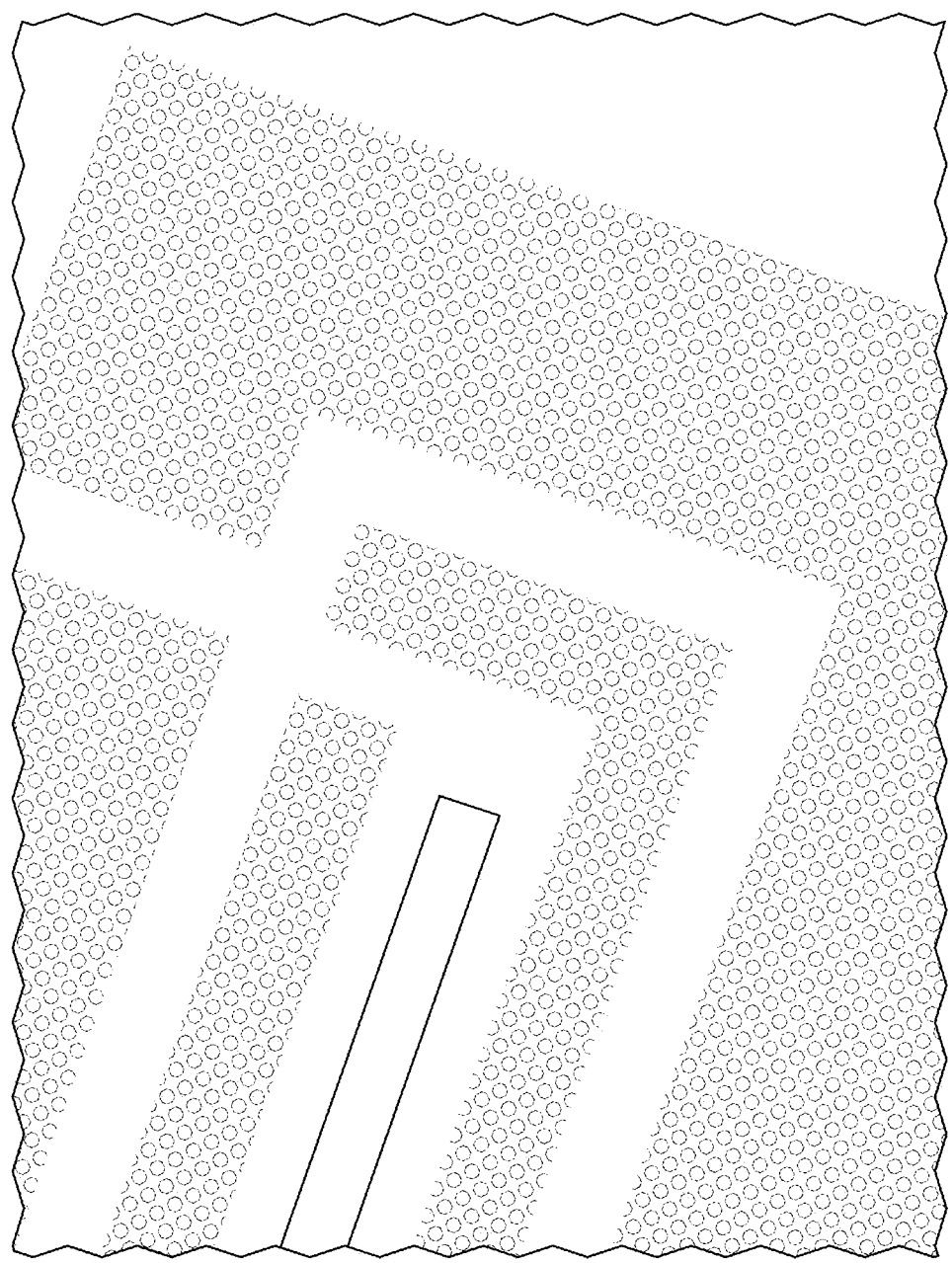
FIG. 18 provides is a picture of an embodiment of an integrated sensing element design with pillar based patterned electrodes.

The fabrication of the sensing element electrodes with one or more pillars can use similar patterning and coating processes (FIGS. 17A-17E showing process steps, and FIG. 18 showing an example of resulting electrodes). The first step is lithographically forming the pattern for electrodes in a lithographic material (e.g. photoresist) while covering rest of the chip with the lithographic material. As an example, AZ5214E resist can be spun at 3000 rpm, baked at 95 degrees C. for 5 minutes, and exposed using i-Line (e.g., 365 nm UV radiation) exposure in an MA6 mask aligner for 2 seconds. LOR resist can be used to help with liftoff. Image reversal can also be used for this purpose. In this case, a post-exposure bake at 110 degrees C. for 2 minutes is performed followed by a flood exposure in MA6 for 3 seconds. For both positive and negative patterns, the resist can be developed in a developer (e.g. AZ300). An example of the patterned device is shown in FIG. 18

This is followed by sputtering of Ti (e.g. 20 nm) and/or TiW (20 nm) followed by Pt (100 nm). Sputtering parameters are optimized to achieve the desired morphology of the coated material (e.g. Pt) (FIG. 17B.). After sputtering, a conformal coating is achieved as shown in FIG. 17C.

Solvent Lift-off is then performed (e.g. dipping sensors in acetone for 30 minutes) to remove metal from unwanted areas and only keep those on sensing element electrodes (FIG. 17D.). Alternatively, materials can first be deposited everywhere and then etched with appropriate wet and/or dry etching methods.

An example of resulting sensor with pillar array is shown in FIG. 18.

To enable multiple analyte sensing, multiple on-chip sensing element electrodes can be used to minimize cross-talk; although in some embodiments and/or configurations, the same sensing element can be used and cross-talk can be eliminated using other methods (e.g., detection at different potentials, signals of different frequencies, etc.). For example, Platinum electrodes can be used to detect hydrogen peroxide (using 0.4V vs. Ag/AgCl RE) or Oxygen (−0.2V vs. Ag/AgCl). To limit the increase in the overall size of the device while still providing adequate sensitivity for multiple analyte, 3-D pillar structures can be used to increase effective surface area and hence better signal to noise ratio (SNR). The 3-D structure can be created during the standard semiconductor fabrication by patterning the top most metal in the semiconductor process with appropriately sized (e.g. length of side for a square pillar) electrodes at an appropriate pitch (e.g. 2× the dimension of the side of the pillar) in a two dimensional array and removing the passivation layer between the electrodes. This results in pillar-like structure formation with tall metal electrodes placed adjacent to each other without any passivation material in between, as shown in FIG. 17A. Each individual working electrode can have an array of such pillars without any insulation between those. The individual working electrodes will be isolated from each other using a combination of top passivation and additional polymer layer(s).

Figure 19:
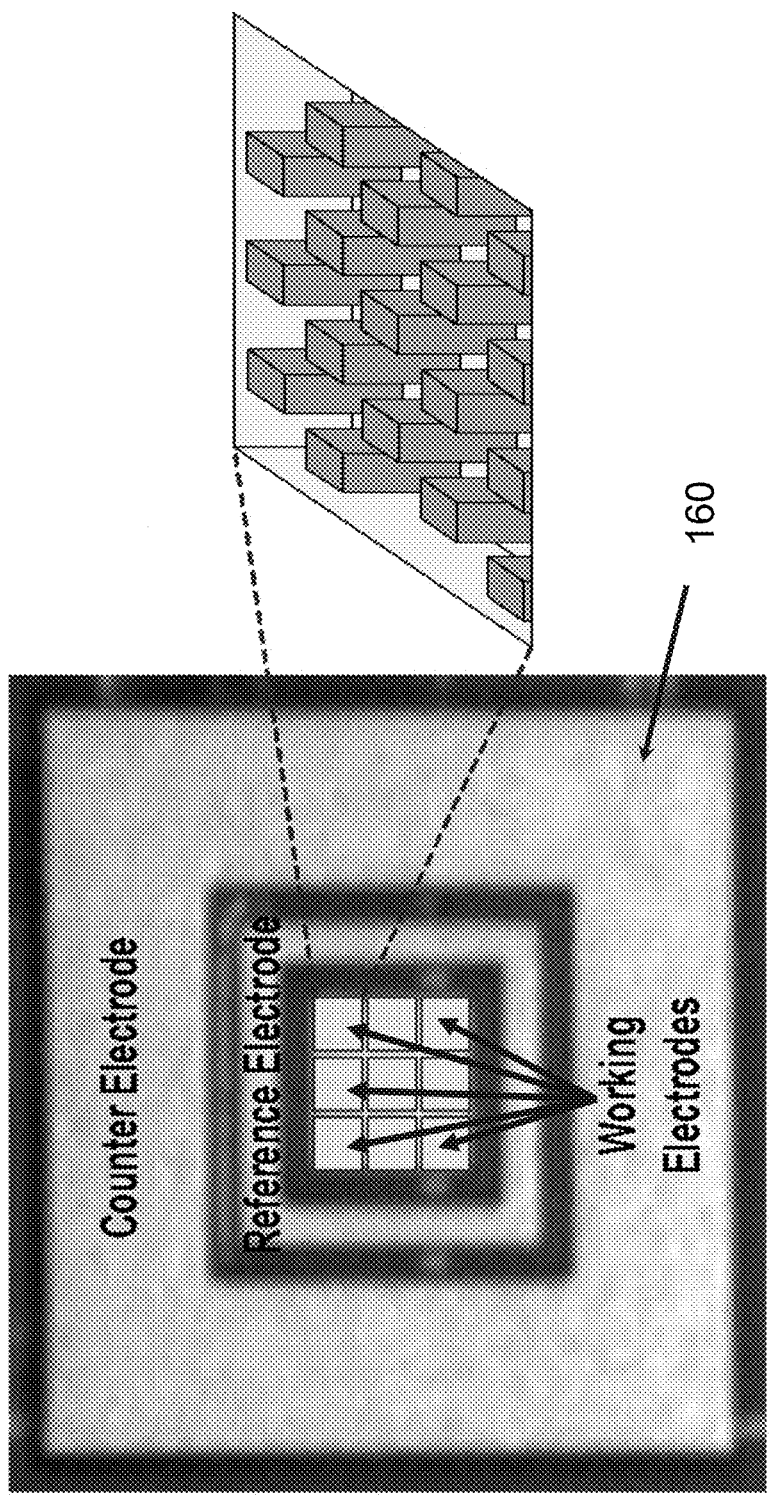
FIG. 19 shows an embodiment of how multiplexing can be achieved using multiple patterned working electrodes, sharing the same reference and counter electrode. The individual working electrodes can be isolated using top insulation (811) which can optionally be augmented with additional polymer insulation layer (611). The inset shows a detailed view of one of the working electrodes

In accordance with some embodiments of the invention, in order to further reduce the physical area consumed by many sensing element electrodes, one or more of the counter and reference electrodes can be shared among (e.g., common to) all sensing element electrode sets and only a working electrode can be used for each individual analyte sensor (FIG. 19). Each working electrode can be surrounded by a CMOS passivation and/or additional polymer structure to isolate it from rest of the working electrodes and to allow for unique functionalization of individual electrodes.

In accordance with some embodiments of the invention, where isolation is required, all the sensing element components for any one analyte application can be dedicated (e.g. separate working, reference and counter electrodes) and isolated from others using CMOS passivation and/or additional polymer isolation.

To improve adhesion of subsequent chemistry layers is to design support structures around the sensor. Polymer walls around the sensor can be used to act as 'well structure' as well as 'adhesion promoting structure' as some functionalization materials (e.g. Serum Albumin based Hydrogel) adhere better to an activated polymer surface than to Silicon Nitride insulation structure. As an example, polyimide structures around the sensing element can be used for this purpose. In some cases, such structures can be provided by the CMOS foundry or a similar foundry as part of the fabrication process. For example, polyimide structures are provided to the end-user by the CMOS foundry and can work as adhesion promoters for some applications.

Surface Functionalization

Once the suitable solid-state sensing element is realized on top of the electronics substrate, either by CMOS process (e.g. direct use of Aluminum) or by postprocessing (e.g. replacing or covering Aluminum with Platinum), the sensing element can be functionalized to be sensitive (e.g. create a meaningfully large response for a small change in analyte concentration) and specific (only create signal in response to change in concentration of one or more particular analyte). For example, for in-vivo glucose sensors, one or a multitude of working electrode sensing elements can be covered with an enzyme that reacts with glucose (e.g. glucose oxidase (GOx)) to generate a specie that be directly detected by the sensing element (e.g. GOx generates Hydrogen peroxide upon reacting with Glucose in presence of oxygen, and Platinum working electrode detects hydrogen peroxide and generates a current $I_{Sensor}$ proportional to its concentration). Optionally, another working electrode without any enzyme coating can be used for background (e.g. oxygen) measurements for signal corrections.

In one embodiment, this enzyme is immobilized on the sensing element in a hydrogel (e.g. a cross-linked protein hydrogel) of thickness 0.01 µm to 50 µm, preferably 2 to 6 µm. This can be done using different techniques. As an example, this can be done through immobilization of the enzyme such as GOx in a hydrogel created by proteinaceous material with glutaraldehyde as the crosslinking agent. The proteinaceous material can be a blocking agent such Human Serum Albumin (HSA) or Bovine Serum Albumin (BSA) or some other Serum Albumin (SA). Herein a "blocking agent" is a material that blocks unwanted binding interactions of the sensor or sensor components with tissue materials and fluids and avoids or decreases fouling of the sensing element.

Figure 20B:
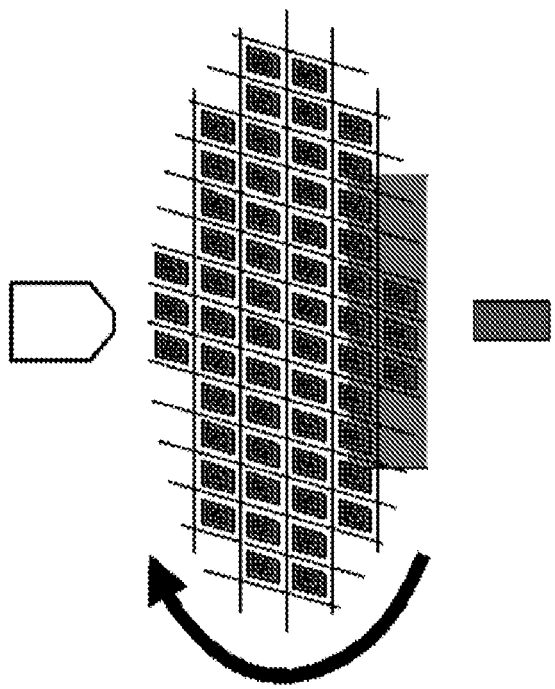
FIGS. 20A and 20B show process steps to coat the sensors with materials required by chemical sensing applications. As depicted in FIG. 20A combination of solution dispensing (e.g. using pipette like devices), spraying (e.g. using fine dispensing heads), and dipping can be used to apply small volume of material (e.g, polymer) on the sensors (FIG. 20A). The sensing chip or wafer can be spun to more precisely control the thickness of the layer (FIG. 20B).
Figure 20A:
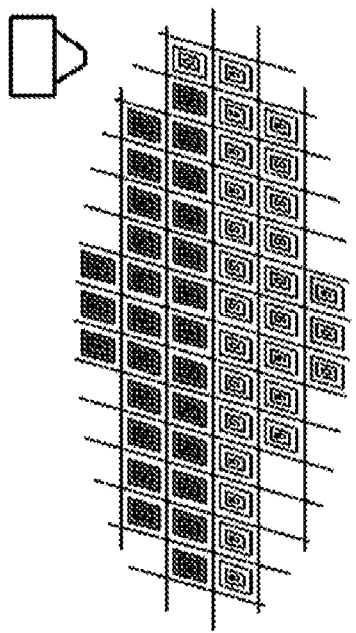
Figure 21:
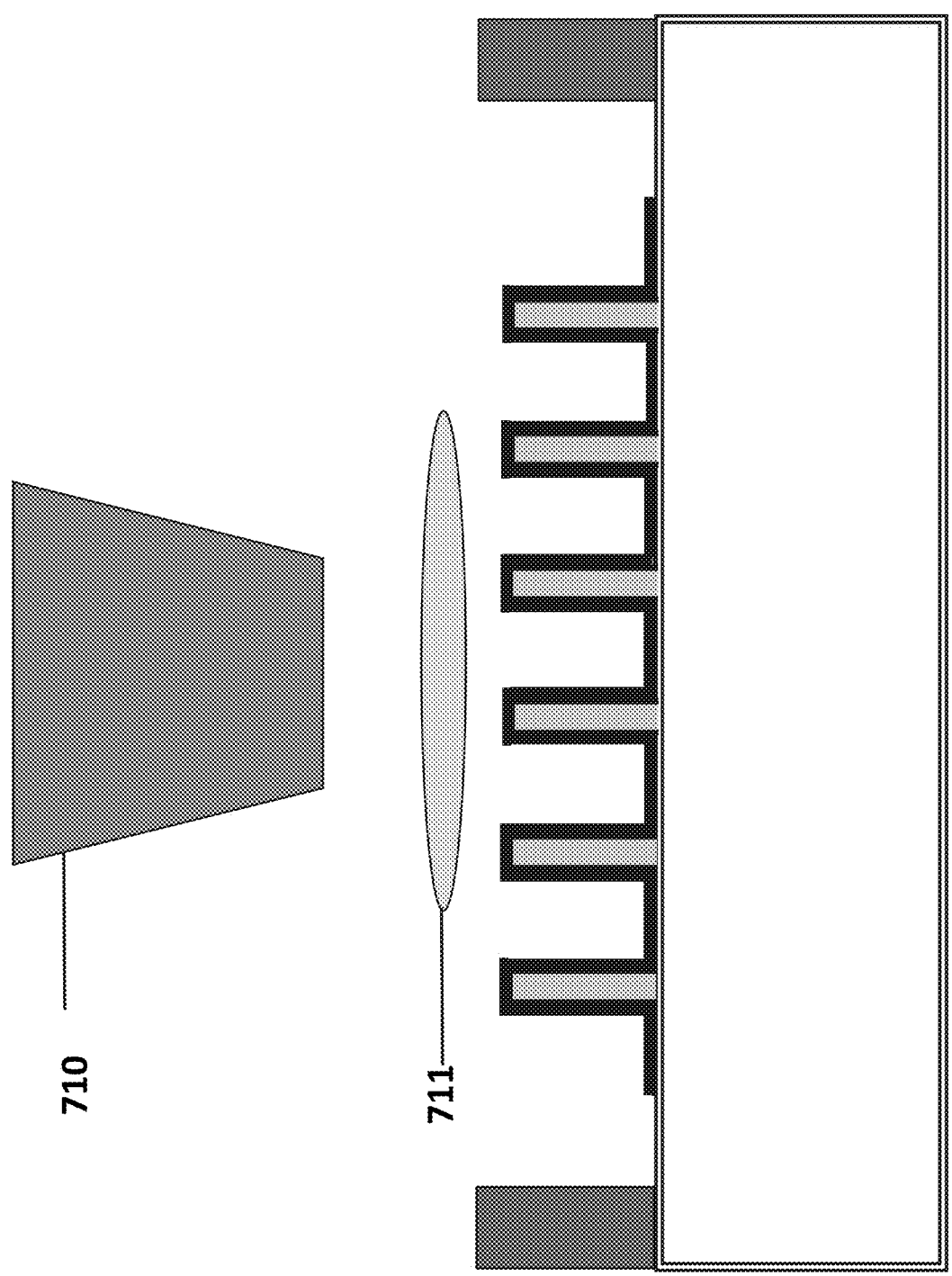
FIG. 21 demonstrates the use of fine droplet/spray deposition systems to precisely cover the integrated sensing element with controlled amounts of surface chemistry layers. For example, solenoid and/or piezoelectric controlled actuation based spray heads (710) are used to deposit, in nanoliters, precise amounts of Glucose Oxidase solutions and crosslinking agents (e.g. Glutaraldehyde) solution droplets (711) to make a glucose oxidase based hydrogel on the working electrode.
Figure 22:
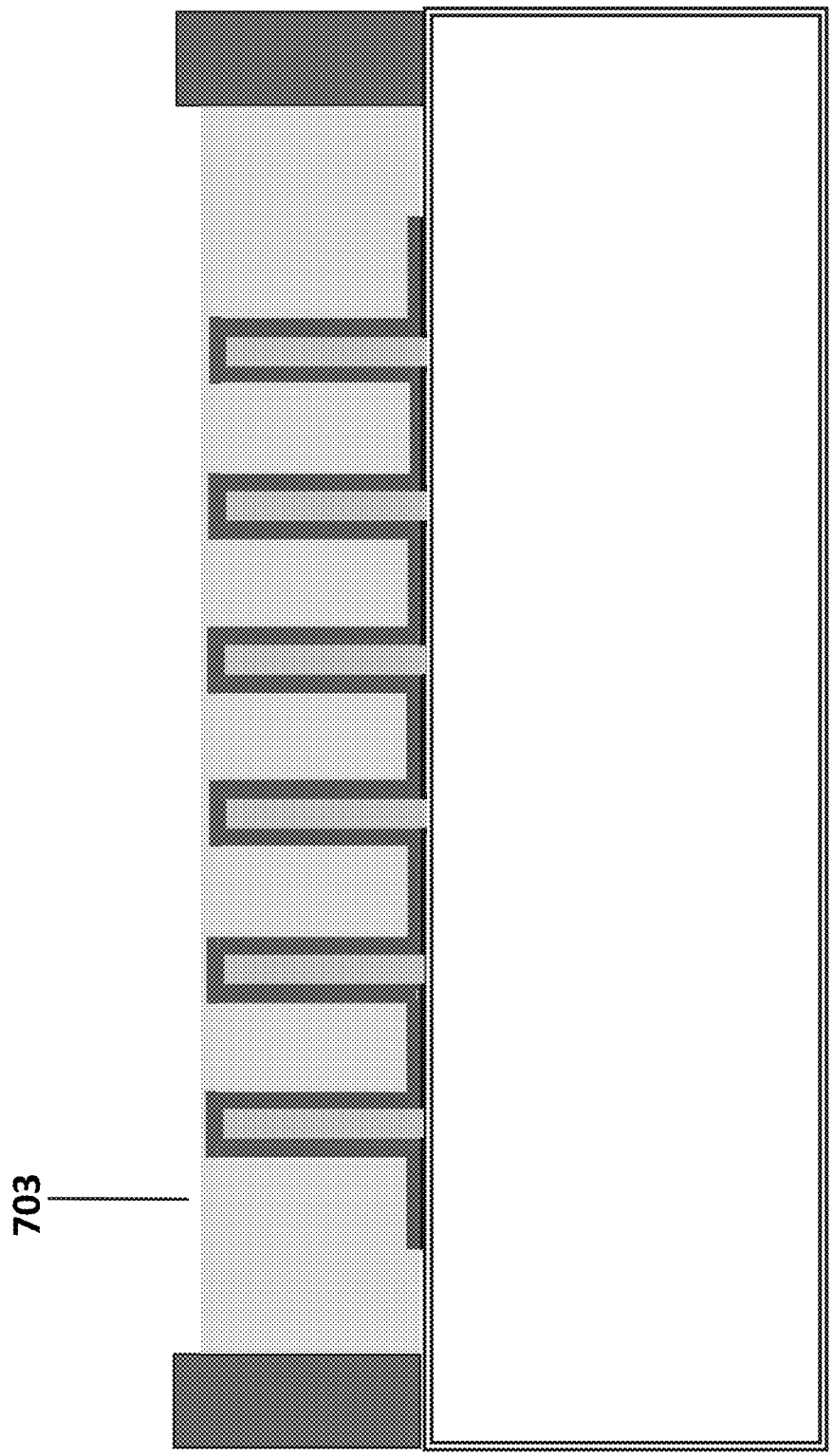
FIG. 22 demonstrates how the functional material coating (703) (e.g. a glucose oxidase based hydrogel) covers the micropatterned electrodes if proper wetting condition is achieved. One method to achieve proper wetting is use of oxygen plasma on electrode surface before applying functional coating.

In accordance with some embodiments of the invention, to selectively functionalize the sensor electrodes, a precise deposition of nano- to pico-liter of chemistry can be utilized. In one particular embodiment, the substrate can be heated or cooled and kept at a controlled temperature (e.g. 25 degrees Celsius to 35 degrees Celsius, with 25 degrees Celsius being an embodiment) in a controlled environmental chamber (e.g., to control temperature, humidity, chemical composition of the environment). Then, an accurate dispensing instrument (such as a BioJet Elite on a AD6020 aspirate dispense system by Biodot, Irvine, CA) with precise x, y, and z position control can be utilized (FIG. 20A). In accordance with some embodiments, deposition can be performed in three steps to achieve a hydrogel of repeatable and controlled hardness and composition: 1) dispensing glutaraldehyde, 2) dispensing the mixture of GOx and SA, 3) dispensing glutaraldehyde. The three deposition steps can be done almost simultaneously through the use of three dispensing nozzles as the gel formation starts happening almost instantaneously once SA and glutaraldehyde come to contact. In a different method, glutaraldehyde is only dispensed once. With the three step process, or with a process where only steps 1 and 2 are performed, controlled temperature (e.g. 25 degrees Celsius) of the sensing element electrode surface and controlled environment (e.g. 80% RH, low particle count in air) during and after dispensing helps with uniform gel formation. In embodiments where multiple sensing elements are employed on the same die, small scale dispensing allows different sensing chemistries to be dispensed on distinct working electrodes on same die, without overlap of sensing chemistries. This can be achieved using pico-droplet dispensing or through multiple photolithography steps or though nano-imprinting (utilizing a nano scale stamp to 'stamp' different hydrogels on different electrodes which are close to each other on same die).

In accordance with some embodiments of the invention, spin coating and/or spray coating can be used to achieve functionalization by applying the sensing chemistry on the sensing elements. In this method, enzyme hydrogel mixture is dispensed or sprayed on the sensor die, or entire wafer using nano-droplet dispenser, spray head, or pipette. The wafer is then spun to achieve a thin sensing layer at controlled speed (between 200 to 20000 rpm e.g., 2000 rpm being an embodiment) for set time (10 seconds to 3 minutes another embodiment being 1 minute) to achieve a thin (10-50000 nanometer thick, e.g., 2-6 micrometer thickness) layer sensing chemistry.

Stencils can be used to selectively functionalize sensing elements with different chemistries. In these embodiments, a stencil, e.g. a metal sheet with holes corresponding to sensing element surfaces, can be placed on the die or wafer. Then sensing chemistries can be dispensed, dropped, dipped, or sprayed, or otherwise deposited. In some embodiments spraying is used. Then the stencil can be lifted from the surface to leave defined sensing chemistries deposited on sensors. The stencil process can be repeated or combined with other processes to achieve a variety of chemistries.

Alternatively, wafer scale lithographic patterning can also be used. In some of these embodiments, a light-active chemical (e.g. a photoresist) can be placed on the die or wafer and patterned using light and developer as known to those skilled in the art. Then a dispensing, dipping, spraying, or any method described in surface functionalization paragraphs herein can be employed to deposit sensor chemistries on the sensors, or light-active chemical can comprise sensing chemistries mixed or reacted within. Then, the light-active chemical can be removed or replaced or chemically modified to let it stay.

Nanoimprint lithography is yet another technique that can be used for this purpose. In this case, special printing head/stamp can be used to transfer small gels on the sensing element surfaces. The gel is first formed on this stamp (which can be made using lithographic patterning or molding) using any of the methods discussed herein (e.g. nano-droplet dispensing, spin coating, spray coating). Then the stamp is placed on the desired wafer and a method is used to release the hydrogel to the sensors on the wafer. This is facilitated either by increasing gel adhesion with the sensors on the wafer (e.g. by surface activation of sensors and particularly surfaces of sensing elements in a manner such as with oxygen argon or air plasma) or by using heat/UV to create some change on the stamp which releases the gel.

Sensing elements can also be patterned by selectively activating the sensing element surfaces (e.g. with an oxygen, argon, or air plasma, or chemical modification) and sensing chemistries can be deposited using any of the methods discussed herein (e.g. nano-droplet dispensing, spin coating, spray coating). Then, the sensing chemistries can be removed (e.g. washed with deionized water, or a mixture of deionized water and detergent such as 10% (w/w) Extran (MilliporeSigma, Burlington, MA) in deionized water) such that only sensing chemistries bonded to the activated surfaces remain.

In accordance with some embodiments of the invention, a post-processed sensor wafer can be cleaned with deionized water and/or pressurized gas and dried in vacuum in vacuum oven (20-400 degrees Celsius, e.g., 40-200 Celsius; 0 to 30 mm-Hg below atmosphere, e.g., 26 mm-Hg).

In accordance with some embodiments of the invention, a cleaning and drying step can be followed by a plasma cleaning and surface activation step. In some embodiments, the sensor can be cleaned under 50-600 mTorr pressure of oxygen or air or argon plasma with a power of 75-400 W. In some embodiments, Oxygen plasma at 100-500 mTorr, with a power of 90-200 W can be used.

In accordance with some embodiments of the invention, after postprocessing and drying, wafers or sensors can be placed in a humidity controlled nanoliter dispenser equipped with an aluminum chilled plate calibrated to be able to operate at 80% RH and 25 degrees Celsius plate temperature. Each sensor's working electrode can be treated with 5 nanoliters of 1% w/w glutaraldehyde in DPBS (Sigma Aldrich, St. Louis, MO, product codes G5882, and D8537), followed by 15 nanoliters of GOx and HSA (120 mg and 100 mg respectively in 1.5 ml DPBS, Sigma Aldrich Product codes G2133, SRP6182, D8537) or 15 nanoliters of GOx and Catalase and HSA (120 mg, 1.2 mg, and 100 mg respectively in 1.5 ml DPBS, Sigma Aldrich Product codes G2133, SRE0041, SRP6182, D8537). Humidity controller can be turned on desired (e.g. @80%) RH setting just before deposition process is started and the electrodes can be allowed to dry for 5 minutes and stored in deionized water or phosphate buffer saline (Sigma Aldrich Product code P5368).

In accordance with some embodiments of the invention, the sensors' wafer can be mounted on a spin coater and glutaraldehyde can be dispensed on the wafer prior to or during spinning. Subsequently, a mixture of GOx, Serum Albumin, and in some embodiments, catalase and in some embodiments, glutaraldehyde can be placed on the wafer prior to or during spinning. Glutaraldehyde can be used to aid hydrogel formation. Catalase can be used to increase sensor longevity by mitigating excess hydrogen peroxide production during glucose sensing. In some embodiments, when it is desirable to start conversion to a hydrogel immediately before deposition on the wafer, a mixture of GOx, Serum Albumin and glutaraldehyde can be used. In accordance with some embodiments of the invention, it may be desirable to remove excess hydrogen peroxide from the hydrogel during glucose sensing, so a mixture of Catalase with GOx and Serum Albumin can be used. In accordance with some embodiments of the invention, it may be desirable to form the hydrogel after the solution is already dispensed on the electrode, by adding Glutaraldehyde to the mixture after it is dispensed on the electrode, for example, in a separate step.

In another embodiment, another layer of glutaraldehyde or another crosslinking chemical can be spun coated on the hydrogel layer to improve the hydrogel crosslinking and/or to improve adhesion of further membrane layers. In accordance with some embodiments of the invention, the solution sprayed can include equal parts of a protein solution of GOx and/or Catalase and HSA (1200 mg, 12 mg, and 1000 mg respectively in 15 ml DPBS, Sigma Aldrich Product codes G2133, SRE0041, SRP6182, D8537) and a crosslinking agent solution of 1% w/w glutaraldehyde in DPBS (Sigma Aldrich, St. Louis, MO, product codes G5882, and D8537). The parts can be sprayed simultaneously or the parts can be sprayed sequentially. In accordance with some embodiments of the invention, the placement of liquids can be performed via spraying during or prior to spinning.

In accordance with some embodiments of the invention, the crosslinking agent and or the protein mixtures are deposited on the wafer via dipping. In some embodiments of this embodiment, the sensor chips or the entire wafer can be mounted on a substrate that can be dipped vertically or horizontally in a solution of enzyme or enzymes and serum albumin and optionally glutaraldehyde. In some embodiments, the dipping solution is equal parts of a protein solution of GOx and/or Catalase and HSA (1200 mg, 12 mg, and 1000 mg respectively in 15 ml DPBS, Sigma Aldrich Product codes G2133, SRE0041, SRP6182, D8537) and a crosslinking agent solution of 1% w/w glutaraldehyde in DPBS (Sigma Aldrich, St. Louis, MO, product codes G5882, and D8537). The substrate can be dipped and dried one or more times for a total processing time ranging from 2 minutes to 2 hours depending on desired gel thickness and consistency. In some embodiments, the sensors can be dipped for one minute and dried in a chamber with 80% relative humidity for 5 minute for 10 cycles for a total processing time of 60 minutes.

In accordance with some embodiments of the invention, the sensor electrode surfaces can be activated (e.g. with glutaraldehyde or air plasma, oxygen plasma, or argon plasma) prior to the first or any subsequent dipping steps. This activation can help with adhesion of the sensor chemistry with the sensor or the previously deposited chemistry layers.

In accordance with some embodiments, the sensors can be dipped in protein solutions and glutaraldehyde solution, sequentially. For instance, if there are a variety of sensing chemistries dispensed on the sensor, and many of these produce hydrogen peroxide. Then, subsequent to the dispense coating, the whole wafer can be dip coated in catalase solution followed by dip coating in glutaraldehyde to immobilize catalase on the sensors' surface.

In some embodiments of the invention, a cleaning solution such as DPBS can be used between dipping steps in order to prevent beading of the solutions on the sensors and resulting loss of uniformity.

In another embodiment, the drying step can be done in a chamber saturated with crosslinking agent vapor, e.g. glutaraldehyde vapor, in order to aid or obviate the need for crosslinking via crosslinking agent in a dipping solution. For example, for vapor crosslinking a crosslinking agent (e.g. glutaraldehyde) in the solution may not be required. The vapors can also be applied to the electrode before dispensing GOx-Albumin mixture to enhance hydrogel adhesion to the electrode.

In accordance with some embodiments of the invention, a functional material can be coated on the sensor wafer. For example, the functional material can include a chemical or redox active material that reacts with an analyte such as Glucose Oxidase(GOx). If multiple components are required to produce the functional material (e.g. GOx, HSA, and Glutaraldehyde), each solution can be separately applied (e.g., sprayed or coated) on the wafer and the components can be allowed to interact, react and/or mixed on the wafer. Alternatively, or additionally, two or more components can be mixed prior to application to the wafer. In some embodiments several layers of the functional materials are coated on the wafer to produce a thicker final coating. In one embodiment, the sprayed solutions are a protein solution of GOx and/or Catalase and HSA (1200 mg, 12 mg, and 1000 mg respectively in 15 ml DPBS, Sigma Aldrich Product codes G2133, SRE0041, SRP6182, D8537) and a crosslinking agent solution of 1% w/w glutaraldehyde in DPBS (Sigma Aldrich, St. Louis, MO, product codes G5882, and D8537).

In accordance with some embodiments of the invention, Glucose Dehydrogenase can be used as the glucose sensing enzyme, in addition to or instead of Glucose Oxidase.

In accordance with some embodiments of the invention, the protein solutions can be precisely deposited (using a precision instrument as described above) on the sensor electrodes and spread by the use of spinning or rocking prior to or following application of crosslinking agent, or in the presence of crosslinking agent vapor.

In other embodiments that are extensions of the methods above made obvious to those skilled in the art, any of the spray, spot deposition, spin, dipping, and vapor methods are used sequentially or in parallel to deposit protein mixture or crosslinking agent.

In accordance with some embodiments of the invention, the surface can be modified or treated to enhance the bonding between underlying the solid-state sensor and the surface chemistry. For example, the surface can be treated using chemicals (e.g. glutaraldehyde) or surface plasmas (e.g. oxygen plasma) to enhance bonding. For example, patterning the surface of sensor electrodes can be used to enhance the adhesion between the gel and the underlying sensor. The surface structures and/or modifications can act as grafts for the hydrogel and also result in a stronger adhesion and/or chemical interaction between the gel and the sensor electrodes.

In accordance with some embodiments of the invention, a layer that can limit sensor response to substances that interfere with sensor operation can be applied to the surface of one or more of the electrodes before coating the hydrogel. For example, a layer of thin polymers (e.g. polyaniline) can be formed on the sensor by spinning and UV/electron beam crosslinking. For example, a layer of poly-phenylenediamine polymer can be coated on electrode surface using electrochemical deposition or UV crosslinking, before or after the enzyme coating. This allows sensor to not react to ascorbic acid or acetaminophen which otherwise can create a false signal on platinum electrodes.

In accordance with some embodiments of the invention, multiple droplets of an enzyme mixture and a crosslinking agent (e.g. glutaraldehyde) can be used to achieve thin hydrogel layer that covers the sensor electrodes.

Figure 23:
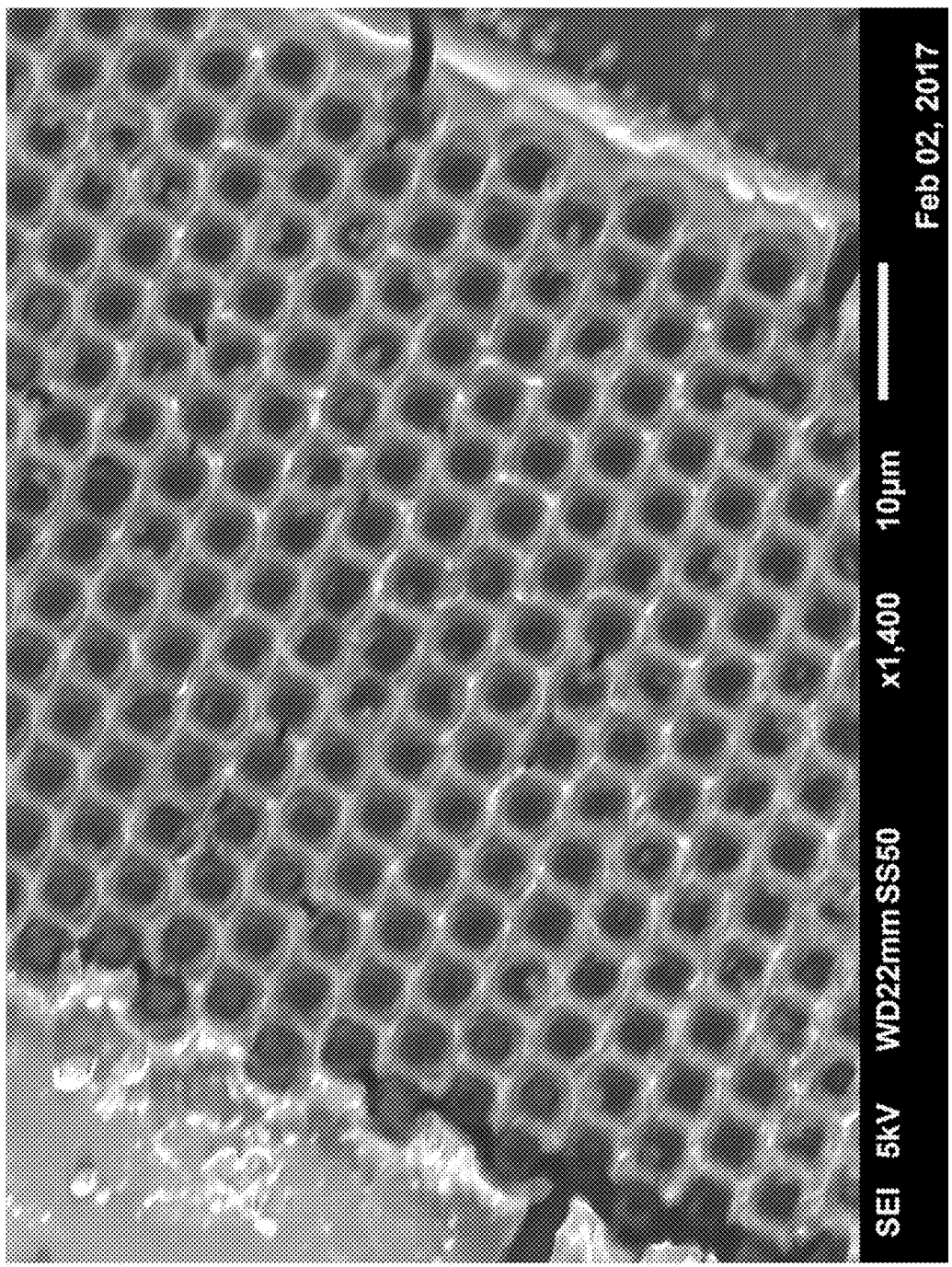
FIG. 23 shows a picture of an embodiment of micropatterned electrode coated with a functional hydrogel layer.

FIG. 23 shows an example of the working electrode after functionalization.

Membrane Coating

Before and/or after functionalization, different membrane materials can be used to protect and/or restrain the functionalization materials on the sensing element 160, and achieve a desirable signal response for a particular sensor configuration. In some embodiments of the invention, a diffusion limiting layer can be useful. For example, in the body there is 30 to 300 times more Glucose than Oxygen. If the sensing mechanism has a 1:1 stoichiometry (e.g. Glucose detection using GOx uses 1 molecule of Oxygen for every molecule of Glucose, then the sensor placed without a limiting membrane will be limited by oxygen concentration and will not be able to sense glucose for entire physiological concentration (e.g. 40-400 mg/dl). A polymer membrane can be deposited to act as a diffusion barrier that allows oxygen to go through unhindered but hinders glucose diffusion. This membrane can also act as a layer of biocompatible protective material for the enzyme layer. One example of this polymer material is polyurethane. In accordance with some embodiments, the thickness of the membrane can be in the range from 0.25 micron to 10 microns (preferably 1 to 6 microns). The thickness of membrane can be selected in order to balance sensor response linearity, sensitivity and response time (time delay between change of analyte concentration in sensed medium and change in sensor response). Thicker membranes provide increased linearity while increasing response time and decreasing sensitivity. Thinner membranes provide increased sensitivity and decreased response time with decreased linearity. As a person of ordinary skill would appreciate, the thickness of membrane can be selected based on the analyte sensing functional material and the desired sensitivity and response time.

Specific membrane materials and construction can be used to further improve sensor performance. In one embodiment of the invention, a composition of polyurethane and silicone [5], can act as a filter to regulate diffusion of glucose and as an oxygen recycling membrane as well as providing a biocompatible material. Oxygen recycling would improve the efficacy of the sensor, while the biocompatibility would allow the sensor to work for longer.

Figure 24:
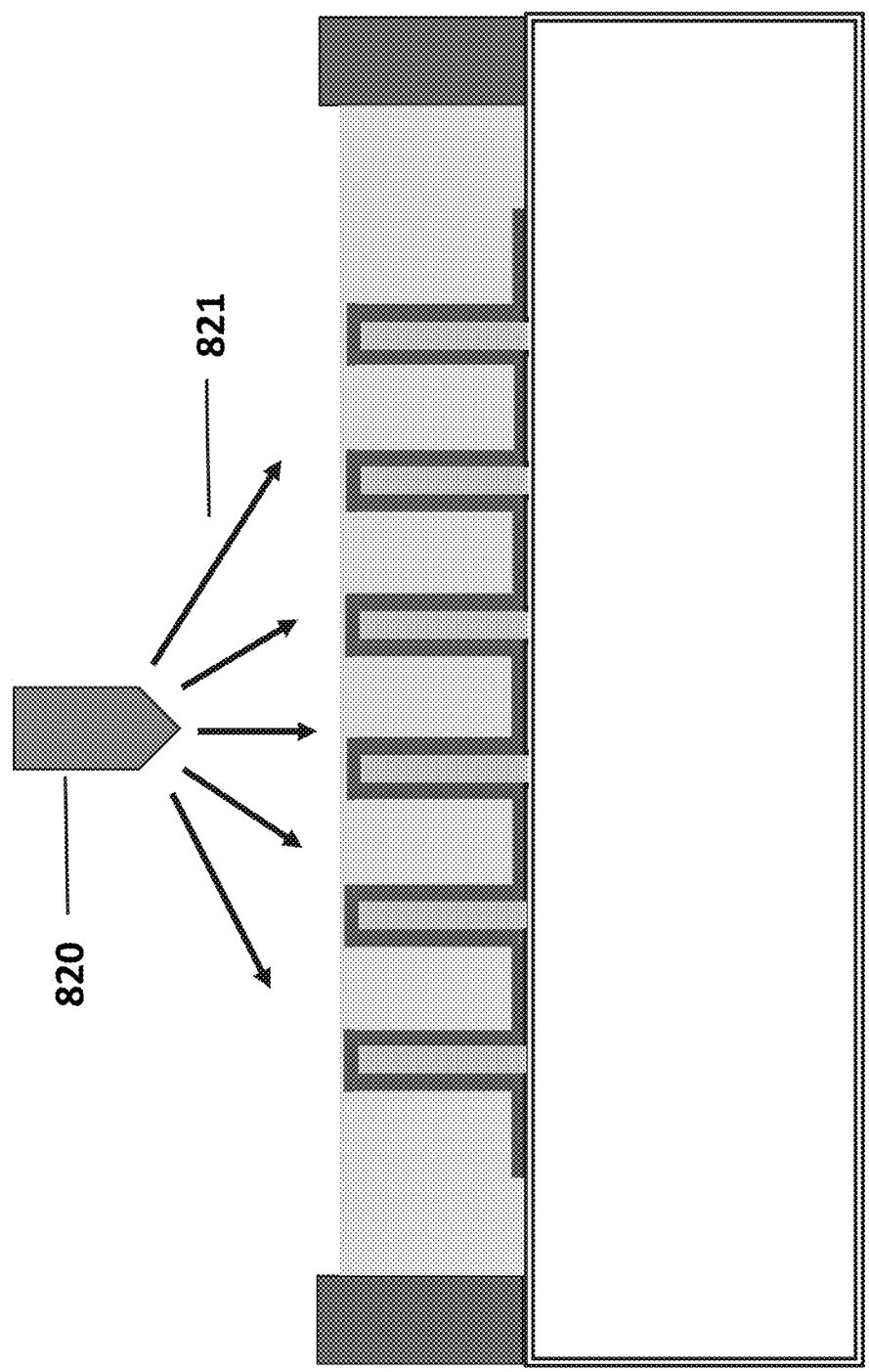
FIG. 24 shows use of spray coating to make a film (stack of one or more thin films) on sensor surface, using an appropriate spray head (820) which showers microdroplets (821) on a small area of the sensor.

To cover the sensor uniformly and minimize sensor to sensor and batch to batch variation, such membranes can be deposited on the sensor through spotting (droplet coating), spraying or through wafer-level spin coating (FIG. 24). Membranes can also be deposited on the backside of the wafer to increase biocompatibility. Another method to uniformly deposit membranes is to employ spray coating with a special instrument utilizing overlap between multiple depositions to achieve a uniform overall thickness.

In accordance with some embodiments of the invention, 1% PurSil from DSM in THF (DSM Biomedical, Exton, PA and Sigma Aldrich, St. Louis MO) is loaded into an Air-jet spray coating unit (BioDot, Irvine, CA). A single coat of 1.25 microliter/cm is applied at 9 PSI pressure on sensor area, with dispensing height and aperture optimized for each coating unit installation. The wafer is dried in a vacuum oven at 35 degrees Celsius and 25.6 mm-Hg pressure for an hour and in ambient conditions for at least 12 hours (overnight). A second coat is applied and sensors are dried with the same parameters. The sensors are allowed to stabilize in PBS (Sigma Aldrich, St. Louis MO) for 72 hours and characterized for analyte response.

Figure 25A:
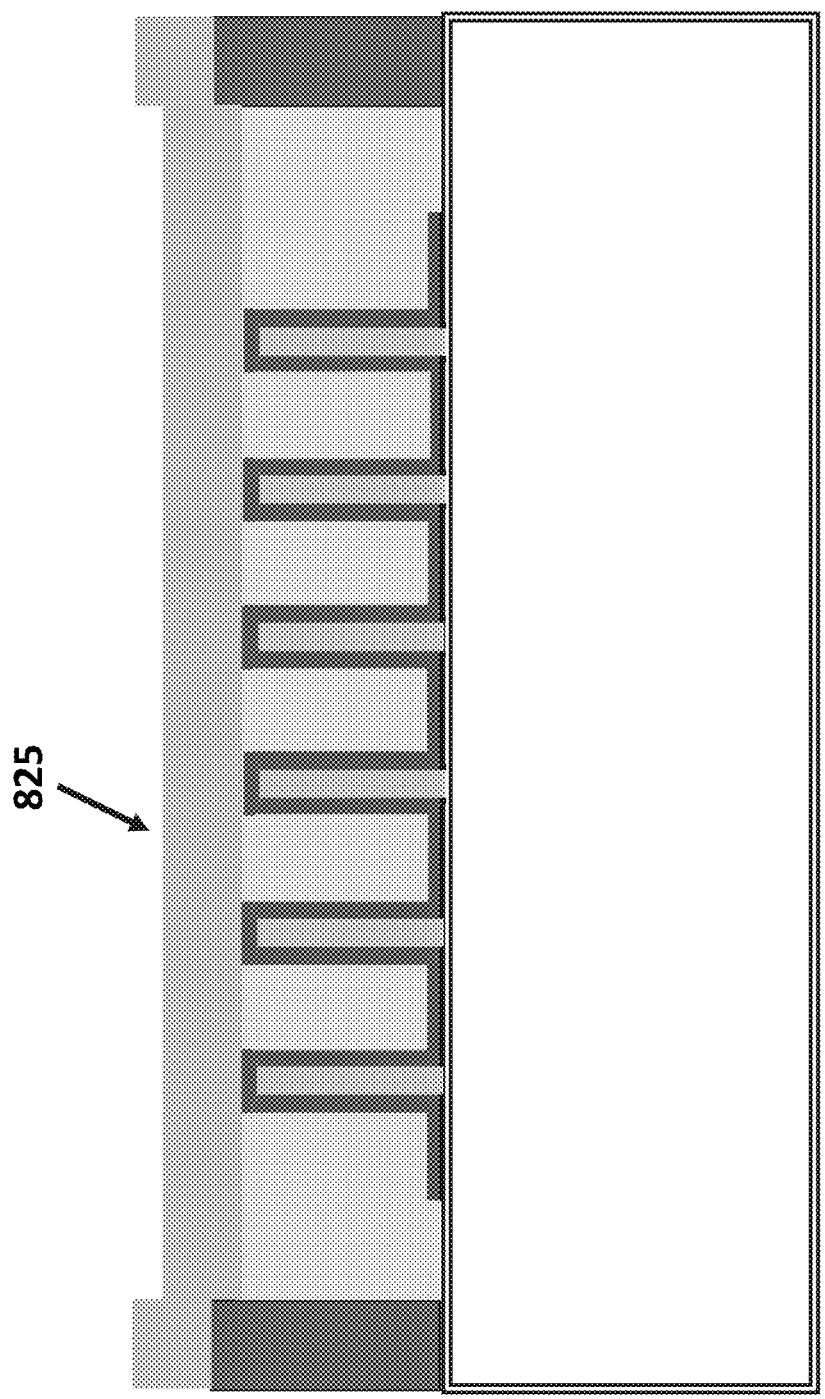
FIG. 25A shows an embodiment wherein a planar film 825 is provided by the coating method.
Figure 25B:
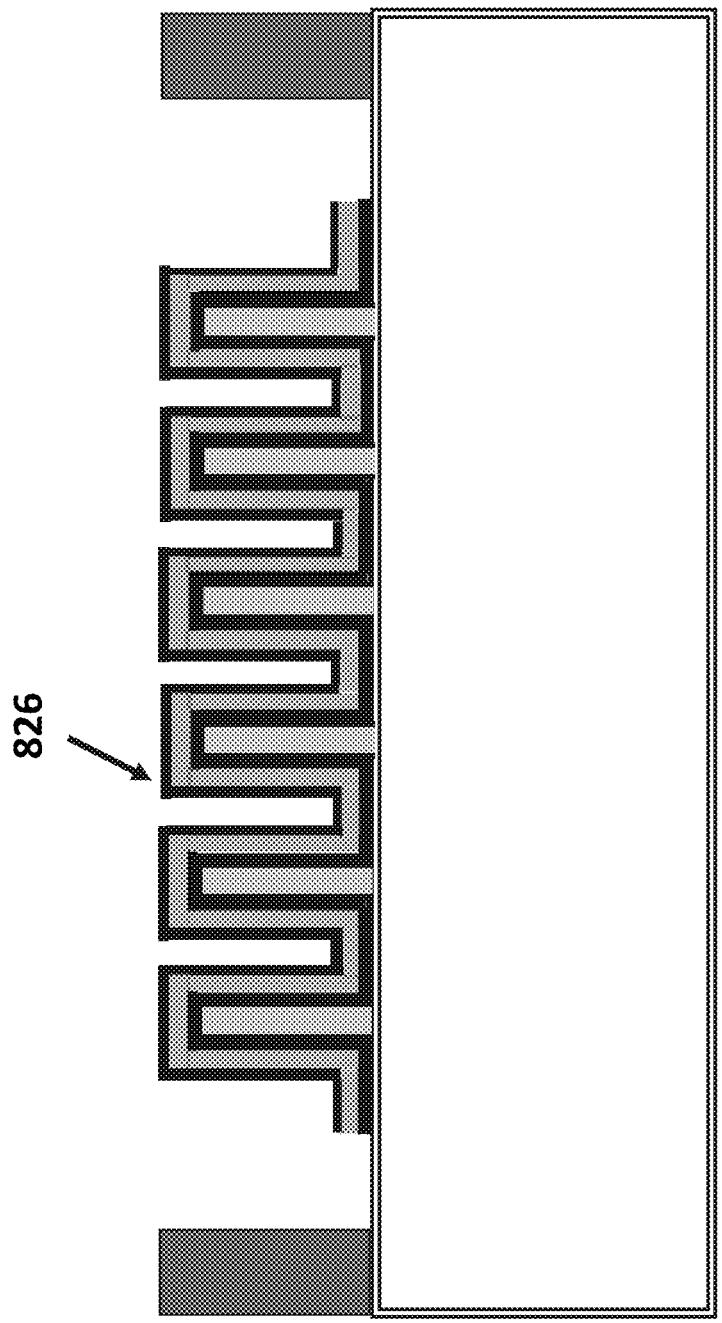
FIG. 25B shows an alternative embodiment wherein a conformal film 826 is provided by the coating method. Coating (825) can be made by simple deposition. More conformal coating 826 can be achieved by adjusting the parameters of spray coating and/or by utilizing spreading techniques, for example using spinning to achieve a thinner layer.
Figure 25C:
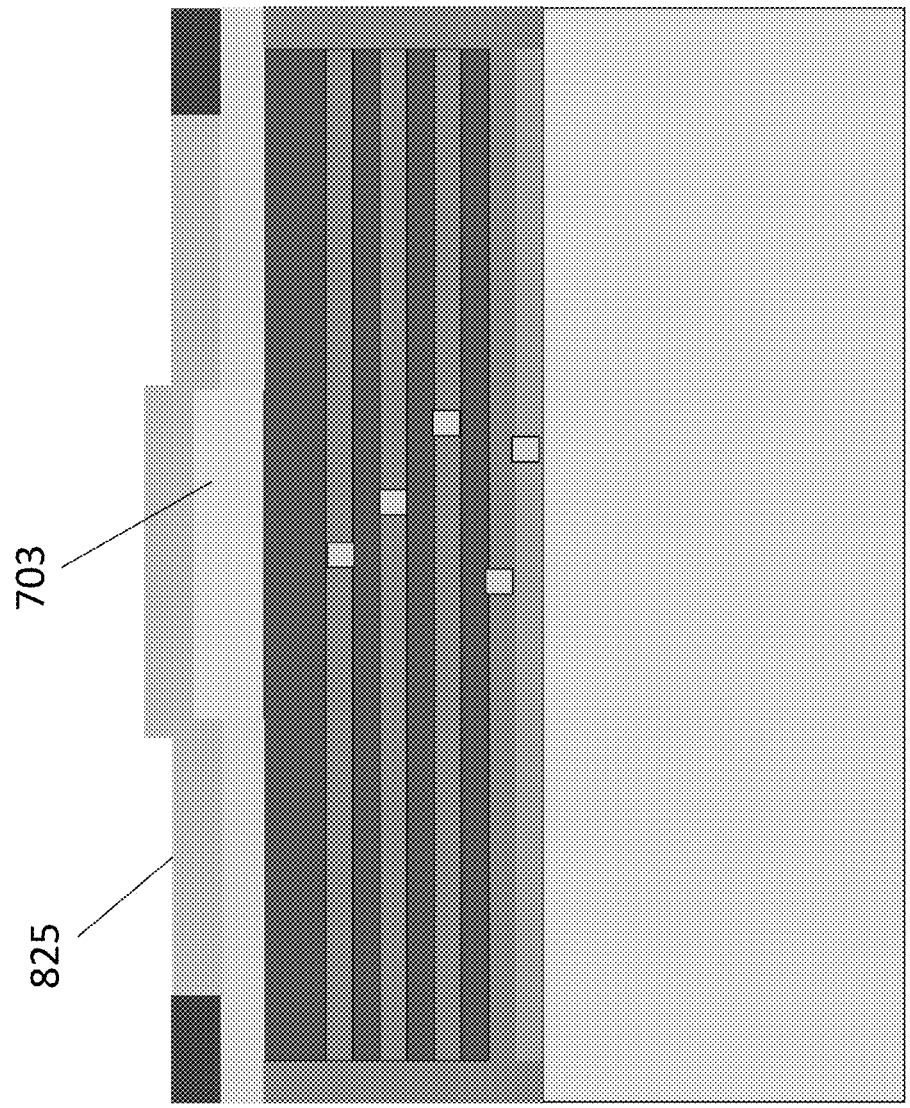
FIG. 25C shows a front cross section view of a CMOS sensor after coating with hydrogel (703) and polymer coating (825).

In some cases, both hydrogel and polymer membrane can conform to the pattern of underlying pillars to result in patterned layers, as shown in FIG. 25B. Such patterning can allow for faster response time (lesser delays) but may have shorter lifetime compared to sensors with thicker hydrogels and polymer layers.

To improve biocompatibility of the system, the sensor can be coated with a biocompatible material. For example, the biocompatible material can be poly-HEMA. In some cases, a copolymer of a biocompatible material can be made with Polyurethane to coat the device in a single step.

Adhesion between the membrane coating and the underlying hydrogel, or between layers of coating, can be facilitated by use of chemicals (e.g. silanes, aldehydes) and/or physical processes (e.g. corona treatment, oxygen plasma, gas plasma, mechanical roughening).

The membrane coating can also be patterned to reduce cell attachment. This patterning can be done using oxygen plasma or using nanoimprint lithography (bio-stamping).

Another example of polymer coating is use of interference rejection layers that can be coated on the electrodes before or after surface functionalization. These layers can be coated using spraying, dip coating, electrochemical coating, spin coating. In accordance with some embodiments of the invention, a coating including o-phenylenediamine can be used for rejecting Ascorbic acid and/or Acetaminophen in glucose sensing applications.

Implanted sensors can be attacked by the foreign body or immune response of the body. This can be mitigated by incorporating coatings that inhibit response and/or mitigate the effects and decrease this foreign body response. It is known to those skilled in the art that hydrophilic or superhydrophilic surfaces result in less response, drugs such as dexamethasone or nitric oxide limit such response, and reactive oxygen species quenching agents such as platinum limit the effects of such response.

In some embodiments of the invention, drugs that inhibit adverse response by the body (e.g. dexamethasone, nitric oxide) can be mixed, encapsulated, or chemically included in the functionalization layers and/or membrane layers, in a way that allows slow release of the drugs throughout the functional lifetime of the sensor.

In some embodiments of the invention, the outermost membrane can be patterned to achieve superhydrophilic surface.

In some embodiments of the invention, metals such as Titanium and/or Platinum can be incorporated or deposited on membranes to increase hydrophilicity, achieve superhydrophilicity, and/or mitigate effects of reactive oxygen species resulting from body response.

In some embodiment of the invention, dexamethasone (1% w/w) is mixed into the polyurethane layer, polyHEMA layer is patterned with nanoimprinting to achieve a superhydrophilic surface, and 2 nm thick Ti/2 nm thick Pt are sputtered on the surface to quench reactive oxygen species while maintaining superhydrophilicity and porosity.

Sensor Fabrication, Processing and Packaging

Sensor fabrication starts with submitting the chip design files to a semiconductor manufacturer (e.g. TSMC (Taiwan), ON Semiconductor (Phoenix, AZ)). The standard semiconductor fabrication processes generate standard wafers of certain sizes (e.g. 12 inch diameter wafers). After semiconductor manufacturing, the wafers can be processed to replace the top metal with a more suitable material (e.g. platinum) in other manufacturing facilities called MEMS foundries (e.g. Rogue Valley Microdevices (Medford, OR), X-Fab (Belgium)).

In order to reduce the dimension of the device, the original thick (e.g. 750 μm) semiconductor wafer can be thinned down (e.g. to 50-250 μm) through mechanical grinding, chemical and/or mechanical polishing or chemical etching (e.g. Xenon Difluoride (XeF2) etching from backside). This step can be done before or after surface functionalization and membrane chemistry deposition. At this thickness, the silicon becomes more flexible and can improve the integration of the sensor implant within the surrounding tissue and reduced foreign body response. Thinning and/or grinding can be performed by a thinning and grinding facility (e.g. Advanced International Technologies, Quick-Pak).

Next, different types of dicing methods (saw, laser, etc.) along with some polishing methods can be used to realize any desirable shape (e.g. circular, rectangular, oval). Laser cutting can be used to form rounded edges on the final diced device and help reduce potential implantation injury and subsequent foreign body response. Sidewall polishing after dicing can also be used to reduce and remove sharp edges. Further, coating with biocompatible membranes can also be used to minimize any sharp edges.

Laser dicing can be accompanied by appropriate environmental condition (e.g. oxygen flow) to create thin layer of thermal oxide on sidewalls during dicing. Steam can also be used to generate a wet oxide on sensor sidewalls.

Figure 26A:
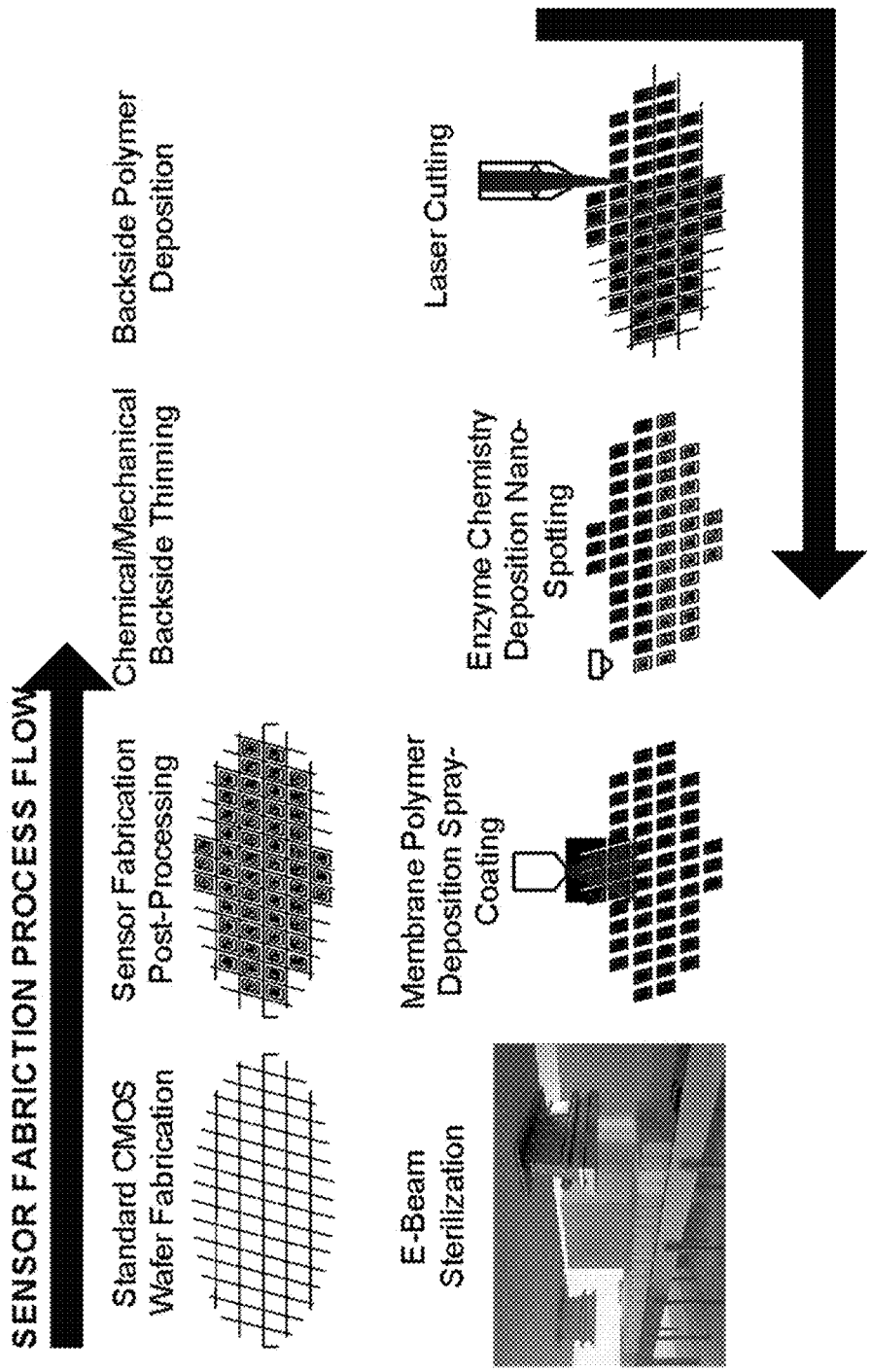
FIGS. 26A and 26B shows complete process flows to make large number of devices using wafer scale processing steps.
Figure 26B:
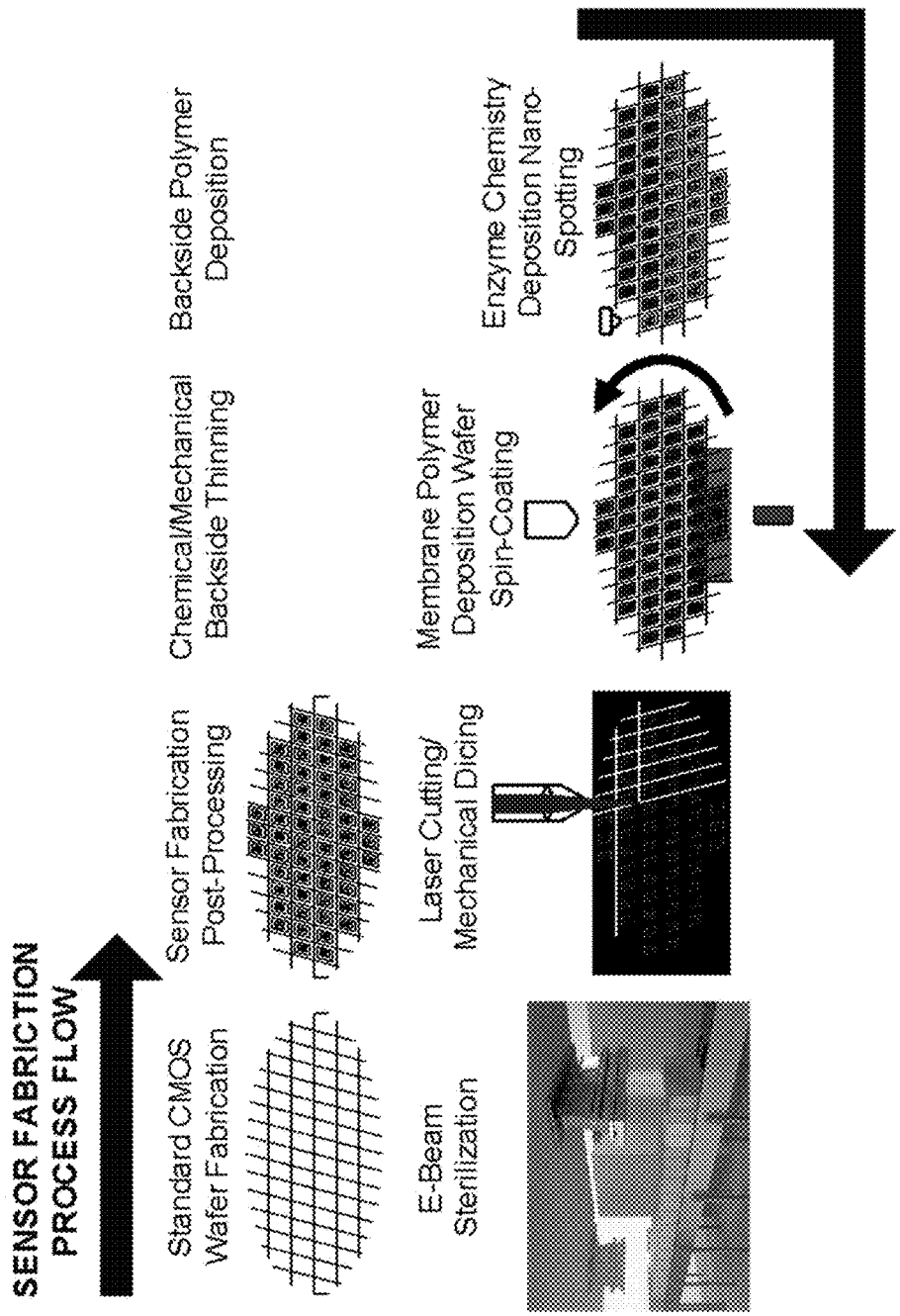

In accordance with some embodiments of the invention, the wafers can be thinned down after post-processing and coated with suitable polymer layer(s) (e.g. Polyurethane, Silicone, Polyurethane-Silicone copolymers, Parylene) on the backside (using spin/spray/plasma coating). Coating services are available from, for example, PolyPico, and MicroFab. Then the wafers can be diced. Next, sensor on the diced wafers can be functionalized with an enzyme layer without separating the diced sensors from the dicing tape. Finally, the sensors can be covered with polymer layers on the top side using spray coating or dip coating process enabling both the sensor top and sidewalls to be covered. Such coating services are available from, for example, DSM (The Netherlands). The final processed devices can be picked and placed inside the applicator device and the entire assembly can be sterilized (e.g., by Synergy Health (San Diego, CA)). A diagram of the complete process flow is shown in FIG. 26A. In accordance with some embodiments of the invention, the sensors can be functionalized and polymer coated before being diced (see, FIG. 26B). Either one of these processes, or a hybrid process where the devices are partially separated in an intermediate step (e.g., scribing the surface (e.g., mechanically or with a laser), stealth dicing) and separated afterwards, can generate functional devices.

In some embodiments, immediately after dicing or after one or multitude of processing steps are performed, the sensors can be placed on tape that would be the final packaging bottom. This way the sensors can be processed in a reel-to-reel fashion rather than wafer by wafer fashion. All of the aforementioned processes can be performed on a reel tape, or regular tape. This reduces equipment complexity and cost by eliminating the need for precision stages. This way all sensor production steps following metallization and dicing can be performed on a single assembly line.

In order to sterilize the implant before embedding it inside the body, conventional methods of sterilization (e.g. steam, Ethylene Oxide) can be utilized. Electron-beam sterilization can be used to sterilize the sensor as well as the applicator once the sensor is pre-loaded in the applicator. The underlying electronics is designed to be resilient to e-beam radiation. The enzyme chemistry can be characterized to calibrate for any changes in the enzyme chemistry response due to sterilization.

In one embodiment, 18 kGray of e-beam irradiation is sufficient to sterilize the sensor without impeding its function. Sensors can be placed inside the applicator and then the whole assembly can be sterilized.

Figure 27:
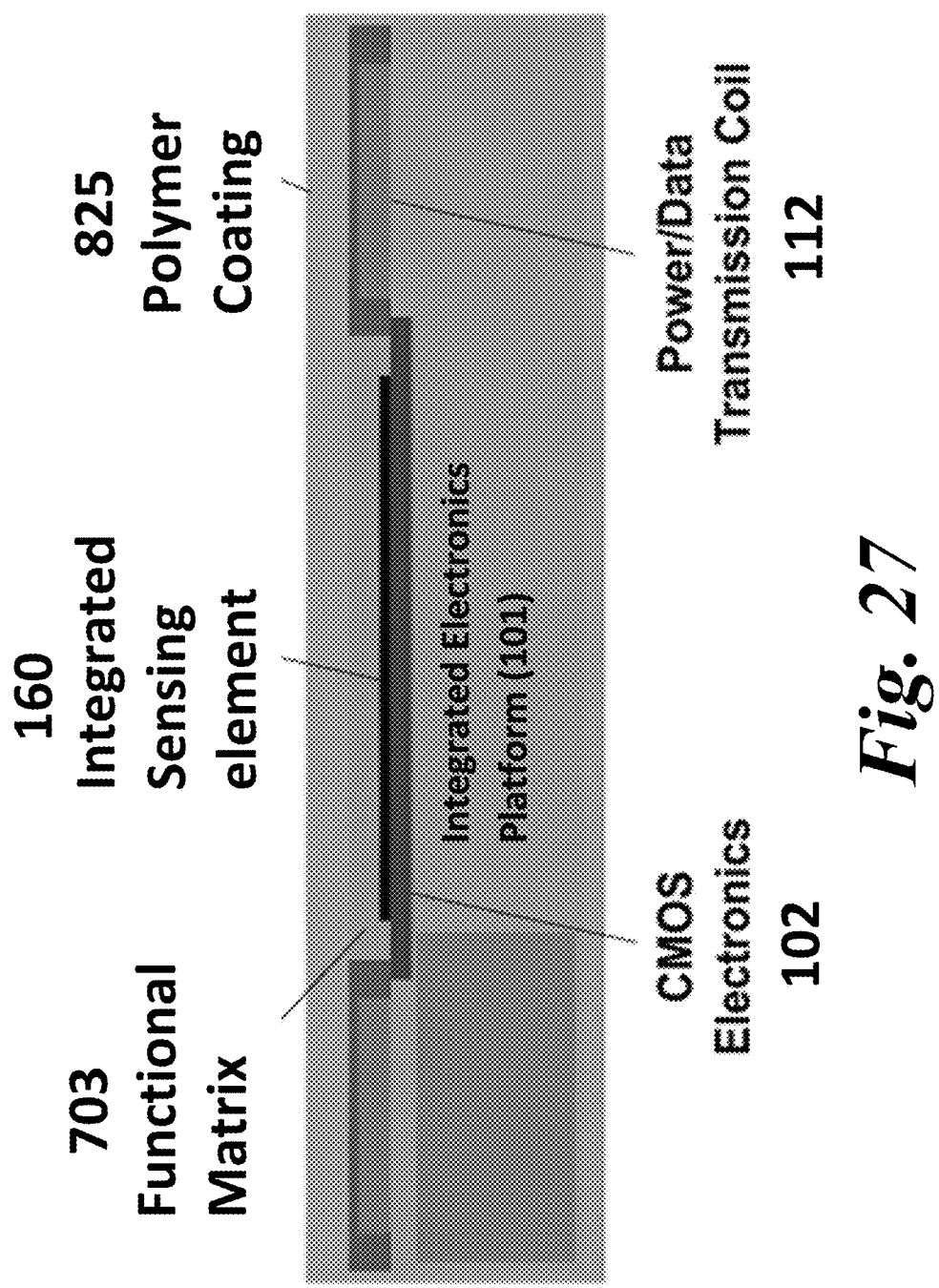
FIG. 27 provides the components of a completely processed wireless sensors including the integrated electronics platform (101) housing CMOS electronics (102) as well as Antenna for Wireless Power transfer and wireless telemetry (112), the integrated sensing element (160), the functional matrix 703, the polymer coating 825.

The final sensor after the processing is depicted in FIG. 27 and have several components including a semiconductor (e.g. Silicon) substrate (210), An integrated coil/antenna (211), a surface coating on the sensor (212), for example a Glucose oxidase hydrogel, and one or more layer of other desirable material(s), for example polyurethane, poly-HEMA, drug or functional metal loaded membranes, as outer coating on all or parts of the device Sensor Form Factor For in vivo sensing, the wireless sensors need to be implanted with minimally invasive methods to minimize the damage to the host which is important to minimize the reaction by the host body. Designing these systems in accordance to the specific implantation site (tissue orientation etc.) can further help in reducing the post-implantation complexities. For example, for implantation in biological tissues, these should be shaped to minimize sharp edges to minimize implantation damage and hence immune system response. System can be shaped to be longer in one dimension and much smaller in other dimensions. This makes it possible to inject it using very small needles and also it can fit within the subcutaneous or subdermal space more easily. Having holes through the system can also help since fluids can flow through the sensor allowing better perfusion and signal and may reduce local inflammation. Such holes could also be used as natural anchors or suturing or string apertures for sensor stability with respect to the tissue, and/or grabbing handles for extraction. In some cases, a latching mechanism or texture can be designed in the device to facilitate extraction. Minimizing the device thickness and coating it with a biocompatible soft material can also make it more flexible and reduce the implantation damage, especially for deep implants.

A precisely controlled minimization of solid-state sensor size also reduces its noise levels and increase the Signal-to-Noise ratio (SNR), thus improving sensitivity of sensor. Furthermore, integrated design minimizes contact resistance and capacitance between the sensor and the electronics, further enhancing sensitivity and SNR of the sensor.

Real-Time Sensing

Interfacing these systems with their environment is much easier due to their small size. For example, the small size of the whole system along with shaping it minimizes scar tissue formation in the body to a point where it only helps in keeping the system position stable but doesn't significantly isolate it from accessing body fluids. This allows real-time measurement of important analyte (e.g. metabolic Glucose level) for critical applications requiring instant changes to be reported as soon as possible (e.g. for hypoglycemic diabetic patients). Local heating or special biomaterials can further enhance biocompatibility to help with this even more. The small size also allows placement of the device closer to or within blood vessels and/or organs. An intermediate device can be used to power the device if deeper implantation is required for some applications.

Transceiver Design

The external transceiver 2 is used to power the implantable sensing device and to communicate with it. The transceiver 2 can also be used to relay the sensor data to a smart device (e.g. a smartphone) for further data processing.

Figure 28:
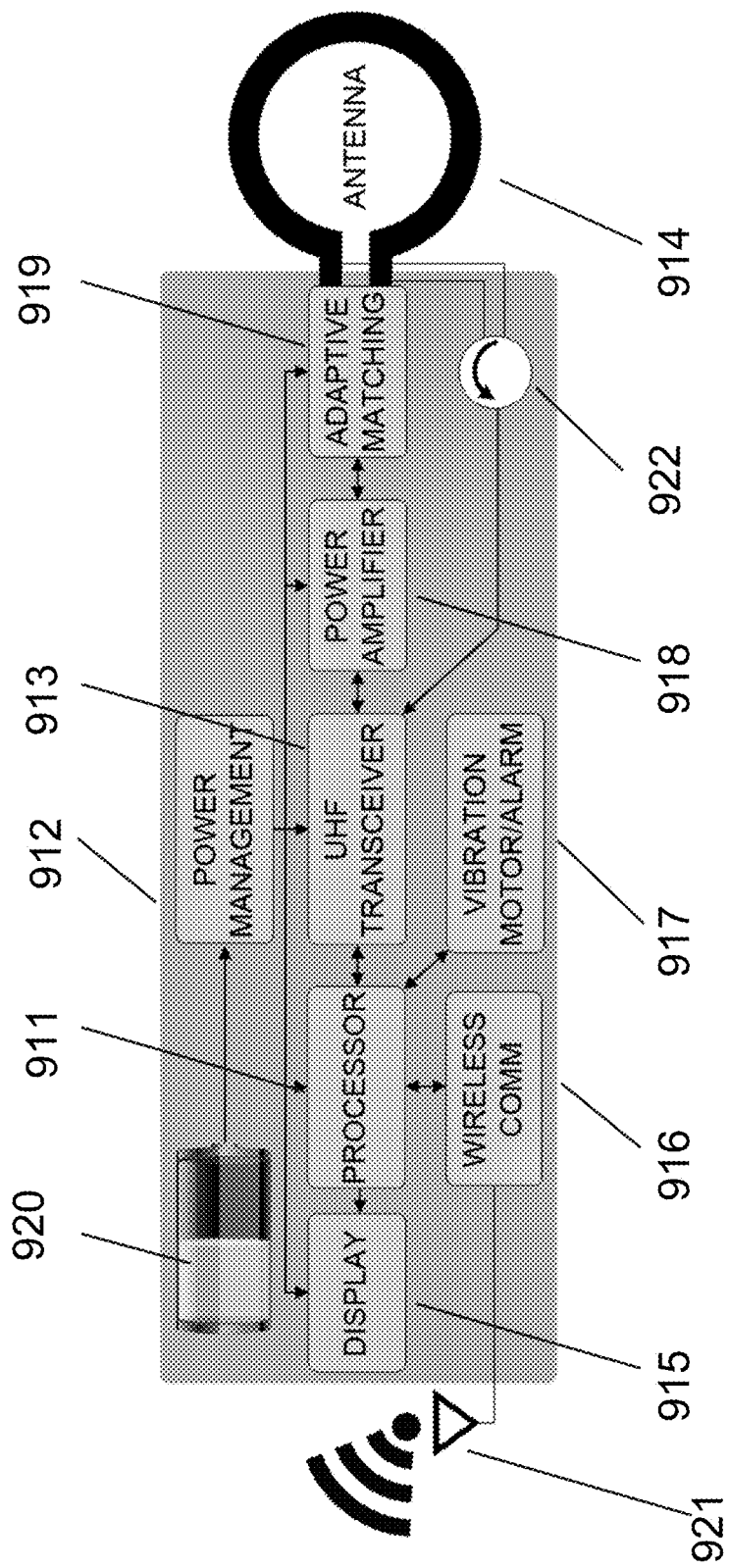
FIG. 28 provides embodiment of the design for a wireless transceiver 2 consisting of a Microprocessor 911, Power Management Unit 912, UHF Transceiver 913, an Antenna 914, an optional smart display 915, a low-power wireless communication chipset 916 (e.g., Bluetooth Low Energy), a vibration motor and alarm 917, a power amplifier 918, an adaptive matching network 919, a rechargeable battery 920 and an antenna for low power wireless communication 921.

The external transceiver 2 can be used to power sensor 1 and to communicate with sensor 1 to received data from and send data to sensor 1 before and after sensor 1 is implanted. In some embodiments, the external transceiver 2 can be used to generate a strong magnetic field to power to the sensor. The external transceiver 2 can send data in the form of commands to the sensor and receive data in the form of data signals (e.g. glucose data) from sensor 1. In accordance with some embodiments of the invention, the external transceiver 2 can include one or more RFID based UHF chipsets to create the appropriate signals for power and communication. A simple microprocessor or a microcontroller can be used to control system operation and to program the UHF chip. FIG. 28 shows a diagram of an example of a wireless transceiver according to some embodiments of the invention. A printed circuit board (PCB) can be used to make a system with all components on the same electronic platform to function as the transceiver 2. One or both of thick (rigid) and thin (flexible) PCB technologies can be used, depending upon the application.

In accordance with some embodiments of the invention, the antenna 914 on the transceiver 2 can be designed (e.g., by shaping the conductor in a concentric or circular topology) to create a strong near-field magnetic field and to minimize far field radiations, when the power transfer is based upon inductive coupling. For far field power transfer, the design criteria are reversed. Circular metal coils can be used as efficient structures for near field inductive coupling. LC matching can be used to couple the antenna 914 with the input from the UHF chip 913. Backscattering can be used to communicate a signal from chip to the transceiver 2. A circulator 922 can be used to separate the backscattered signal from strong transmitted signal. The backscattered signal can be passed through a synchronous detection circuit on the UHF chip 913. The baseband signal can be passed to a sampling circuit, and the output is passed to decision logic on the processor 911. The transceiver uses a low power wireless communication antenna 921 to communicate with other devices (e.g. a smartphone). The transceiver is powered by a rechargeable battery 920. The transceiver may use a small display 915 and a vibration motor/audio alarm unit 917 to alarm the user if and when required (e.g. in hypoglycemia).

Error correction schemes can be employed to minimize the error. Simple methods include majority polling. Parity bit based designs and more advanced error correction codes can be used as well. Different types of modulation schemes can be employed for this communication. To be compatible with the EPC Gen2 RFID standard CRC-16 coding can be employed at the implant.

The transceiver can be worn adjacent to the sensor site (e.g, on or over the sensor) such that power can be transferred to the sensor and data can be received from the sensor. Different locations in the body can be used as sensor site. The transceiver can be worn as a wearable device (e.g., a watch or a patch) held in place by adhesives or straps to allow for convenient long term use.

The transceiver can wirelessly communicate the data to a hub or smart device (e.g., a phone, a tablet or a special separate device). In accordance with some embodiments, the hub or smart device can be connected (either by wire or wirelessly) to a cloud server via a network (e.g., the Internet, a private network such as virtual private network (VPN), or a public network).

In some embodiments, a smart watch, mobile phone, or similar device from Apple, Samsung and/or other sources can be programmed to be used as an external transceiver 2.

Smart Device Design

A smart device 3 can be used to communicate with the external transceiver 2 on one end and to connect it to the internet (e.g., the web or a private network) on the other end to send user data to the cloud 4 for storage and analysis. The smart device 3 can be implemented on standard smart phones, tablets, and personal computers (e.g., via one or more software applications) or it can be implemented in a separate device (e.g., an embedded computer, a personal computer) based upon user requirements.

Applicator

Owing to the small size of the device, implantation can be done using injections rather than surgery. This can help reduce the cost and the foreign body response due to surgery and can allow the implantation to be carried out by less trained personnel or the patient.

To implant the device in the proper depth and with the appropriate angle, an applicator device can be used. The applicator can consist of a plastic assembly and metal parts, and can be manually driven, spring driven, or electronically driven, or driven by any other means known in the art.

A plastic assembly can be used to hold the device and allow controlled angle and position of implantation. A metal part can be used to create a path in the body to transfer the sensor in desired tissue, (e.g., subcutaneous or subdermal, depending upon application) and can also be used to control device movement path for implantation.

The metal part, implantation tube, can be blunt or can be shaped like a needle and can have a circular or an oval cross-section (through pressing a standard needle), or any other hollow cross section.

Figure 29:
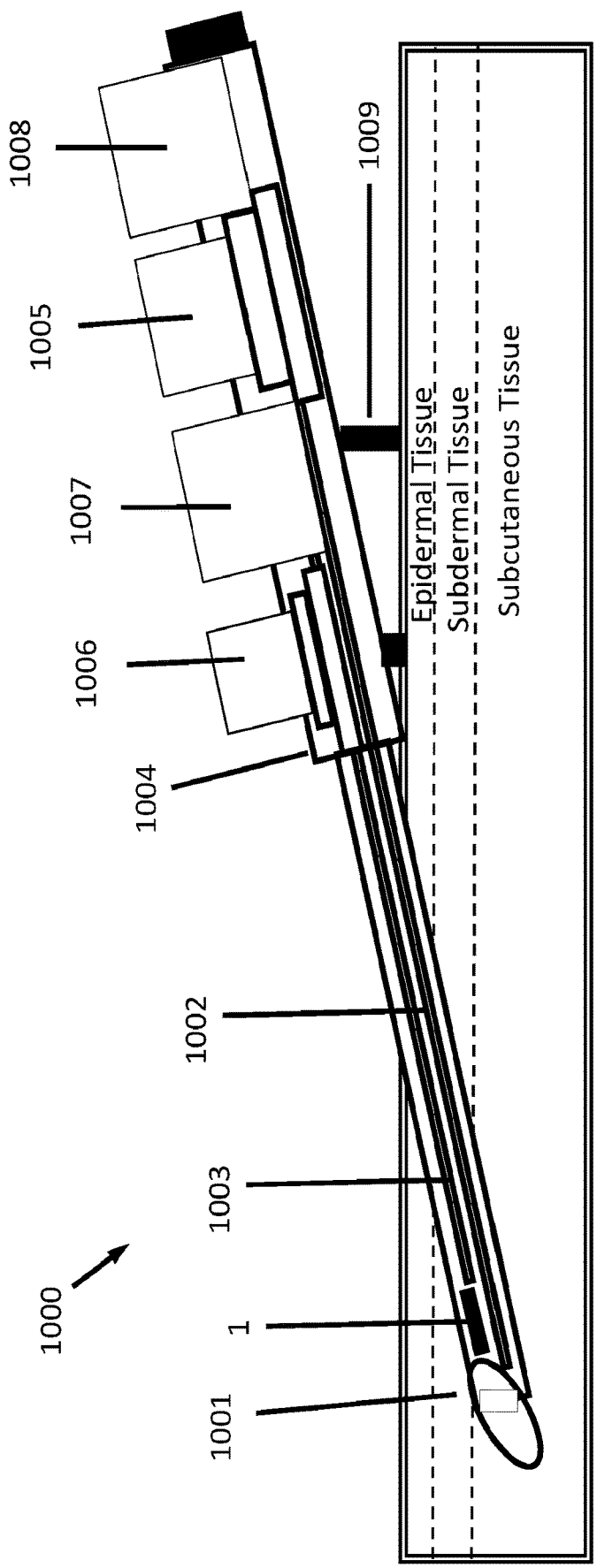
FIG. 29 provides a design of an injector (1000) to embed the sensor (1) under the skin. The injector (also known as applicator) comprises different components such as a needle (for example non-coring) (1001), a metal plate (1002) for the sensor to rest on, a plunger (1003) to push the sensor, a syringe-like body (1004) to allow controlled motion of applicator's parts, a sliding head (1005) to move the metal plate (1002), a sliding head (1006) to move the needle, a set of stoppers (1007 & 1008) for appropriate motion. And angle control stubs (1009).
Figure 30:
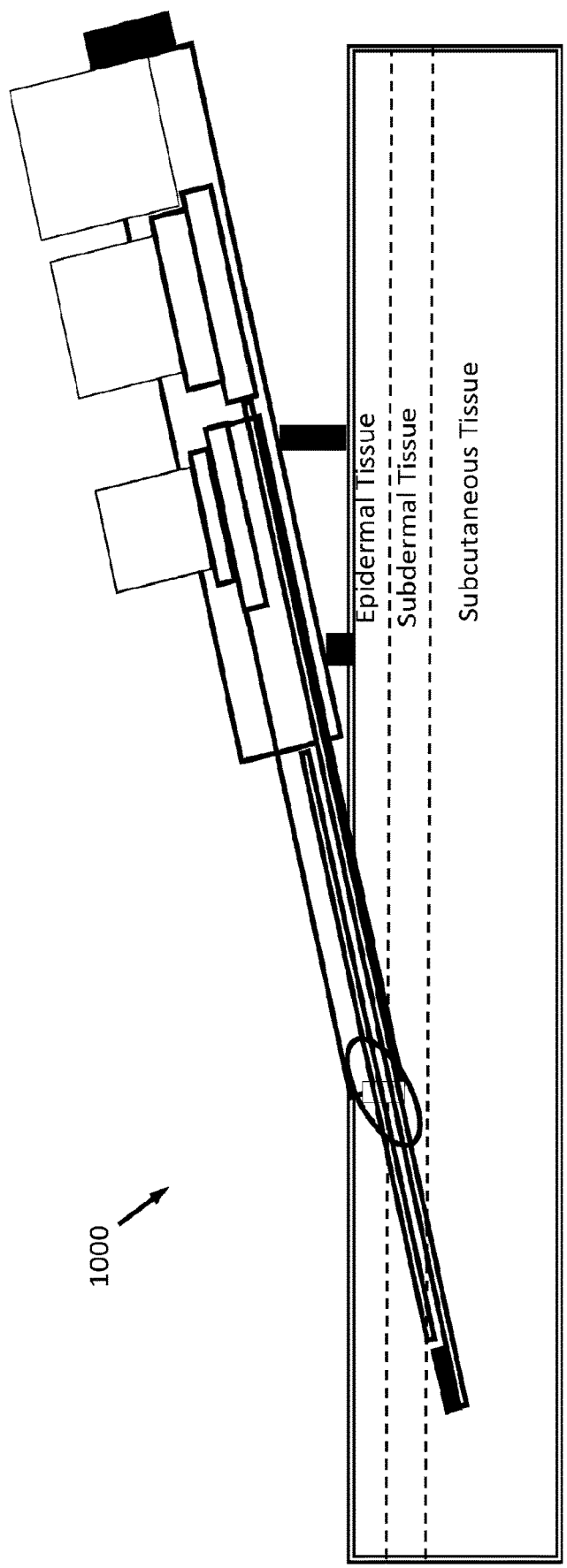
Figure 31:
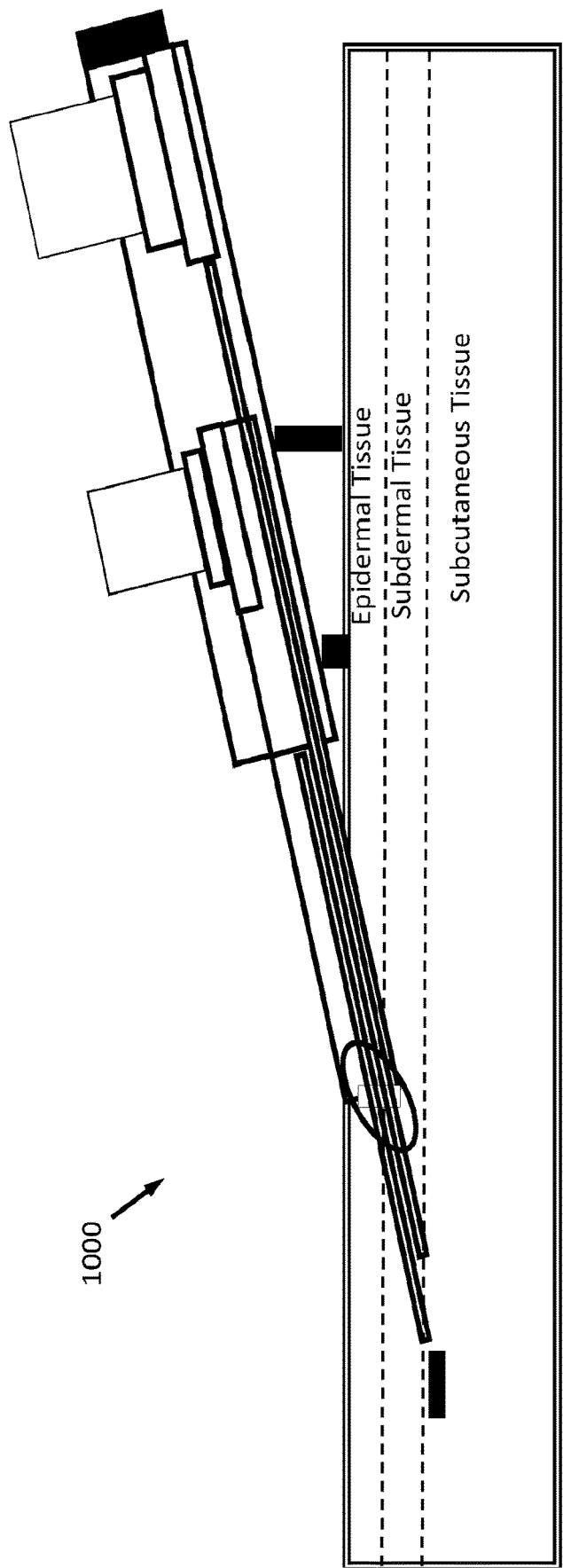
Figure 32:
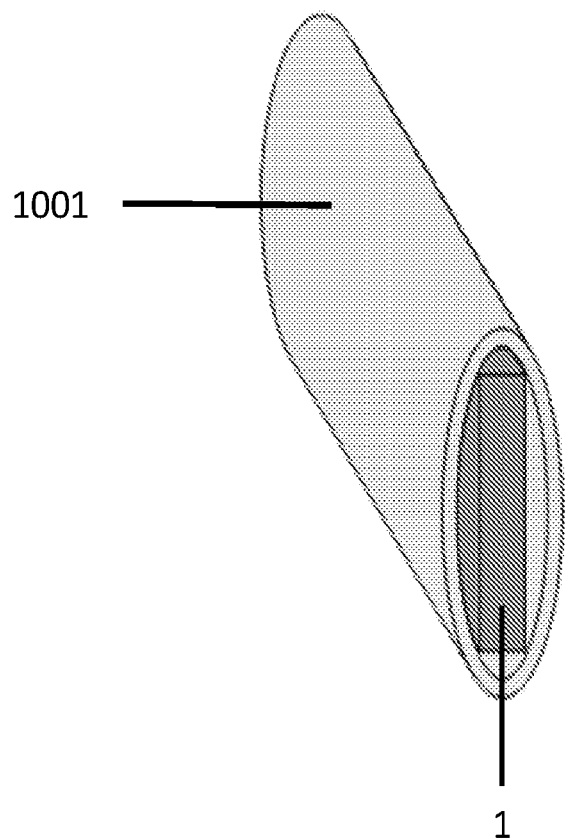
FIG. 32 shows how a smaller needle (1001) can be pressed to fit a sensor (1) larger than the inner diameter of a standard mechanical gauge of the needle.

The implantable sensor 1 can be pre-loaded into the applicator 1000 and then using a shaft or plunger is pushed forward for deployment, or the tube is retracted leaving the implant in place (FIGS. 29-30-31 depicts this operation).

In some embodiments, the implantation tube and/or the parts of the remainder of the applicator is filled with sterile liquid or pressurized gas in order to prevent flow of tissue fluids inside the device and/or to wet and clean the implantation site and/or to deliver drugs during implantation.

An embodiment of the applicator includes a sharp needle that surrounds the blunt implantation tube. In this embodiment, the sharp needle makes an initial incision followed by implantation via blunt implantation tube. Another embodiment of the device utilizes a cutting tool such as scalpel or lancet within the device for an initial incision, while another embodiment relies on an incision made manually with such cutting tools prior to usage of the applicator.

In another embodiment, sensor can be implanted using thin metal parts which create minimal damage to in-vivo tissue. In this embodiment, the sensor is placed in a cutout on a thin metal plate with thickness comparable to that of the sensor (middle plate) shaped to accommodate the sensor and minimize skin irritation. There can be either or both a top and bottom plate that protects the sensor and prevents premature deployment of the sensor. The sensor is then deployed. In one embodiment of this embodiment, the metal parts can be formed using stamping in order to minimize volume cost.

In another embodiment, similar to the embodiment above, the sensor is held in an implantation device between at least a top plate and a bottom plate, and zero or more side plates. The sensor is delivered inside the body by pushing the plate assembly through the skin, thereby making an incision, or through an incision already made. Then the sensor is dislodged by removing any of the plates and/or moving the assembly or pushing the sensor out and away with a plunger. In the case of three or less plates, the sensor orientation can be rotated such that there are two side plates and at least zero bottom or top plates. The sensor can be oriented within the plates such that the sensor 1, and especially the sides that comprise sensing elements, is protected from abrasion during the implantation.

Sensor Extraction

If required, extraction can be performed using skin biopsy punch, or skin incision followed by removal using fine forceps. Alternatively, an instrument can also be used to extract the devices. Such a tool can comprise a lancing mechanism, a micrograbber, along with a soft microfibre to minimize tissue damage during extraction. These sensors can have an X-ray/Ultrasonic/Infrared footprint and hence can be precisely located using these alternative means, in addition to location by the wireless transceiver. Moreover, sensors can also be visually located since they offer significant contrast compared to skin tone. Additional illumination can be used to help with visual location. An instrument can be used, after incision, to grab the device with a mechanical structure that matches the sensor shape and texture (see latching on sensor form factor section above). This can minimize the difficulty that may be faced by manual removal. Several devices can be removed at same time under same local anesthesia.

Figure 33:
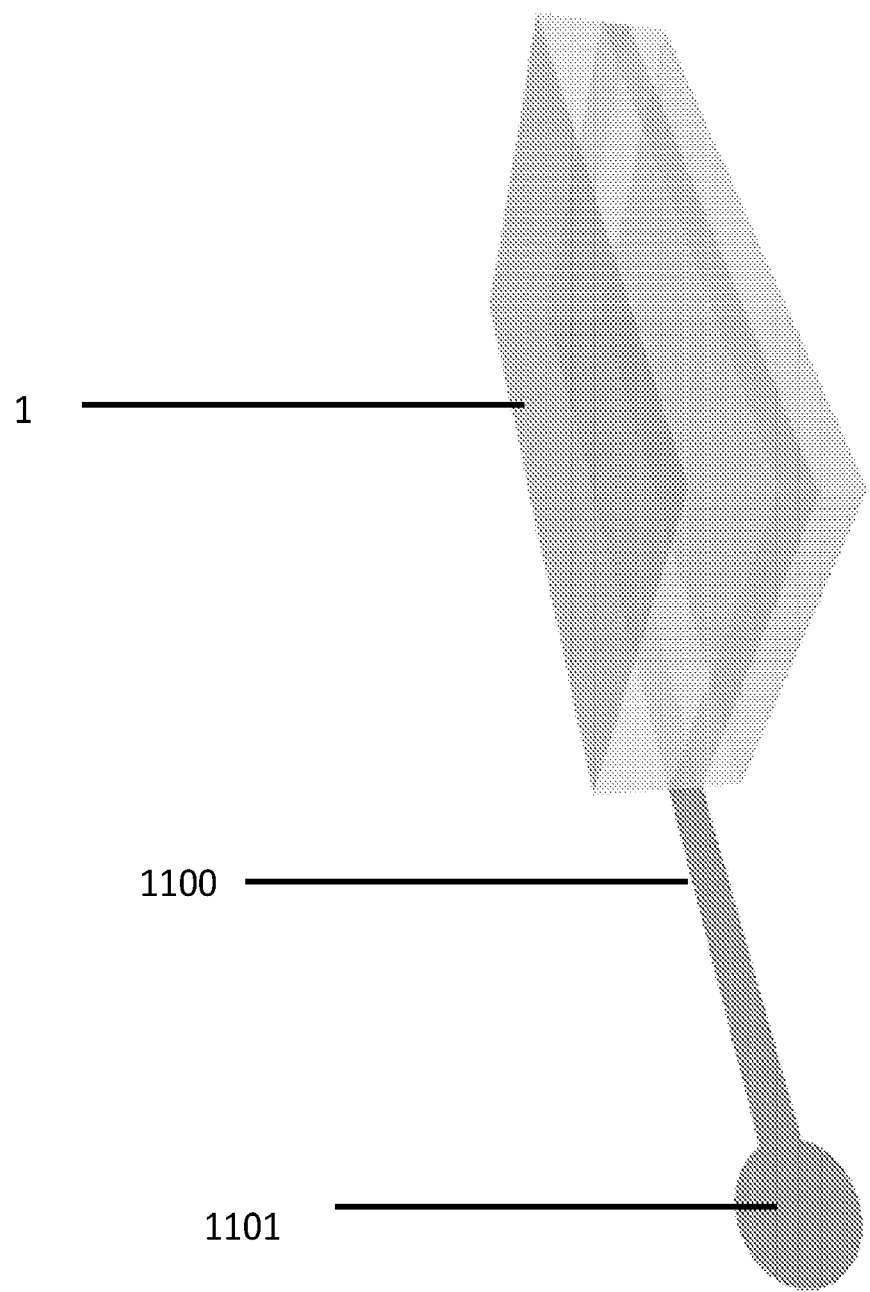
FIG. 33 shows how a sensor can be affixed to a biocompatible thread (1100) and a small disk (1101) for easier extraction. The disk can be solid or have at least one hole or and can be grabbed to pull the sensor out. The disk can be made of soft biocompatible material. The disk can be totally implanted under the skin (closer to insertion site) or can be placed just over the skin close to the insertion site. The sensor can be extracted using the thread, e.g. by pulling on the thread by hand or any implement, or using a device such as a scalpel or custom extraction device to make an opening on the skin and either using the thread and/or other imaging or illumination to guide the extraction device to the sensor, or remove the sensor by pulling the thread.

In another embodiment, the sensor can have a piece of thread attached to it (e.g. wrapped around it, looped through a hole in the sensor, affixed using a bonding agent cast within a PDMS or some other biocompatible material casing along with the sensor through injection molding, casting, or similar procedure) with a loose end with a certain feature that can be easily recognized and grabbed during extraction (FIG. 33). The sensor can then be pulled along with the thread.

In another embodiment, the thread can be transcutaneous and pulled from outside the body.

In some embodiments the thread is made of ultra-high molecular weight polyethylene (e.g. by Teleflex). In some embodiments, the thread is a tape, or is a cast polymer formed with injection molding, casting, or similar procedure.

Embodiments of the various aspects described herein can be illustrated by the following numbered paragraphs.

1. An implantable sensor comprising,
   an implantable biocompatible integrated circuit connected to a sensing element;
   wherein, the sensing element senses one or more analytes and generates a signal, representative of an analyte concentration, received by the implantable biocompatible integrated circuit;
   wherein implantable biocompatible integrated circuit includes
      an analyte signal acquisition and processing unit that receives the signals from the sensing element;
      a wireless power harvesting unit connected and providing power to the analyte signal acquisition and processing unit; and
      a telemetry unit connected to the analyte signal and processing unit and transmits data representative of said analyte concentration.

2. The implantable sensor as in paragraph 1, wherein the sensing element includes one or more electrodes.

3. The implantable sensor as in paragraph 2, wherein each electrode comprises a conductive surface and at least one conductive surface is surface patterned to increase a contact surface area of the electrode.

4. The implantable sensor as in paragraph 2 or 3, wherein the electrodes are made using lithographic processing and a suitable deposition method like electron beam deposition, thermal evaporation or sputtering.

5. The implantable sensor as in any one of paragraphs 2-4, wherein the electrodes are coated with one or more functional materials to achieve desired design specifications, using nano-dispensing, spray, dip or spin coating methods.

6. The implantable sensor as in paragraph 5, wherein the functional material is a hydrogel and is created through deposition of components including;
   a cross linking agent,
   an enzyme, and
   a proteinaceous material;
   wherein the deposition of two or more the components can be sequentially or simultaneous, including pre-mixing of two or more components for simultaneous deposition; and
   wherein one or more components can be deposited one or more times in more than one deposition step.

7. The implantable sensor as in paragraph 6, further comprising a compound or co-protein to improve the longevity, decrease foreign body response, or increased sensor signal.

8. The implantable sensor as in paragraph 7, wherein the co-protein is catalase.

9. The implantable sensor as in any one of paragraphs 6-8, comprising one or more of glutaraldehyde, glucose oxidase (GOx), and Human Serum Albumin (HSA).

10. The implantable sensor as in claim 1, wherein the sensing element includes;
   two or more working electrodes, and
   a counter and a reference electrode.

11. The implantable sensor as in any one of paragraphs 1-10, wherein at least a part of the implantable sensor is coated with one or more polymers and compounds providing biocompatibility, diffusion control and anti-fouling to one or more of the sensor components.

12. The implantable sensor as in any one of paragraphs 1-10, wherein the implantable biocompatible integrated circuit and the sensing element are an integrated device.

13. A wireless sensing system comprising:
   an implantable sensor comprising,
      an implantable biocompatible integrated circuit connected to a sensing element;
      wherein, the sensing element senses one or more analytes and generates a signal, representative of an analyte concentration, received by the implantable biocompatible integrated circuit;
      wherein implantable biocompatible integrated circuit includes
         an analyte signal acquisition and processing unit that receives the signals from the sensing element;
         a wireless power harvesting unit connected and providing power to the analyte signal acquisition and processing unit; and
         a telemetry unit connected to the analyte signal and processing unit and transmits analyte data representative of said analyte concentration;
      a wireless transceiver configured to generate a wireless power signal;
      wherein the wireless transceiver is positioned adjacent to the implantable biocompatible sensor such that the implantable sensor receives the wireless power signal from the transceiver, and
         the transceiver receives analyte data from the sensor.

14. The wireless sensing system as in paragraph 13, further comprising a smart device that communicates with the wireless transceiver and displays the gathered data and provides smart analysis and predictions based upon data.

15. The wireless sensing system as in paragraph 14, further comprising a cloud based system connected to the smart device.

16. The wireless sensing system as in paragraph 15, wherein the smart device receives data from the implantable sensor, process the said data, displays it to a user in a user-specified format and relays the data along with other data to a cloud based system.

17. The wireless sensing system as in any one of paragraphs 13-16, wherein the sensing element senses glucose in a subject.

18. A method of measuring an analyte concentration comprising;
   implanting a wireless sensor in contact with analyte containing tissue of a subject,
   positioning the transceiver adjacent to the wireless sensor, wirelessly powering the sensor using the wireless transceiver, sensing of one or more analytes in the tissue of the subject with a sensing element of the wireless sensor and generating an analyte signal representative of the analyte concentration, determining analyte data as a function of the analyte signal, and transmitting the analyte data representative of the analyte concentration to the wireless transceiver.

19. The method of paragraph 18, wherein the transceiver transmits the data to a smartphone or hub.

20. The method of paragraph 18 or 19, wherein implanting comprises deploying the wireless sensor using an applicator, the applicator comprising;
- a plastic body to allow applicator handling,
- a plastic-metal assembly to move the sensing device, and
- a non-coring needle configured to pierce the subject skin and for embedding the
- sensor underneath the skin with minimal tissue damage.

21. The method of any one of paragraphs 18-20, wherein the analyte comprises glucose.

Each of the following References is hereby incorporated by reference herein, in its entirety:
1. U.S. Pat. No. 9,173,605 B., "*Fabrication of Implantable Fully Integrated Electrochemical Sensors*", by Muhammad Mujeeb-U-Rahman, Meisam Nazari, and Mehmet Sencan, Axel Scherer.
2. U.S. Pat. No. 9,011,330, "*Implantable Vascular System Biosensor with Grown Capillary Beds and Uses Thereof*", by Akram Sadek, Muhammad Mujeeb-U-Rahman, and Axel Scherer.
3. U.S. Patent Publication no. 2013/0211213 A1 "*Digital ASIC Sensor Platform*", Andrew DeHennis, and Arthur E. Colvin, Jr.
4. U.S. Pat. No. 9,006,014, "*Fabrication of Three-dimensional High Surface Area Electrodes*", Muhammad Mujeeb-U-Rahman, and Axel Scherer.
5. U.S. Pat. No. 5,882,494, "*Polyurethane/polyurea compositions containing silicone for biosensor membranes*", by William P. Van Antwerp.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. An implantable sensor with a thickness between 50 to 150 microns, a length between 1500 to 3000 microns, and a width between 400 and 1000 microns with a polymeric coating, said sensor comprising:
an implantable integrated circuit connected to a sensing element, said sensing element comprising at least two or more working electrodes, and one counter and one reference electrode, all made using lithographic processing, wherein each electrode comprises a conductive surface and at least one conductive surface is surface patterned to increase a contact surface area of the electrode, wherein each working electrode is connected to a respective potentiostat;

wherein the sensing element senses one or more analytes and generates two or more signals from the two or more working electrodes representative of the one or more analytes concentration, said signals received by the implantable integrated circuit;

wherein the implantable integrated circuit includes:
A) an analyte signal acquisition and processing unit that receives the two or more signals from the sensing element representative of the one or more analytes concentration;
B) an LC resonant unit comprising a tunable capacitor connected to an antenna;
C) a power management unit, said power management unit connected and providing power to the analyte signal acquisition and processing unit, said power management unit comprising a calibration machine, a low voltage low drop out regulator, a rectifier, and a voltage detector, wherein the voltage detector measures a rectifier output voltage $V_{RECT}$ and the calibration machine maximizes output voltage $V_{RECT}$ from the rectifier through alignment of the resonant frequency of the implantable sensor with a wireless transceiver by modulation of the tunable capacitor; and
D) a telemetry unit connected to the analyte signal and processing unit LC resonant unit, and power management unit which transmits A) data representative of said analyte concentration and, B) measured rectifier output voltage $V_{RECT}$, wherein the implantable integrated circuit is formed in CMOS on a single CMOS substrate and the sensing element is formed on top of the same CMOS substrate to generate a monolithically integrated sensor.

2. The implantable sensor as in claim 1, further comprising a hydrogel containing glucose oxidase (Gox), wherein the antenna is formed into the CMOS substrate.

3. The implantable sensor as in claim 2, wherein the antenna is made in one of a top 1 to 3 metals of the CMOS substrate and formed from aluminum.

4. The implantable sensor as in claim 1, wherein the reference, the counter, and the working electrode(s) are isolated from each other by silicon nitride.

5. The implantable sensor as in claim 1, wherein the surface patterning comprises pillars formed by CMOS, wherein the pillars have a height between 2 microns to 5 microns, and wherein the pillars are separated by the same distance as their size.

6. The implantable sensor as in claim 1, further comprising a hydrogel containing glucose oxidase (Gox), wherein the hydrogel has a thickness between 2 to 6 microns.

7. The implantable sensor as in claim 1, wherein the telemetry unit implements CRC16 coding for error correction.

8. The implantable sensor as in claim 1, wherein the polymeric coating is a polyurethane membrane, and wherein the polyurethane membrane thickness is in the range of 0.25 to 6 microns.

9. The implantable sensor as in claim 8, wherein a second membrane is placed over the polyurethane membrane and the second membrane is hydrophilic.

10. The implantable sensor as in claim 1, wherein the multiple potentiostats are connected to a single analog to digital converter.

11. The implantable sensor as in claim 10, wherein the outputs of the multiple potentiostats are time multiplexed into the single analog to digital converter.

12. A method of measuring an analyte concentration comprising;

implanting the implantable sensor according to claim 1 into contact with analyte containing tissue of a subject, positioning the transceiver adjacent to the implantable sensor, wirelessly powering the sensor using the wireless transceiver, sensing of one or more analytes in the tissue of the subject with the sensing element of the implantable sensor and generating an analyte signal representative of the analyte concentration, determining analyte data as a function of the analyte signal, and transmitting the analyte data representative of the analyte concentration to the wireless transceiver, wherein implanting comprises deploying the implantable sensor using an applicator, the applicator comprising;

a plastic body to allow applicator handling, a plastic-metal assembly to move the implantable sensor, and a needle configured to pierce the subject skin and for embedding the sensor underneath the skin with minimal tissue damage.

13. An implantable sensor with a polymeric coating, said sensor comprising:

an implantable integrated circuit connected to a sensing element, said sensing element comprising at least two or more working electrodes, a counter electrode, and a reference electrode, each made using lithographic processing, wherein each electrode comprises a conductive surface, wherein at least two working electrodes are connected to a respective potentiostat;

wherein the sensing element senses one or more analytes and generates two or more signals from the two or more working electrodes representative of said one or more analytes concentrations, said signals received by the implantable integrated circuit;

wherein the implantable integrated circuit includes:

A) an analyte signal acquisition and processing unit that receives the two or more signals from the sensing element representative of said one or more analyte concentrations;

B) an LC resonant unit comprising a tunable capacitor connected to an antenna;

C) a power management unit comprising a calibration machine, and a rectifier, wherein a rectifier output voltage is maximized through alignment of the resonant frequency of the implantable sensor with a wireless transceiver via modulation of the tunable capacitor, said power management unit connected and providing power to the analyte signal acquisition and processing unit; and D) a telemetry unit connected to the analyte signal and processing unit which transmits data representative of said analyte concentration, wherein the implantable integrated circuit is formed in CMOS on a single CMOS substrate and the sensing element is formed on top of the same CMOS substrate to generate a monolithically integrated sensor.

14. The implantable sensor as in claim 13, further comprising a hydrogel containing glucose oxidase (Gox), wherein the antenna is formed into the CMOS substrate.

15. The implantable sensor as in claim 14, wherein the antenna is made in one of a top 1 to 3 metals of the CMOS substrate.

16. The implantable sensor as in claim 13, wherein the reference, the counter, and the working electrode(s) are isolated from each other by silicon nitride.

17. The implantable sensor as in claim 13, wherein at least one sensing element electrode conductive surface is patterned and the surface patterning comprises pillars formed by CMOS, wherein the pillars have a height between 2 microns to 5 microns, and wherein the pillars are separated by a similar distance as their size.

18. The implantable sensor as in claim 13, further comprising a hydrogel containing glucose oxidase (Gox), wherein the hydrogel has a thickness between 2 to 6 microns.

19. The implantable sensor as in claim 13, wherein the telemetry unit implements CRC16 coding for error correction.

20. The implantable sensor as in claim 13, wherein the polymeric coating is a polyurethane membrane, and wherein the polyurethane membrane thickness is in the range of 0.25 to 6 microns.

21. The implantable sensor as in claim 20, wherein a second membrane is placed over the polyurethane membrane and the second membrane is hydrophilic.

22. The implantable sensor as in claim 13, wherein the multiple potentiostats are commected to a single analog to digital converter.

23. The implantable sensor as in claim 22, wherein the outputs of the multiple potentiostats are time multiplexed into the single analog to digital converter.

* * * * *